(12) United States Patent
Freeman et al.

(10) Patent No.: US 7,833,171 B2
(45) Date of Patent: *Nov. 16, 2010

(54) METHOD AND APPARATUS FOR PENETRATING TISSUE

(75) Inventors: Dominique Freeman, La Honda, CA (US); Dirk Boecker, Palo Alto, CA (US); Don Alden, Sunnyvale, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 947 days.

This patent is subject to a terminal disclaimer.

(21) Appl. No.: 11/674,191

(22) Filed: Feb. 13, 2007

(65) Prior Publication Data

US 2007/0173742 A1 Jul. 26, 2007

Related U.S. Application Data

(60) Division of application No. 10/335,218, filed on Dec. 31, 2002, now Pat. No. 7,331,931, which is a continuation-in-part of application No. 10/237,261, filed on Sep. 5, 2002, now Pat. No. 7,344,507, which is a continuation-in-part of application No. 10/127,395, filed on Apr. 19, 2002, now Pat. No. 7,025,774.

(51) Int. Cl.
*A61B 5/00* (2006.01)
(52) U.S. Cl. ..................... 600/583; 606/181
(58) Field of Classification Search ............... 606/180, 606/181, 182; 600/573, 575, 583, 584
See application file for complete search history.

(56) References Cited

U.S. PATENT DOCUMENTS

| | | | |
|---|---|---|---|
| 1,733,847 A | 10/1929 | Wilmont | |
| 2,801,633 A | 8/1957 | Mauze et al. | |
| 3,358,689 A | 12/1967 | Higgins | 128/329 |
| 3,494,358 A | 2/1970 | Grossenbacher | 128/218 |
| 3,626,929 A | 12/1971 | Sanz | 128/2 R |
| 3,742,954 A | 7/1973 | Strickland | 128/302 |
| 3,832,776 A | 9/1974 | Sawyer | 30/272 |
| 3,953,172 A | 4/1976 | Shapiro | 23/230 |
| 4,224,125 A | 9/1980 | Nakamura | 204/195 B |

(Continued)

FOREIGN PATENT DOCUMENTS

DE 4420232 12/1995

(Continued)

*Primary Examiner*—Michael J Milano
*Assistant Examiner*—Victor X Nguyen
(74) *Attorney, Agent, or Firm*—Paul Davis; Goodwin Procter LLP

(57) ABSTRACT

These and other objects of the present invention are achieved in a body fluid sampling system for use on a tissue site that includes an electrically powered drive force generator. A penetrating member is operatively coupled to the force generator. The force generator moves the member along a path out of a housing having a penetrating member exit, into the tissue site, stops in the tissue site, and withdraws out of the tissue site. A cartridge houses the penetrating member. The cartridge has first and second seals coupled to the penetrating member to maintain a sterile environment around a portion of the penetration member prior to penetrating member actuation. A user interface is configured to relay at least one of, penetrating member performance or a penetrating member setting.

19 Claims, 33 Drawing Sheets

U.S. PATENT DOCUMENTS

| | | | |
|---|---|---|---|
| 4,230,118 A | 10/1980 | Holman et al. | 128/314 |
| 4,338,174 A | 7/1982 | Tamura | 204/195 |
| 4,340,669 A | 7/1982 | Bauer | 435/14 |
| 4,353,984 A | 10/1982 | Yamada | 435/14 |
| 4,360,016 A | 11/1982 | Sarrine | 128/763 |
| 4,391,905 A | 7/1983 | Bauer | 435/14 |
| 4,391,906 A | 7/1983 | Bauer | 435/14 |
| 4,414,975 A | 11/1983 | Ryder | 128/314 |
| 4,420,564 A | 12/1983 | Tsuji | 435/288 |
| 4,426,451 A | 1/1984 | Columbus | 436/518 |
| 4,426,884 A | 1/1984 | Polchaninoff | 73/172 |
| 4,469,110 A | 9/1984 | Slama | 128/770 |
| 4,517,978 A | 5/1985 | Levin | 128/314 |
| 4,539,988 A | 9/1985 | Shirley | 128/314 |
| 4,545,382 A | 10/1985 | Higgins | 128/635 |
| 4,553,541 A | 11/1985 | Burns | 128/314 |
| 4,577,630 A | 3/1986 | Nitzsche | 128/314 |
| 4,580,564 A | 4/1986 | Anderson | 502/8 |
| 4,580,565 A | 4/1986 | Cornell | 128/314 |
| 4,590,411 A | 5/1986 | Kelly | 318/687 |
| 4,595,479 A | 6/1986 | Kimura | 204/294 |
| 4,608,997 A | 9/1986 | Conway | 128/763 |
| 4,615,340 A | 10/1986 | Cronenberg | 128/635 |
| 4,616,649 A | 10/1986 | Burns | 128/314 |
| 4,619,754 A | 10/1986 | Niki | 204/290 |
| 4,622,974 A | 11/1986 | Coleman | 128/634 |
| 4,624,253 A | 11/1986 | Burns | 128/314 |
| 4,637,393 A | 1/1987 | Ray | 128/305 |
| 4,643,189 A | 2/1987 | Mintz | 128/314 |
| 4,648,408 A | 3/1987 | Hutcheson | 128/770 |
| 4,653,511 A | 3/1987 | Goch | 128/763 |
| 4,661,768 A | 4/1987 | Carusillo | |
| 4,676,244 A | 6/1987 | Enstrom | 128/314 |
| 4,677,979 A | 7/1987 | Burns | 128/314 |
| 4,711,245 A | 12/1987 | Higgins | 128/635 |
| 4,712,548 A | 12/1987 | Enstrom | 128/314 |
| 4,715,374 A | 12/1987 | Maggio | 128/314 |
| 4,735,203 A | 4/1988 | Ryder | 128/314 |
| 4,757,022 A | 7/1988 | Shults et al. | 435/291 |
| 4,758,323 A | 7/1988 | Davis | 204/403 |
| 4,794,926 A | 1/1989 | Munsch et al. | 606/183 |
| 4,814,142 A | 3/1989 | Gleisner | 422/56 |
| 4,814,661 A | 3/1989 | Ratzlaff | 310/328 |
| 4,820,010 A | 4/1989 | Sciefres | 385/43 |
| 4,820,399 A | 4/1989 | Senda | 204/403 |
| 4,824,639 A | 4/1989 | Hildenbrand | 422/56 |
| RE32,922 E | 5/1989 | Levin | 128/314 |
| 4,827,763 A | 5/1989 | Bourland | 73/172 |
| 4,830,959 A | 5/1989 | McNeil et al. | 435/53 |
| 4,836,904 A | 6/1989 | Armstrong | 204/294 |
| 4,844,095 A | 7/1989 | Chiodo | 128/314 |
| 4,850,973 A | 7/1989 | Jordan | 604/157 |
| 4,857,274 A | 8/1989 | Simon | 422/72 |
| 4,869,249 A | 9/1989 | Crossman | 128/314 |
| 4,869,265 A | 9/1989 | McEwen | 128/774 |
| 4,873,993 A | 10/1989 | Meserol | 128/780 |
| 4,882,013 A | 11/1989 | Turner | 204/1 |
| 4,883,068 A | 11/1989 | Dechow | 128/760 |
| 4,886,499 A | 12/1989 | Cirelli | 604/131 |
| 4,889,529 A | 12/1989 | Haindl | 604/274 |
| 4,892,097 A | 1/1990 | Ranalletta | 606/182 |
| 4,895,147 A | 1/1990 | Bodicky | 606/182 |
| 4,897,173 A | 1/1990 | Nankai | 204/403 |
| 4,900,424 A | 2/1990 | Birch | 204/409 |
| 4,911,794 A | 3/1990 | Parce | 204/1 T |
| 4,920,977 A | 5/1990 | Haynes | 128/770 |
| 4,924,879 A | 5/1990 | O'Brien | |
| 4,945,045 A | 7/1990 | Forrest | 435/25 |
| 4,948,727 A | 8/1990 | Cass | 435/18 |
| 4,952,515 A | 8/1990 | Gleisner | 436/169 |
| 4,953,552 A | 9/1990 | DeMarzo | 128/635 |
| 4,966,671 A | 10/1990 | Nylander | 204/153.14 |
| 4,976,724 A | 12/1990 | Nieto | 606/182 |
| 4,983,178 A | 1/1991 | Schnell | 606/181 |
| 4,990,154 A | 2/1991 | Brown | 606/182 |
| 4,999,582 A | 3/1991 | Parks | 324/438 |
| 5,010,772 A | 4/1991 | Bourland | 73/862.04 |
| 5,010,774 A | 4/1991 | Kikuo | 73/862.04 |
| 5,014,718 A | 5/1991 | Mitchen | 128/771 |
| 5,019,974 A | 5/1991 | Beckers | 364/413.02 |
| 5,026,388 A | 6/1991 | Ingalz | 606/182 |
| 5,029,583 A | 7/1991 | Meserol | |
| 5,047,044 A | 9/1991 | Smith et al. | |
| 5,054,499 A | 10/1991 | Swierczek | 128/770 |
| 5,059,789 A | 10/1991 | Salcudean | 435/4 |
| 5,060,174 A | 10/1991 | Gross | 702/139 |
| 5,070,886 A | 12/1991 | Mitchen | 128/771 |
| 5,074,872 A | 12/1991 | Brown | 606/182 |
| 5,089,112 A | 2/1992 | Skotheim | 204/403 |
| 5,092,842 A | 3/1992 | Bechtold | 604/135 |
| 5,100,427 A | 3/1992 | Crossman | 606/182 |
| 5,100,428 A | 3/1992 | Mumford | 606/182 |
| 5,104,380 A | 4/1992 | Holman | 604/117 |
| 5,104,619 A | 4/1992 | Castro | 422/56 |
| 5,108,564 A | 4/1992 | Szuminsky | 204/153.12 |
| 5,108,889 A | 4/1992 | Smith et al. | |
| 5,116,759 A | 5/1992 | Klainer | 435/288 |
| 5,120,420 A | 6/1992 | Nankai | 204/403 |
| 5,122,244 A | 6/1992 | Hoenes | 204/153 |
| 5,126,034 A | 6/1992 | Carter | 204/403 |
| 5,128,015 A | 7/1992 | Szuminsky | 204/403 |
| 5,128,171 A | 7/1992 | Gleisner | 427/2 |
| 5,133,730 A | 7/1992 | Biro | 606/182 |
| 5,139,685 A | 8/1992 | Castro | 210/767 |
| 5,141,868 A | 8/1992 | Shanks | 435/288 |
| 5,156,611 A | 10/1992 | Haynes | 606/181 |
| 5,163,442 A | 11/1992 | Ono | 128/760 |
| 5,170,364 A | 12/1992 | Gross | 702/139 |
| D332,490 S | 1/1993 | Brown | D24/146 |
| 5,178,142 A | 1/1993 | Harjunmaa | 128/633 |
| 5,181,910 A | 1/1993 | Scanlon | 604/67 |
| 5,181,914 A | 1/1993 | Zook | 604/307 |
| 5,183,042 A | 2/1993 | Harjunmaa et al. | 128/633 |
| 5,185,256 A | 2/1993 | Nankai | 435/174 |
| 5,187,100 A | 2/1993 | Matzinger | 436/16 |
| 5,192,415 A | 3/1993 | Yoshioka | 204/403 |
| 5,196,025 A | 3/1993 | Ranalletta | 606/182 |
| 5,201,324 A | 4/1993 | Swierczek | 128/770 |
| 5,205,920 A | 4/1993 | Oyama | 204/403 |
| 5,212,879 A | 5/1993 | Biro | 29/437 |
| 5,216,597 A | 6/1993 | Beckers | 364/413.02 |
| 5,217,480 A | 6/1993 | Haber | 606/182 |
| 5,228,972 A | 7/1993 | Osaka | 204/415 |
| 5,229,282 A | 7/1993 | Yoshioka | 435/177 |
| 5,230,866 A | 7/1993 | Shartle | 422/103 |
| 5,231,993 A | 8/1993 | Haber et al. | 128/770 |
| 5,250,066 A | 10/1993 | Lambert | 606/181 |
| 5,251,126 A | 10/1993 | Kahn | 364/413.11 |
| 5,253,656 A | 10/1993 | Rincoe | 128/782 |
| 5,256,998 A | 10/1993 | Becker | 335/229 |
| 5,264,103 A | 11/1993 | Yoshioka | 204/403 |
| 5,264,105 A | 11/1993 | Gregg | 204/403 |
| 5,264,106 A | 11/1993 | McAleer | 204/403 |
| 5,266,179 A | 11/1993 | Nankai | 204/401 |
| D342,573 S | 12/1993 | Cerola | D24/147 |
| 5,272,087 A | 12/1993 | El Murr | 435/291 |
| 5,277,181 A | 1/1994 | Mendelson | 128/633 |
| 5,282,822 A | 2/1994 | Macors | 606/182 |
| 5,286,362 A | 2/1994 | Hoenes | 204/403 |
| 5,286,364 A | 2/1994 | Yacynych | 204/418 |
| 5,288,636 A | 2/1994 | Pollman | 435/288 |
| 5,304,192 A | 4/1994 | Crouse | 606/181 |
| 5,304,193 A | 4/1994 | Zhadanov | 606/182 |
| 5,312,590 A | 5/1994 | Gunasingham | 422/56 |

| | | | | | | | |
|---|---|---|---|---|---|---|---|
| 5,314,441 A | 5/1994 | Cusack | 606/182 | 5,582,697 A | 12/1996 | Ikeda | 204/403 |
| 5,314,442 A | 5/1994 | Morita | 606/182 | 5,584,846 A | 12/1996 | Mawhirt | 606/181 |
| 5,316,012 A | 5/1994 | Siegal | 128/744 | 5,593,852 A | 1/1997 | Heller | 435/14 |
| 5,318,583 A | 6/1994 | Rabenau | 606/182 | 5,609,749 A | 3/1997 | Yamauchi | 205/777.5 |
| 5,320,607 A | 6/1994 | Ishibashi | 604/115 | 5,613,978 A | 3/1997 | Harding | 606/181 |
| 5,324,302 A | 6/1994 | Crouse | 606/181 | 5,620,579 A | 4/1997 | Genshaw | 204/402 |
| 5,324,303 A | 6/1994 | Strong | 606/181 | 5,624,537 A | 4/1997 | Turner | 204/403 |
| 5,332,479 A | 7/1994 | Uenoyama | 204/153.12 | D379,516 S | 5/1997 | Rutter | D24/146 |
| 5,350,392 A | 9/1994 | Purcell | 606/182 | 5,628,764 A | 5/1997 | Schraga | 606/182 |
| 5,352,351 A | 10/1994 | White | 204/406 | 5,628,765 A | 5/1997 | Morita | 606/182 |
| 5,354,287 A | 10/1994 | Wacks | 604/232 | 5,628,890 A | 5/1997 | Carter | 204/403 |
| 5,354,447 A | 10/1994 | Uenoyama | 204/403 | 5,640,954 A | 6/1997 | Pfeiffer | 128/635 |
| 5,356,420 A | 10/1994 | Czernecki | 606/182 | 5,643,306 A | 7/1997 | Schraga | 606/182 |
| 5,360,410 A | 11/1994 | Wacks | 604/232 | 5,645,555 A | 7/1997 | Davis | 606/182 |
| 5,366,469 A | 11/1994 | Steg | 606/182 | 5,650,062 A | 7/1997 | Ikeda | 205/778 |
| 5,366,470 A | 11/1994 | Ramel | 606/183 | 5,653,863 A | 8/1997 | Genshaw | 205/777.5 |
| 5,366,609 A | 11/1994 | White | 204/403 | 5,657,760 A | 8/1997 | Ying et al. | 128/660.03 |
| 5,371,687 A | 12/1994 | Holmes | 364/514 | 5,658,444 A | 8/1997 | Black | 204/415 |
| 5,375,397 A | 12/1994 | Ferrand | 54/66 | 5,662,127 A | 9/1997 | De Vaughn | 128/765 |
| 5,378,628 A | 1/1995 | Graetezel | 435/288 | 5,662,672 A | 9/1997 | Pambianchi | 606/181 |
| 5,382,346 A | 1/1995 | Uenoyama | 204/403 | 5,676,143 A | 10/1997 | Simonsen | 128/633 |
| 5,383,885 A | 1/1995 | Bland | 606/182 | 5,680,858 A | 10/1997 | Hansen et al. | 128/635 |
| 5,389,534 A | 2/1995 | Gentezkow | 435/180 | 5,680,872 A | 10/1997 | Sesekura | 128/760 |
| 5,393,903 A | 2/1995 | Graetzel | 556/137 | 5,682,884 A | 11/1997 | Hill | 128/637 |
| 5,395,387 A | 3/1995 | Burns | 606/181 | 5,683,562 A | 11/1997 | Schaffar | 204/403 |
| 5,397,334 A | 3/1995 | Schenk | 606/182 | 5,695,947 A | 12/1997 | Guo | 435/11 |
| 5,401,376 A | 3/1995 | Foos | 204/415 | 5,700,695 A | 12/1997 | Yassinzadeh | 436/180 |
| 5,402,798 A | 4/1995 | Swierczek | 128/770 | 5,705,045 A | 1/1998 | Park | 204/403 |
| 5,405,511 A | 4/1995 | White | 204/153.1 | 5,708,247 A | 1/1998 | McAleer | 204/403 |
| 5,407,545 A | 4/1995 | Hirose | 204/153.12 | 5,709,668 A | 1/1998 | Wacks | 604/232 |
| 5,407,554 A | 4/1995 | Saurer | 204/403 | 5,709,699 A | 1/1998 | Warner | 606/181 |
| 5,407,818 A | 4/1995 | Gentezkow | 435/180 | 5,710,011 A | 1/1998 | Forrow | 435/25 |
| 5,409,583 A | 4/1995 | Yoshioka | 204/153.12 | 5,720,862 A | 2/1998 | Hamamoto | 204/403 |
| 5,409,664 A | 4/1995 | Allen | | 5,720,924 A | 2/1998 | Eikmeier | 422/102 |
| 5,410,059 A | 4/1995 | Fraser | 546/10 | D392,391 S | 3/1998 | Douglas | D24/225 |
| 5,423,847 A | 6/1995 | Strong | 606/182 | 5,723,284 A | 3/1998 | Ye | 435/4 |
| 5,436,161 A | 7/1995 | Bergstrom | 435/291 | 5,727,548 A | 3/1998 | Hill | 128/637 |
| 5,437,999 A | 8/1995 | Diebold | 435/288 | 5,730,753 A | 3/1998 | Morita | 606/181 |
| 5,438,271 A | 8/1995 | White | 324/444 | 5,733,300 A | 3/1998 | Pambianchi | 606/181 |
| 5,443,701 A | 8/1995 | Willner | 204/153 | D393,716 S | 4/1998 | Brenneman | D24/147 |
| 5,445,920 A | 8/1995 | Saito | 430/311 | D393,717 S | 4/1998 | Brenneman | D24/147 |
| D362,719 S | 9/1995 | Kaplan | D24/147 | 5,738,244 A | 4/1998 | Charlton et al. | 221/26 |
| 5,454,828 A | 10/1995 | Schraga | 606/181 | 5,741,228 A | 4/1998 | Lambrecht | 604/93 |
| 5,456,875 A | 10/1995 | Lambert | 264/328.1 | 5,741,634 A | 4/1998 | Nozoe | 435/4 |
| 5,464,418 A | 11/1995 | Schraga | 606/182 | RE35,803 E | 5/1998 | Lange | 606/182 |
| 5,471,102 A | 11/1995 | Becker | 310/50 | 5,746,217 A | 5/1998 | Erickson | 128/760 |
| 5,476,474 A | 12/1995 | Davis | 606/182 | 5,746,898 A | 5/1998 | Preidel | 204/403 |
| 5,480,387 A | 1/1996 | Gabriel | 604/134 | 5,755,733 A | 5/1998 | Morita | 606/182 |
| 5,487,748 A | 1/1996 | Marshall | 606/182 | 5,759,364 A | 6/1998 | Charlton | 204/403 |
| 5,496,453 A | 3/1996 | Uenoyama | 205/777.5 | 5,762,770 A | 6/1998 | Pritchard | 204/403 |
| 5,498,542 A | 3/1996 | Corey | 435/283.1 | 5,770,086 A | 6/1998 | Indriksons et al. | |
| 5,507,288 A | 4/1996 | Bocker | 128/633 | 5,770,369 A | 6/1998 | Meade | 435/6 |
| 5,508,171 A | 4/1996 | Walling | 205/777.5 | 5,772,586 A | 6/1998 | Heinonen | 600/300 |
| 5,509,410 A | 4/1996 | Hill | 128/637 | 5,772,677 A | 6/1998 | Mawhirt | 606/181 |
| 5,510,266 A | 4/1996 | Bonner et al. | 436/43 | 5,773,270 A | 6/1998 | D'Orazio | 435/177 |
| 5,512,159 A | 4/1996 | Yoshioka | 204/403 | 5,776,719 A | 7/1998 | Douglas | 435/28 |
| 5,514,152 A | 5/1996 | Smith et al. | | 5,782,770 A | 7/1998 | Mooradian | 600/476 |
| 5,518,006 A | 5/1996 | Mawhirt | 128/770 | 5,782,852 A | 7/1998 | Foggia | 606/182 |
| 5,524,636 A | 6/1996 | Sarvazyan | 128/774 | 5,788,652 A | 8/1998 | Rahn | 600/577 |
| 5,525,511 A | 6/1996 | D'Costa | 435/287.9 | 5,794,219 A | 8/1998 | Brown | 705/37 |
| 5,527,333 A | 6/1996 | Nikkels | 606/182 | 5,795,725 A | 8/1998 | Buechler | 435/7.1 |
| 5,527,334 A | 6/1996 | Kanner | 606/182 | 5,795,774 A | 8/1998 | Matsumoto | 435/287.9 |
| 5,540,676 A | 7/1996 | Freiberg | | 5,797,940 A | 8/1998 | Mawhirt | 606/167 |
| 5,540,709 A | 7/1996 | Ramel | 606/183 | 5,797,942 A | 8/1998 | Schraga | 606/182 |
| 5,543,326 A | 8/1996 | Heller | 435/287.9 | 5,798,030 A | 8/1998 | Raguse | 204/403 |
| 5,545,174 A | 8/1996 | Schenk | 606/182 | 5,798,031 A | 8/1998 | Charlton | 204/403 |
| 5,547,702 A | 8/1996 | Gleisner | 427/2.13 | 5,801,057 A | 9/1998 | Smart | 436/68 |
| 5,554,166 A | 9/1996 | Lange | 606/182 | 5,807,375 A | 9/1998 | Gross | 604/890.1 |
| 5,558,834 A | 9/1996 | Chu | 422/55 | 8,800,781 | 9/1998 | Gavin | 422/73 |
| 5,569,286 A | 10/1996 | Peckham | 606/181 | 5,820,551 A | 10/1998 | Hill | 600/347 |
| 5,569,287 A | 10/1996 | Tezuka | 606/182 | 5,822,715 A | 10/1998 | Worthington | 702/19 |
| 5,571,132 A | 11/1996 | Mawhirt | 606/182 | 5,824,491 A | 10/1998 | Priest | 435/28 |
| 5,575,895 A | 11/1996 | Ikeda | 204/403 | 5,828,943 A | 10/1998 | Brown | 434/258 |

| | | | | | | | | |
|---|---|---|---|---|---|---|---|---|
| 5,830,219 | A | 11/1998 | Bird et al. ........... 606/130 | | 6,030,827 | A | 2/2000 | Davis ................. 435/287 |
| 5,832,448 | A | 11/1998 | Brown ................. 705/2 | | 6,032,119 | A | 2/2000 | Brown ................. 705/2 |
| 5,840,020 | A | 11/1998 | Heinonen ............. 600/309 | | 6,033,421 | A | 3/2000 | Theiss ............... 606/186 |
| 5,840,171 | A | 11/1998 | Birch ............... 205/335 | | 6,033,866 | A | 3/2000 | Guo ................. 435/14 |
| 5,849,174 | A | 12/1998 | Sanghera ............ 205/775 | | 6,041,253 | A | 3/2000 | Kost ................. 604/20 |
| 5,853,373 | A | 12/1998 | Griffith ............. 600/554 | | 6,048,352 | A | 4/2000 | Douglas .............. 606/181 |
| D403,975 | S | 1/1999 | Douglas .............. D10/81 | | D424,696 | S | 5/2000 | Ray ................. D24/169 |
| 5,857,983 | A | 1/1999 | Douglas .............. 600/538 | | 6,056,701 | A | 5/2000 | Duchon ............. 600/583 |
| 5,860,922 | A | 1/1999 | Gordon et al. ........ 600/431 | | 6,060,327 | A | 5/2000 | Keen ................. 436/518 |
| 5,866,353 | A | 2/1999 | Berneth .............. 435/26 | | 6,061,128 | A | 5/2000 | Zweig ............... 356/243.4 |
| 5,868,135 | A | 2/1999 | Kaufman ............. 128/630 | | 6,063,039 | A | 5/2000 | Cunningham ........... 600/573 |
| 5,868,772 | A | 2/1999 | LeVaughn ............. 606/181 | | 6,066,103 | A | 5/2000 | Duchon ............. 600/583 |
| 5,869,972 | A | 2/1999 | Birch ............... 324/439 | | 6,066,296 | A | 5/2000 | Brady ............... 422/63 |
| 5,871,494 | A | 2/1999 | Simons et al. | | 6,067,463 | A | 5/2000 | Jeng ................. 600/336 |
| 5,872,713 | A | 2/1999 | Douglas .............. 702/85 | | 6,068,615 | A | 5/2000 | Brown ............... 604/207 |
| 5,873,887 | A | 2/1999 | King ................. 606/182 | | D426,638 | S | 6/2000 | Ray ................. D24/169 |
| 5,876,957 | A | 3/1999 | Douglas ............. 435/28 | | 6,071,249 | A | 6/2000 | Cunningham ........... 600/578 |
| 5,879,163 | A | 3/1999 | Brown ............... 434/236 | | 6,071,250 | A | 6/2000 | Douglas .............. 600/583 |
| 5,879,310 | A | 3/1999 | Sopp ................. 600/578 | | 6,071,251 | A | 6/2000 | Cunningham ........... 600/584 |
| 5,879,373 | A | 3/1999 | Roeper ............... 606/344 | | 6,071,294 | A | * 6/2000 | Simons et al. ......... 606/181 |
| 5,882,494 | A | 3/1999 | van Antwerp ......... 204/403 | | 6,074,360 | A | 6/2000 | Hans-Peter ........... 604/57 |
| 5,885,211 | A | 3/1999 | Eppstein ............ 600/309 | | 6,077,408 | A | 6/2000 | Miyamoto ............ 204/403 |
| 5,887,133 | A | 3/1999 | Brown ............... 395/200.3 | | 6,080,172 | A | 6/2000 | Fujiwara ............ 606/166 |
| RE36,191 | E | 4/1999 | Solomon ............. 395/308 | | 6,083,710 | A | 7/2000 | Heller ............... 435/14 |
| 5,893,870 | A | 4/1999 | Talen ............... 606/201 | | 6,086,545 | A | 7/2000 | Roe ................. 600/570 |
| 5,897,493 | A | 4/1999 | Brown ............... 600/300 | | 6,086,562 | A | 7/2000 | Jacobsen ............ 604/156 |
| 5,899,855 | A | 5/1999 | Brown ............... 600/301 | | 6,090,078 | A | 7/2000 | Erskine ............. 604/198 |
| 5,899,915 | A | 5/1999 | Saadat et al. | | 6,093,146 | A | 7/2000 | Filangeri ........... 600/300 |
| 5,900,130 | A | 5/1999 | Benvegnu ............ 204/453 | | 6,093,156 | A | 7/2000 | Cunningham et al. .... 600/573 |
| 5,906,921 | A | 5/1999 | Ikeda ............... 435/25 | | 6,101,478 | A | 8/2000 | Brown ............... 705/2 |
| D411,619 | S | 6/1999 | Duchon .............. D24/146 | | 6,103,033 | A | 8/2000 | Say ................. 156/73.1 |
| 5,913,310 | A | 6/1999 | Brown ............... 128/897 | | 6,107,083 | A | 8/2000 | Collins ............. 435/288 |
| 5,916,156 | A | 6/1999 | Hildenbrand ......... 600/347 | | 6,113,578 | A | 9/2000 | Brown ............... 604/207 |
| 5,916,229 | A | 6/1999 | Evans ............... 606/171 | | 6,120,676 | A | 9/2000 | Heller .............. 205/777.5 |
| 5,916,230 | A | 6/1999 | Brenneman ........... 606/172 | | 6,121,009 | A | 9/2000 | Heller .............. 435/14 |
| 5,918,603 | A | 7/1999 | Brown ............... 128/897 | | 6,122,536 | A | 9/2000 | Sun ................. 600/341 |
| 5,921,963 | A | 7/1999 | Erez ................ 604/156 | | 6,129,823 | A | 10/2000 | Hughes .............. 204/403.01 |
| 5,922,188 | A | 7/1999 | Ikeda ............... 204/777.5 | | 6,133,837 | A | 10/2000 | Riley ............... 340/573.1 |
| RE36,268 | E | 8/1999 | Szuminsky ........... 205/777.5 | | 6,134,461 | A | 10/2000 | Say ................. 600/345 |
| 5,933,136 | A | 8/1999 | Brown ............... 345/327 | | 6,144,837 | A | 11/2000 | Quy ................. 434/307 R |
| 5,935,075 | A | 8/1999 | Casscells et al. .... 600/474 | | 6,151,586 | A | 11/2000 | Brown ............... 705/14 |
| 5,940,153 | A | 8/1999 | Castaneda | | 6,153,069 | A | 11/2000 | Pottgen ............. 204/403 |
| 5,942,102 | A | 8/1999 | Hodges .............. 205/775 | | RE36,991 | E | 12/2000 | Yamamoto ............ 204/403 |
| 5,951,300 | A | 9/1999 | Brown ............... 434/236 | | 6,155,267 | A | 12/2000 | Nelson .............. 128/899 |
| 5,951,492 | A | 9/1999 | Douglas ............. 600/583 | | 6,155,992 | A | 12/2000 | Henning ............. 600/583 |
| 5,951,493 | A | 9/1999 | Douglas et al. ...... 600/583 | | 6,157,442 | A | 12/2000 | Raskas .............. 356/39 |
| 5,951,836 | A | 9/1999 | McAleer ............. 204/403 | | 6,161,095 | A | 12/2000 | Brown ............... 705/2 |
| 5,954,738 | A | 9/1999 | LeVaughn ............ 606/181 | | 6,162,611 | A | 12/2000 | Heller .............. 435/14 |
| 5,956,501 | A | 9/1999 | Brown ............... 395/500.32 | | 6,167,362 | A | 12/2000 | Brown ............... 703/11 |
| 5,958,199 | A | 9/1999 | Miyamoto ............ 204/403 | | 6,167,386 | A | 12/2000 | Brown ............... 705/37 |
| 5,960,403 | A | 9/1999 | Brown ............... 705/2 | | 6,168,563 | B1 | 1/2001 | Brown ............... 600/301 |
| 5,964,718 | A | 10/1999 | Duchon .............. 600/583 | | 6,171,325 | B1 | 1/2001 | Mauze et al. ........ 606/171 |
| 5,965,380 | A | 10/1999 | Heller .............. 435/14 | | 6,175,752 | B1 | 1/2001 | Say ................. 600/345 |
| 5,971,941 | A | * 10/1999 | Simons et al. ....... 600/573 | | 6,177,000 | B1 | 1/2001 | Peterson ............ 205/777.5 |
| 5,972,199 | A | 10/1999 | Heller .............. 205/777.5 | | 6,177,931 | B1 | 1/2001 | Alexander et al. |
| 5,972,715 | A | 10/1999 | Celentano ........... 436/164 | | 6,186,145 | B1 | 2/2001 | Brown ............... 128/897 |
| 5,974,124 | A | 10/1999 | Schlueter ........... 379/106.02 | | 6,190,612 | B1 | 2/2001 | Berger .............. 422/82.07 |
| 5,983,193 | A | 11/1999 | Heinonen ............ 705/2 | | 6,191,852 | B1 | 2/2001 | Paffhausen .......... 356/244 |
| 5,985,116 | A | 11/1999 | Ikeda ............... 204/403 | | 6,192,891 | B1 | 2/2001 | Gravel .............. 128/920 |
| 5,985,559 | A | 11/1999 | Brown ............... 435/6 | | 6,194,900 | B1 | 2/2001 | Freeman ............. 324/321 |
| 5,993,400 | A | 11/1999 | Rincoe .............. 600/595 | | 6,197,257 | B1 | 3/2001 | Raskas .............. 422/82.05 |
| 5,997,476 | A | 12/1999 | Brown ............... 600/300 | | 6,206,841 | B1 | 3/2001 | Cunningham et al. .... 600/584 |
| 5,997,561 | A | 12/1999 | Boecker ............. 606/182 | | 6,210,272 | B1 | 4/2001 | Brown ............... 463/1 |
| 5,997,817 | A | 12/1999 | Crismore ............ 422/58 | | 6,212,417 | B1 | 4/2001 | Ikeda ............... 204/403.14 |
| 5,997,818 | A | 12/1999 | Hackner ............. 422/681 | | 6,214,804 | B1 | 4/2001 | Felgner ............. 514/44 |
| 6,001,067 | A | 12/1999 | Shults .............. 600/584 | | 6,221,238 | B1 | 4/2001 | Grundig ............. 205/777.5 |
| 6,015,392 | A | 1/2000 | Douglas ............. 600/583 | | 6,225,078 | B1 | 5/2001 | Ikeda ............... 435/25 |
| 6,020,110 | A | 2/2000 | Williams ............ 430/315 | | 6,228,100 | B1 | 5/2001 | Schraga |
| 6,022,324 | A | 2/2000 | Skinner ............. 600/566 | | 6,230,501 | B1 | 5/2001 | Bailey .............. 62/51.1 |
| 6,022,366 | A | 2/2000 | Schraga ............. 606/181 | | 6,233,471 | B1 | 5/2001 | Berner .............. 600/345 |
| 6,023,686 | A | 2/2000 | Brown ............... 705/37 | | 6,233,539 | B1 | 5/2001 | Brown ............... 703/11 |
| 6,027,459 | A | 2/2000 | Shain et al. | | 6,240,393 | B1 | 5/2001 | Brown ............... 705/1 |
| 6,030,399 | A | 2/2000 | Ignotz .............. 606/167 | | 6,241,862 | B1 | 6/2001 | McAleer ............. 204/403 |

| | | | | | | | |
|---|---|---|---|---|---|---|---|
| 6,245,060 B1 | 6/2001 | Loomis | 606/9 | 6,503,381 B1 | 1/2003 | Gotoh | 204/403.14 |
| 6,246,992 B1 | 6/2001 | Brown | 705/2 | 6,506,168 B1 | 1/2003 | Fathallah | 600/578 |
| 6,248,065 B1 | 6/2001 | Brown | 600/300 | 6,508,785 B1 | 1/2003 | Eppstein | 604/113 |
| 6,251,260 B1 | 6/2001 | Heller | 205/777.5 | 6,514,270 B1 | 2/2003 | Schraga | 606/182 |
| 6,254,831 B1 | 7/2001 | Barnard | 422/82.08 | 6,514,460 B1 | 2/2003 | Fendrock | 422/55 |
| 6,256,533 B1 | 7/2001 | Vuzhakov | 604/21 | 6,519,241 B1 | 2/2003 | Theimer | 370/338 |
| 6,258,229 B1 | 7/2001 | Winarta | 204/403 | 6,520,326 B2 | 2/2003 | McIvor | 206/305 |
| 6,258,254 B1 | 7/2001 | Miyamoto | 205/777.5 | 6,527,778 B2 | 3/2003 | Athanasiou | 606/80 |
| 6,261,519 B1 | 7/2001 | Harding | | 6,530,892 B1 | 3/2003 | Kelly | 600/583 |
| 6,268,161 B1 | 7/2001 | Han | 435/14 | 6,530,937 B1 | 3/2003 | Schraga | 606/182 |
| 6,270,455 B1 | 8/2001 | Brown | 600/300 | 6,533,949 B1 | 3/2003 | Yeshurun | 216/11 |
| 6,270,637 B1 | 8/2001 | Crismore | 204/403 | 6,537,207 B1 | 3/2003 | Rice | 600/121 |
| 6,272,359 B1 | 8/2001 | Kivela | 455/567 | 6,537,242 B1 | 3/2003 | Palmer | 604/22 |
| 6,281,006 B1 | 8/2001 | Heller | 435/287.9 | 6,537,292 B1 | 3/2003 | Lee | 606/182 |
| 6,283,982 B1 | 9/2001 | Levaughn | 606/172 | 6,540,672 B1 | 4/2003 | Simonsen | 600/300 |
| 6,284,478 B1 | 9/2001 | Heller | 435/14 | 6,540,675 B1 | 4/2003 | Aceti | 600/309 |
| 6,285,448 B1 | 9/2001 | Kuenstner | 356/39 | 6,540,762 B1 | 4/2003 | Bertling | 606/182 |
| 6,290,683 B1 | 9/2001 | Erez | 604/273 | 6,540,891 B1 | 4/2003 | Stewart | 204/403.14 |
| 6,294,897 B1 | 9/2001 | Champlin | 320/153 | 6,541,266 B2 | 4/2003 | Modzelewski | 436/95 |
| 6,295,506 B1 | 9/2001 | Heinonen | 702/104 | 6,547,954 B2 | 4/2003 | Ikeda | 205/777.5 |
| 6,299,757 B1 | 10/2001 | Feldman | 205/775 | 6,549,796 B2 | 4/2003 | Sohrab | 600/345 |
| 6,302,844 B1 | 10/2001 | Walker | 600/300 | 6,551,494 B1 | 4/2003 | Heller | 205/777.5 |
| 6,302,855 B1 | 10/2001 | Lav | 600/584 | 6,553,244 B2 | 4/2003 | Lesho | 600/347 |
| 6,305,804 B1 | 10/2001 | Rice | 351/221 | 6,554,381 B2 | 4/2003 | Locher | 347/7 |
| 6,306,347 B1 | 10/2001 | Mason | 422/58 | 6,555,061 B1 | 4/2003 | Leong | 422/58 |
| 6,309,535 B1 | 10/2001 | Williams | 205/777.5 | 6,558,320 B1 | 5/2003 | Causey | 600/300 |
| 6,312,612 B1 | 11/2001 | Sherman | 216/2 | 6,558,361 B1 | 5/2003 | Yeshurun | 604/272 |
| 6,315,738 B1 | 11/2001 | Nishikawa | | 6,558,402 B1 | 5/2003 | Chelak | 606/182 |
| 6,322,574 B1 | 11/2001 | Lloyd | 606/181 | 6,558,528 B1 | 5/2003 | Matzinger | 205/777.5 |
| 6,329,161 B1 | 12/2001 | Heller | 435/14 | 6,560,471 B1 | 5/2003 | Heller | 600/347 |
| 6,330,426 B2 | 12/2001 | Brown | 434/307 R | 6,561,978 B1 | 5/2003 | Conn | 600/309 |
| 6,331,163 B1 | 12/2001 | Kaplan | 600/486 | 6,561,989 B2 | 5/2003 | Whitson | 600/573 |
| 6,334,363 B1 | 1/2002 | Testud | 73/862 | 6,562,210 B1 | 5/2003 | Bhullar | 204/403.3 |
| 6,334,778 B1 | 1/2002 | Brown | 434/258 | 6,565,509 B1 | 5/2003 | Say | 600/365 |
| 6,334,856 B1 | 1/2002 | Allen | 604/191 | 6,565,808 B2 | 5/2003 | Hudak | 422/58 |
| 6,338,790 B1 | 1/2002 | Feldman | 205/777.5 | 6,569,157 B1 | 5/2003 | Shain | 606/12 |
| 6,349,229 B1 | 2/2002 | Watanabe | 600/345 | 6,571,651 B1 | 6/2003 | Hodges | 73/864.72 |
| 6,350,273 B1 | 2/2002 | Minagawa | 606/186 | 6,572,566 B2 | 6/2003 | Effenhauser | 600/584 |
| 6,350,451 B1 | 2/2002 | Horn | 424/184.1 | 6,574,490 B2 | 6/2003 | Abbink | 600/316 |
| 6,352,523 B1 | 3/2002 | Brown | 604/207 | 6,575,905 B2 | 6/2003 | Knobbe | 600/365 |
| 6,353,753 B1 | 3/2002 | Flock | 600/473 | 6,576,101 B1 | 6/2003 | Heller | 204/403.14 |
| 6,364,889 B1 | 4/2002 | Kheiri et al. | 606/181 | 6,576,117 B1 | 6/2003 | Iketaki et al. | 205/777.5 |
| 6,368,273 B1 | 4/2002 | Brown | 600/300 | 6,576,416 B2 | 6/2003 | Haviland | 435/4 |
| 6,375,469 B1 | 4/2002 | Brown | 434/236 | 6,579,690 B1 | 6/2003 | Bonnecaze et al. | 435/14 |
| 6,379,301 B1 | 4/2002 | Worthington | 600/309 | 6,582,573 B2 | 6/2003 | Douglas | 204/403.1 |
| 6,379,324 B1 | 4/2002 | Gartstein | 604/22 | 6,587,705 B1 | 7/2003 | Kim et al. | 600/347 |
| 6,379,969 B1 | 4/2002 | Mauze et al. | | 6,589,260 B1 | 7/2003 | Schmelzeisen | 606/181 |
| 6,381,577 B1 | 4/2002 | Brown | 705/2 | 6,589,261 B1 | 7/2003 | Abulhaj | 606/181 |
| 6,387,709 B1 | 5/2002 | Mason | 436/164 | 6,591,125 B1 | 7/2003 | Buse | 600/347 |
| 6,391,005 B1 * | 5/2002 | Lum et al. | 604/117 | 6,592,745 B1 | 7/2003 | Feldman | 205/777.5 |
| 6,399,394 B1 | 6/2002 | Dahm | 436/180 | 6,595,919 B2 | 7/2003 | Berner | 600/365 |
| 6,413,410 B1 | 7/2002 | Hodges | 205/775 | 6,599,407 B2 | 7/2003 | Taniike | 204/403.1 |
| 6,413,411 B1 | 7/2002 | Pottgen | 205/777.5 | 6,599,693 B1 | 7/2003 | Webb | 435/4 |
| 6,421,633 B1 | 7/2002 | Heinonen | 703/11 | 6,602,205 B1 | 8/2003 | Erickson | 600/573 |
| 6,423,014 B1 | 7/2002 | Churchill et al. | | 6,602,268 B2 | 8/2003 | Kuhr | 606/181 |
| 6,428,664 B1 | 8/2002 | Bhullar | 204/403.03 | 6,602,678 B2 | 8/2003 | Kwon | 435/14 |
| 6,436,256 B1 | 8/2002 | Williams | 204/403.06 | 6,604,050 B2 | 8/2003 | Trippel | 702/19 |
| 6,436,721 B1 | 8/2002 | Kuo | 436/514 | 6,607,494 B1 | 8/2003 | Fowler | 600/570 |
| 6,440,645 B1 | 8/2002 | Yon-Hin | 430/322 | 6,607,658 B1 | 8/2003 | Heller | 205/777.5 |
| 6,451,040 B1 | 9/2002 | Purcell | 606/181 | 6,616,616 B2 | 9/2003 | Fritz | 600/583 |
| 6,458,258 B2 | 10/2002 | Taniike | 204/403 | 6,616,819 B1 | 9/2003 | Liamos | 204/403.02 |
| 6,462,162 B2 | 10/2002 | van Antwerp | 528/77 | 6,618,934 B1 | 9/2003 | Feldman | 29/830 |
| 6,464,649 B1 | 10/2002 | Duchon | 600/583 | 6,620,112 B2 | 9/2003 | Klitmose | 600/583 |
| 6,471,903 B2 | 10/2002 | Sherman | 264/328.1 | 6,623,501 B2 | 9/2003 | Heller | 606/181 |
| 6,475,436 B1 | 11/2002 | Schabbach | 422/64 | 6,626,851 B2 | 9/2003 | Hirao | 600/576 |
| 6,475,750 B1 | 11/2002 | Han | 435/14 | 6,635,222 B2 | 10/2003 | Kent | 422/22 |
| 6,477,394 B2 | 11/2002 | Rice | 600/318 | 6,638,772 B1 | 10/2003 | Douglas | 436/518 |
| 6,477,424 B1 | 11/2002 | Thompson | 607/60 | 6,641,533 B2 | 11/2003 | Causey | 600/300 |
| 6,484,046 B1 | 11/2002 | Say | 600/345 | 6,645,142 B2 | 11/2003 | Braig | 600/300 |
| 6,494,830 B1 | 12/2002 | Wessel | 600/300 | 6,645,219 B2 | 11/2003 | Roe | 606/182 |
| 6,501,404 B2 | 12/2002 | Walker | 341/143 | 6,645,368 B1 | 11/2003 | Beatty | 205/792 |
| 6,503,209 B2 | 1/2003 | Hakky et al. | | 6,650,915 B2 | 11/2003 | Routt | 600/319 |
| 6,503,231 B1 | 1/2003 | Praunsnitz | 604/272 | 6,652,720 B1 | 11/2003 | Mansouri | 204/403.11 |

| Patent No. | Date | Name | Class |
|---|---|---|---|
| 6,656,702 B1 | 12/2003 | Yugawa | 435/26 |
| 6,659,966 B2 | 12/2003 | Essenpreis | 600/583 |
| 6,660,018 B2 | 12/2003 | Lum | 606/181 |
| 6,671,527 B2 | 12/2003 | Peterson | 600/316 |
| 6,679,841 B2 | 1/2004 | Bojan | 600/309 |
| 6,679,852 B1 | 1/2004 | Schmelzeisen-Redeker | 600/583 |
| 6,706,000 B2 | 3/2004 | Perez | 600/583 |
| 6,706,049 B2 | 3/2004 | Moerman | 606/181 |
| 6,706,159 B2 | 3/2004 | Moerman | 204/403.03 |
| 6,706,232 B2 | 3/2004 | Hasegawa | 264/403.09 |
| 6,713,660 B1 | 3/2004 | Roe | 604/361 |
| 6,719,887 B2 | 4/2004 | Hasegawa | 204/403.09 |
| 6,719,923 B2 | 4/2004 | Stiene | 252/511 |
| 6,721,586 B2 | 4/2004 | Kiser | 600/345 |
| 6,723,046 B2 | 4/2004 | Lichtenstein | 600/300 |
| 6,723,111 B2 | 4/2004 | Abulhaj | 606/181 |
| 6,723,371 B2 | 4/2004 | Chih-hui | 472/2.13 |
| 6,723,500 B2 | 4/2004 | Yu | 435/4 |
| 6,726,818 B2 | 4/2004 | Cui | 204/403.01 |
| 6,733,493 B2 | 5/2004 | Gruzdev | 606/9 |
| 6,736,777 B2 | 5/2004 | Kim | 600/365 |
| 6,740,623 B2 | 5/2004 | Yamamoto et al. | 204/403.14 |
| 6,743,211 B1 | 6/2004 | Prausnitz | 604/272 |
| 6,743,635 B2 | 6/2004 | Neel | 436/95 |
| 6,749,618 B2 | 6/2004 | Levaughn | 606/182 |
| 6,749,792 B2 | 6/2004 | Olsen | 264/328.1 |
| 6,751,491 B2 | 6/2004 | Lew | 600/345 |
| 6,752,817 B2 | 6/2004 | Flora | 606/181 |
| 6,759,190 B2 | 7/2004 | Lin | 435/4 |
| 6,764,496 B2 | 7/2004 | Schraga | 606/182 |
| 6,764,581 B1 | 7/2004 | Forrow | 204/403 |
| 6,767,441 B1 | 7/2004 | Cai | 204/403.03 |
| 6,773,671 B1 | 8/2004 | Lewis | 422/58 |
| 6,776,888 B2 | 8/2004 | Yamamoto | 204/403.06 |
| 6,780,645 B2 | 8/2004 | Hayter | 436/8 |
| 6,780,647 B2 | 8/2004 | Fujiwara | 436/169 |
| 6,783,502 B2 | 8/2004 | Orloff | 600/583 |
| 6,783,537 B1 | 8/2004 | Kuhr | 606/182 |
| 6,784,274 B2 | 8/2004 | van Antwerp | 528/77 |
| 6,786,874 B2 | 9/2004 | Grace | 600/573 |
| 6,787,013 B2 | 9/2004 | Chang | 204/412 |
| 6,787,109 B2 | 9/2004 | Haar | 422/82.05 |
| 6,790,327 B2 | 9/2004 | Ikeda | 204/403.1 |
| 6,790,599 B1 | 9/2004 | Madou | 430/320 |
| 6,792,791 B2 | 9/2004 | Sato | 73/1.02 |
| 6,793,632 B2 | 9/2004 | Sohrab | 600/573 |
| 6,793,633 B2 | 9/2004 | Douglas | 600/583 |
| 6,793,802 B2 | 9/2004 | Lee | 205/777.5 |
| 6,797,150 B2 | 9/2004 | Kermani | 205/777.5 |
| 6,800,488 B2 | 10/2004 | Khan | 436/166 |
| 6,801,041 B2 | 10/2004 | Karinka | 324/444 |
| 6,801,804 B2 | 10/2004 | Miller | 604/20 |
| 6,802,199 B2 | 10/2004 | Hilgers | 72/370.1 |
| 6,802,811 B1 | 10/2004 | Slepian | 600/309 |
| 6,802,957 B2 | 10/2004 | Jung | 205/777.5 |
| 6,805,780 B1 | 10/2004 | Ryu | 204/403.01 |
| 6,808,499 B1 | 10/2004 | Churchill | 600/587 |
| 6,808,908 B2 | 10/2004 | Yao | 435/181 |
| 6,808,937 B2 | 10/2004 | Ligler | 436/518 |
| 6,809,807 B1 | 10/2004 | Erickson | 356/213 |
| 6,811,406 B2 | 11/2004 | Grube | |
| 6,811,557 B2 | 11/2004 | Schraga | 606/182 |
| 6,811,659 B2 | 11/2004 | Vachon | 204/224 |
| 6,811,753 B2 | 11/2004 | Hirao | 422/101 |
| 6,811,792 B2 | 11/2004 | Roser | 424/423 |
| 6,812,031 B1 | 11/2004 | Carlsson | 436/52 |
| 6,814,843 B1 | 11/2004 | Bhullar | 204/403.01 |
| 6,814,844 B2 | 11/2004 | Bhullar | 204/403.1 |
| 6,814,845 B2 | 11/2004 | Wilson | 204/486 |
| 6,815,186 B2 | 11/2004 | Clark | 435/183 |
| 6,816,742 B2 | 11/2004 | Kim | 600/345 |
| 6,818,180 B2 | 11/2004 | Douglas | 422/58 |
| 6,821,483 B2 | 11/2004 | Phillips | 422/58 |
| 6,823,750 B2 | 11/2004 | Hodges | 73/864.72 |
| 6,825,047 B1 | 11/2004 | Woudenberg | 436/518 |
| 6,827,250 B2 | 12/2004 | Uhland | 228/110.1 |
| 6,827,829 B2 | 12/2004 | Kawanaka | 204/403.02 |
| 6,830,551 B1 | 12/2004 | Uchigaki | 600/584 |
| 6,830,668 B2 | 12/2004 | Musho et al. | 204/400 |
| 6,830,669 B2 | 12/2004 | Miyazaki et al. | 204/409 |
| 6,833,540 B2 | 12/2004 | MacKenzie | 250/214 |
| 6,835,184 B1 | 12/2004 | Sage | 604/46 |
| 6,835,553 B2 | 12/2004 | Han | 435/14 |
| 6,837,858 B2 | 1/2005 | Cunningham | 600/573 |
| 6,837,976 B2 | 1/2005 | Cai | 204/403.14 |
| 6,837,988 B2 | 1/2005 | Leong | 205/792 |
| 6,840,912 B2 | 1/2005 | Kloepfer | 600/583 |
| 6,841,052 B2 | 1/2005 | Musho | 204/401 |
| 6,843,254 B2 | 1/2005 | Tapper | 128/898 |
| 6,847,451 B2 | 1/2005 | Pugh | 356/436 |
| 6,849,052 B2 | 2/2005 | Uchigaki et al. | |
| 6,849,168 B2 | 2/2005 | Crumly | 204/416 |
| 6,849,216 B2 | 2/2005 | Rappin | 264/134 |
| 6,850,790 B2 | 2/2005 | Berner | 600/347 |
| 6,869,418 B2 | 3/2005 | Marano-Ford | 604/192 |
| 6,872,200 B2 | 3/2005 | Mann | 604/890.1 |
| 6,875,208 B2 | 4/2005 | Santini | 604/890.1 |
| 6,875,223 B2 | 4/2005 | Argauer | 606/181 |
| 6,875,613 B2 | 4/2005 | Shartle | 436/63 |
| 6,878,120 B2 | 4/2005 | Roe | 600/583 |
| 6,878,251 B2 | 4/2005 | Hodges | 204/403.14 |
| 6,878,255 B1 | 4/2005 | Wang | 204/452 |
| 6,878,262 B2 | 4/2005 | Taniike | 205/777.5 |
| 6,880,968 B1 | 4/2005 | Haar | 374/131 |
| 6,881,203 B2 | 4/2005 | Delmore | 604/272 |
| 6,881,322 B2 | 4/2005 | Tokunaga | 205/775 |
| 6,881,378 B1 | 4/2005 | Zimmer | 422/58 |
| 6,881,541 B2 | 4/2005 | Petersen et al. | |
| 6,881,550 B2 | 4/2005 | Phillips | 435/14 |
| 6,881,551 B2 | 4/2005 | Heller | 435/14 |
| 6,881,578 B2 | 4/2005 | Otake | 436/44 |
| 6,882,940 B2 | 4/2005 | Potts | 702/23 |
| 6,884,592 B2 | 4/2005 | Matzinger | 435/7.1 |
| 6,885,196 B2 | 4/2005 | Taniike | 324/444 |
| 6,885,883 B2 | 4/2005 | Parris | 600/347 |
| 6,887,239 B2 | 5/2005 | Elstrom | 606/41 |
| 6,887,253 B2 | 5/2005 | Curie | 606/181 |
| 6,887,426 B2 | 5/2005 | Phillips | 422/56 |
| 6,887,709 B2 | 5/2005 | Leong | 436/8 |
| 6,889,069 B2 | 5/2005 | Routt | 600/319 |
| 6,890,319 B1 | 5/2005 | Crocker | 604/131 |
| 6,890,421 B2 | 5/2005 | Ohara | 205/777.5 |
| 6,890,484 B2 | 5/2005 | Bautista | 422/58 |
| 6,891,936 B2 | 5/2005 | Kai | 379/106.02 |
| 6,892,085 B2 | 5/2005 | McIvor | 600/347 |
| 6,893,396 B2 | 5/2005 | Schulze | 600/300 |
| 6,893,545 B2 | 5/2005 | Gotoh | 204/403.5 |
| 6,893,552 B1 | 5/2005 | Wang | 205/777.5 |
| 6,895,263 B2 | 5/2005 | Shin | 600/316 |
| 6,895,264 B2 | 5/2005 | Rice | 600/319 |
| 6,895,265 B2 | 5/2005 | Silver | 600/345 |
| 6,896,793 B2 | 5/2005 | Erdosy | 205/775 |
| 6,897,788 B2 | 5/2005 | Khair | 340/870.16 |
| 6,902,905 B2 | 6/2005 | Burson | 435/14 |
| 6,904,301 B2 | 6/2005 | Raskas | 600/310 |
| 6,905,733 B2 | 6/2005 | Russel | 427/393.5 |
| 6,908,008 B2 | 6/2005 | Pugh | 221/135 |
| 6,908,535 B2 | 6/2005 | Rankin | 204/406 |
| 6,908,591 B2 | 6/2005 | MacPhee | 422/22 |
| 6,908,593 B1 | 6/2005 | Shartle | 422/58 |
| 6,911,130 B2 | 6/2005 | Brenneman | 204/400 |
| 6,911,131 B2 | 6/2005 | Miyazaki | 204/403.14 |
| 6,911,621 B2 | 6/2005 | Bhullar | 219/121.69 |
| 6,916,410 B2 | 7/2005 | Katsuki | 204/403 |
| 6,918,901 B1 | 7/2005 | Theeuwes et al. | |
| 6,918,918 B1 | 7/2005 | Schraga | 606/182 |

| Patent No. | Date | Name | Class |
|---|---|---|---|
| 6,922,576 B2 | 7/2005 | Raskas | 600/316 |
| 6,922,578 B2 | 7/2005 | Eppstein | 600/347 |
| 6,923,764 B2 | 8/2005 | Aceti | 600/309 |
| 6,923,894 B2 | 8/2005 | Huang | 204/403.06 |
| 6,923,936 B2 | 8/2005 | Swanson | 422/22 |
| 6,924,093 B2 | 8/2005 | Haviland | 435/4 |
| 6,925,317 B1 | 8/2005 | Samuels | 600/344 |
| 6,925,393 B1 | 8/2005 | Kalatz | 702/27 |
| 6,929,649 B2 | 8/2005 | Pugh | 606/182 |
| 6,929,650 B2 | 8/2005 | Fukuzawa | 606/182 |
| 6,931,327 B2 | 8/2005 | Goode | 702/22 |
| 6,931,328 B2 | 8/2005 | Braig | 702/23 |
| 6,939,310 B2 | 9/2005 | Matzinger | 600/573 |
| 6,939,312 B2 | 9/2005 | Hodges | 600/583 |
| 6,939,450 B2 | 9/2005 | Karinka | 204/409 |
| 6,940,591 B2 | 9/2005 | Sopp | 356/244 |
| 6,942,518 B2 | 9/2005 | Liamos | 439/495 |
| 6,942,769 B2 | 9/2005 | Cheng | 204/400 |
| 6,942,770 B2 | 9/2005 | Cai | 204/403.04 |
| 6,944,486 B2 | 9/2005 | Braig | 600/310 |
| 6,945,943 B2 | 9/2005 | Pugh | 600/584 |
| 6,946,067 B2 | 9/2005 | Hodges | 205/792 |
| 6,946,098 B2 | 9/2005 | Miekka | 422/22 |
| 6,946,299 B2 | 9/2005 | Neel | 436/95 |
| 6,949,111 B2 | 9/2005 | Schraga | 606/182 |
| 6,949,221 B2 | 9/2005 | Kiser | 422/56 |
| 6,951,631 B1 | 10/2005 | Catt | 422/56 |
| 6,951,728 B2 | 10/2005 | Qian | 435/14 |
| 6,952,603 B2 | 10/2005 | Gerber | 600/310 |
| 6,952,604 B2 | 10/2005 | DeNuzzio | 600/345 |
| 6,952,693 B2 | 10/2005 | Neel | 436/149 |
| 6,954,662 B2 | 10/2005 | Freger | 600/316 |
| 6,958,072 B2 | 10/2005 | Schraga | 606/182 |
| 6,958,129 B2 | 10/2005 | Galen | 422/57 |
| 6,958,809 B2 | 10/2005 | Sterling | 356/39 |
| 6,959,211 B2 | 10/2005 | Rule | 600/310 |
| 6,959,247 B2 | 10/2005 | Neel | 702/19 |
| 6,960,287 B2 | 11/2005 | Charlton | 205/775 |
| 6,960,289 B2 | 11/2005 | Hodges | 205/778 |
| 6,964,871 B2 | 11/2005 | Bell | 436/95 |
| 6,965,791 B1 | 11/2005 | Hitchcock | 600/345 |
| 6,966,880 B2 | 11/2005 | Boecker | 600/583 |
| 6,966,977 B2 | 11/2005 | Hasegawa | 204/403.07 |
| 6,967,105 B2 | 11/2005 | Nomura | 436/169 |
| 6,968,375 B1 | 11/2005 | Brown | 709/224 |
| 6,969,359 B2 | 11/2005 | Duchon | 600/583 |
| 6,969,450 B2 | 11/2005 | Taniike | 204/403.01 |
| 6,969,451 B2 | 11/2005 | Shin | 204/412 |
| 6,973,706 B2 | 12/2005 | Say | 29/595 |
| 6,975,893 B2 | 12/2005 | Say | 600/347 |
| 6,977,032 B2 | 12/2005 | Hasegawa | 204/403.05 |
| 6,979,544 B2 | 12/2005 | Keen | 435/6 |
| 6,979,571 B2 | 12/2005 | Modzelewski | 436/164 |
| 6,982,027 B2 | 1/2006 | Yagi | 204/403.06 |
| 6,982,431 B2 | 1/2006 | Modlin et al. | |
| 6,983,176 B2 | 1/2006 | Gardner | 600/310 |
| 6,983,177 B2 | 1/2006 | Rule | 600/310 |
| 6,984,307 B2 | 1/2006 | Zweig | 205/777.5 |
| 6,986,777 B2 | 1/2006 | Kim | 606/182 |
| 6,986,869 B2 | 1/2006 | Tuohy | 422/56 |
| 6,988,996 B2 | 1/2006 | Roe | 600/584 |
| 6,989,243 B2 | 1/2006 | Yani | 435/14 |
| 6,989,891 B2 | 1/2006 | Braig | 356/39 |
| 6,990,365 B1 | 1/2006 | Parker | 600/328 |
| 6,990,366 B2 | 1/2006 | Say | 600/345 |
| 6,990,367 B2 | 1/2006 | Kiser | 600/345 |
| 6,990,849 B2 | 1/2006 | Bohm | 73/53.01 |
| 6,991,918 B2 | 1/2006 | Keith | 435/31 |
| 6,991,940 B2 | 1/2006 | Carroll | 436/514 |
| 6,994,825 B2 | 2/2006 | Haviland | 422/58 |
| 6,997,317 B2 | 2/2006 | Catelli | 206/438 |
| 6,997,343 B2 | 2/2006 | May | 221/232 |
| 6,997,344 B2 | 2/2006 | Brown | 221/258 |
| 6,997,936 B2 | 2/2006 | Marshall | 606/181 |
| 6,998,247 B2 | 2/2006 | Monfre | 435/14 |
| 6,998,248 B2 | 2/2006 | Yani | 435/14 |
| 6,999,810 B2 | 2/2006 | Berner | 600/345 |
| 7,001,343 B2 | 2/2006 | Erickson | 600/573 |
| 7,001,344 B2 | 2/2006 | Freeman | 600/583 |
| 7,003,337 B2 | 2/2006 | Harjunmaa | 600/316 |
| 7,003,340 B2 | 2/2006 | Say | 600/345 |
| 7,003,341 B2 | 2/2006 | Say | 600/345 |
| 7,004,928 B2 | 2/2006 | Aceti | 604/191 |
| 7,005,048 B1 | 2/2006 | Watanabe | 204/403.04 |
| 7,005,273 B2 | 2/2006 | Heller | 435/25 |
| 7,005,459 B2 | 2/2006 | Hekal | 523/102 |
| 7,005,857 B2 | 2/2006 | Stiene | 324/449 |
| 7,006,857 B2 | 2/2006 | Braig | 600/310 |
| 7,006,858 B2 | 2/2006 | Silver | 600/345 |
| 7,008,384 B2 | 3/2006 | Tapper | 600/573 |
| 7,010,432 B2 | 3/2006 | Kermani | 702/19 |
| 7,011,630 B2 | 3/2006 | Desai | 600/309 |
| 7,011,954 B2 | 3/2006 | Ouyang | 435/7.9 |
| 7,014,615 B2 | 3/2006 | Erickson | 600/573 |
| 7,015,262 B2 | 3/2006 | Leong | 523/205 |
| 7,016,713 B2 | 3/2006 | Gardner | 600/310 |
| 7,018,568 B2 | 3/2006 | Tierney | 252/511 |
| 7,018,848 B2 | 3/2006 | Douglas | 436/524 |
| 7,022,217 B2 | 4/2006 | Hodges | 205/777.5 |
| 7,022,218 B2 | 4/2006 | Taniike | 205/777.5 |
| 7,022,286 B2 | 4/2006 | Lemke | 422/67 |
| 7,024,236 B2 | 4/2006 | Ford | 600/345 |
| 7,024,248 B2 | 4/2006 | Penner | 607/60 |
| 7,024,399 B2 | 4/2006 | Sumner | 706/45 |
| 7,025,425 B2 | 4/2006 | Kovatchev | 300/365 |
| 7,025,774 B2 | 4/2006 | Freeman | 606/181 |
| 7,027,848 B2 | 4/2006 | Robinson | 600/310 |
| 7,029,444 B2 | 4/2006 | Shin | 600/365 |
| 7,033,322 B2 | 4/2006 | Silver | 600/486 |
| 7,033,371 B2 | 4/2006 | Alden | 606/181 |
| 7,039,560 B2 | 5/2006 | Kawatahara | 702/187 |
| 7,041,057 B1 | 5/2006 | Faupel | 600/365 |
| 7,041,063 B2 | 5/2006 | Abreu | 600/549 |
| 7,041,068 B2 | 5/2006 | Freeman | 600/583 |
| 7,041,254 B2 | 5/2006 | Haviland | 422/58 |
| 7,041,468 B2 | 5/2006 | Drucker | 435/14 |
| 7,043,287 B1 | 5/2006 | Khalil | 600/310 |
| 7,044,911 B2 | 5/2006 | Drinan | 600/300 |
| 7,045,054 B1 | 5/2006 | Buck | 205/778 |
| 7,045,097 B2 | 5/2006 | Kovacs | 422/82.08 |
| 7,045,310 B2 | 5/2006 | Buck | 435/7.93 |
| 7,045,361 B2 | 5/2006 | Heiss | 436/172 |
| 7,047,070 B2 | 5/2006 | Wilkinson | 604/20 |
| 7,047,795 B2 | 5/2006 | Sato | 73/64.56 |
| 7,049,130 B2 | 5/2006 | Carroll | 435/287.2 |
| 7,050,843 B2 | 5/2006 | Shartle | 600/345 |
| 7,051,495 B2 | 5/2006 | Lang | 53/475 |
| 7,052,268 B2 | 5/2006 | Powell | 425/542 |
| 7,052,591 B2 | 5/2006 | Gao | 204/490 |
| 7,052,652 B2 | 5/2006 | Zanzucchi | 422/82.05 |
| 7,052,864 B2 | 5/2006 | Durkop | 435/25 |
| 7,054,682 B2 | 5/2006 | Young | 604/20 |
| 7,054,759 B2 | 5/2006 | Fukunaga | 702/23 |
| D523,555 S | | Loerwald | D24/146 |
| 7,056,425 B2 | 6/2006 | Hasegawa | 204/403.04 |
| 7,056,495 B2 | 6/2006 | Roser | 424/45 |
| 7,058,437 B2 | 6/2006 | Buse | 600/347 |
| 7,060,059 B2 | 6/2006 | Keith | 604/504 |
| 7,060,192 B2 | 6/2006 | Yuzhakov | 216/11 |
| 7,061,593 B2 | 6/2006 | Braig | 356/39 |
| 7,063,234 B2 | 6/2006 | Giraud | 221/271 |
| 7,063,774 B2 | 6/2006 | Bhullar | 204/403.02 |
| 7,063,775 B2 | 6/2006 | Yamaoka | 204/403.06 |
| 7,063,776 B2 | 6/2006 | Huang | 204/403.14 |
| 7,066,884 B2 | 6/2006 | Custer | 600/309 |
| 7,066,885 B2 | 6/2006 | Erickson | 600/309 |

| Patent No. | Date | Name | Class |
|---|---|---|---|
| 7,070,564 B2 | 7/2006 | Matzinger | 600/300 |
| 7,070,680 B2 | 7/2006 | Bae | 204/403.04 |
| 7,073,246 B2 | 7/2006 | Bhullar | 29/595 |
| 7,074,307 B2 | 7/2006 | Simpson | 204/403.04 |
| 7,074,308 B2 | 7/2006 | Mao | 204/403.14 |
| 7,077,328 B2 | 7/2006 | Krishnaswamy | 235/472.01 |
| 7,077,828 B2 | 7/2006 | Kuhr | 604/207 |
| 7,078,480 B2 | 7/2006 | Nagel | 530/322 |
| 7,081,188 B1 | 7/2006 | Cho | 204/403.04 |
| 7,083,712 B2 | 8/2006 | Morita | 205/775 |
| 7,086,277 B2 | 8/2006 | Tess | 73/53.01 |
| 7,087,149 B1 | 8/2006 | Muguruma | 205/778 |
| 7,090,764 B2 | 8/2006 | Iyengar | 205/775 |
| 7,096,053 B2 | 8/2006 | Loeb | 600/317 |
| 7,096,124 B2 | 8/2006 | Sterling | 702/23 |
| 7,097,631 B2 | 8/2006 | Trautman | 604/46 |
| 7,098,038 B2 | 8/2006 | Fukuoka | 436/164 |
| 7,103,578 B2 | 9/2006 | Beck | 705/75 |
| 7,105,066 B2 | 9/2006 | Schraga | 600/182 |
| 7,107,253 B1 | 9/2006 | Sumner | 706/45 |
| 7,108,680 B2 | 9/2006 | Rohr | 604/151 |
| 7,108,778 B2 | 9/2006 | Simpson | 205/778 |
| 7,109,271 B2 | 9/2006 | Liu | 525/382 |
| 7,110,112 B2 | 9/2006 | Uchida | 356/364 |
| 7,110,803 B2 | 9/2006 | Shults | 600/347 |
| 7,112,265 B1 | 9/2006 | McAleer | 204/403.09 |
| 7,112,451 B2 | 9/2006 | Takahashi | 436/514 |
| 7,115,362 B2 | 10/2006 | Douglas | 435/4 |
| 7,118,351 B2 | 10/2006 | Effenhauser | 417/208 |
| 7,118,667 B2 | 10/2006 | Lee | 205/777.5 |
| 7,118,668 B1 | 10/2006 | Edelbrock | 205/777.5 |
| 7,118,916 B2 | 10/2006 | Matzinger | 436/34 |
| 7,118,919 B2 | 10/2006 | Yatscoff | 436/56 |
| 7,120,483 B2 | 10/2006 | Russell | 600/345 |
| 7,122,102 B2 | 10/2006 | Wogoman | 204/400 |
| 7,122,110 B2 | 10/2006 | Deng | 205/777.5 |
| 7,122,111 B2 | 10/2006 | Tokunaga | 205/792 |
| 7,125,481 B2 | 10/2006 | Musho | 205/775 |
| 7,129,038 B2 | 10/2006 | Gopalan | 435/4 |
| RE39,390 E | 11/2006 | Hasegawa | 204/403.09 |
| D531,725 S | 11/2006 | Loerwald | D24/146 |
| 7,131,342 B2 | 11/2006 | Hodges | 73/864.72 |
| 7,131,984 B2 | 11/2006 | Sato | 606/182 |
| 7,132,041 B2 | 11/2006 | Deng | 205/777.5 |
| 7,133,710 B2 | 11/2006 | Acosta | 600/316 |
| 7,134,999 B2 | 11/2006 | Brauker | 600/309 |
| 7,135,100 B1 | 11/2006 | Lau | 204/403.14 |
| 7,137,957 B2 | 11/2006 | Erickson | 600/573 |
| 7,138,041 B2 | 11/2006 | Su | 204/403.04 |
| 7,138,089 B2 | 11/2006 | Aitken | 422/82.01 |
| 7,141,058 B2 | 11/2006 | Briggs | 606/181 |
| 7,144,404 B2 | 12/2006 | Whitson | 606/181 |
| 7,144,485 B2 | 12/2006 | Hsu | 204/403.02 |
| 7,144,495 B2 | 12/2006 | Teodorezyk | 205/792 |
| 7,144,496 B2 | 12/2006 | Meserol | 205/792 |
| 7,147,825 B2 | 12/2006 | Matsuda | 422/58 |
| 7,150,755 B2 | 12/2006 | Levaughn | 606/181 |
| 7,150,975 B2 | 12/2006 | Tamada | 435/14 |
| 7,150,995 B2 | 12/2006 | Xie | 436/67 |
| 7,153,696 B2 | 12/2006 | Fukuoka | 436/164 |
| 7,155,371 B2 | 12/2006 | Kawatahara | 702/187 |
| 7,160,251 B2 | 1/2007 | Neel | 600/365 |
| 7,160,313 B2 | 1/2007 | Galloway | 606/167 |
| 7,160,678 B1 | 1/2007 | Kayyem et al. | |
| 7,163,616 B2 | 1/2007 | Vreeke | 205/777.5 |
| 7,166,074 B2 | 1/2007 | Reghabi | 600/365 |
| 7,167,734 B2 | 1/2007 | Khalil | 600/310 |
| 7,167,818 B2 | 1/2007 | Brown | 703/11 |
| 7,225,535 B2 | 6/2007 | Feldman et al. | |
| 7,226,461 B2 | 6/2007 | Boecker et al. | |
| 7,331,931 B2 * | 2/2008 | Freeman et al. | 600/583 |
| 7,481,776 B2 * | 1/2009 | Boecker et al. | 600/583 |
| 7,491,178 B2 * | 2/2009 | Boecker et al. | 600/583 |
| 2001/0011157 A1 | 8/2001 | Latterell | 600/576 |
| 2001/0016682 A1 | 8/2001 | Berner | 600/345 |
| 2001/0017269 A1 | 8/2001 | Heller | 205/777.5 |
| 2001/0027328 A1 | 10/2001 | Lum | 606/186 |
| 2001/0054319 A1 | 12/2001 | Heller | 73/849 |
| 2002/0016606 A1 | 2/2002 | Moerman | 606/181 |
| 2002/0019748 A1 | 2/2002 | Brown | 705/2 |
| 2002/0025469 A1 | 2/2002 | Heller | 429/43 |
| 2002/0029058 A1 | 3/2002 | Levaughn | 606/181 |
| 2002/0040230 A1 | 4/2002 | Kuhr | 606/181 |
| 2002/0042090 A1 | 4/2002 | Heller | 435/14 |
| 2002/0042594 A1 | 4/2002 | Lum | |
| 2002/0044890 A1 | 4/2002 | Black | 422/56 |
| 2002/0052618 A1 | 5/2002 | Haar et al. | |
| 2002/0053523 A1 | 5/2002 | Liamos | 205/787 |
| 2002/0057993 A1 | 5/2002 | Maisey | 422/82.01 |
| 2002/0076349 A1 | 6/2002 | Aitken | 422/58 |
| 2002/0078091 A1 | 6/2002 | Vu | 707/513 |
| 2002/0081559 A1 | 6/2002 | Brown | 434/307 R |
| 2002/0081588 A1 | 6/2002 | Lumley-Woodyear | 435/6 |
| 2002/0084196 A1 | 7/2002 | Liamos | 205/792 |
| 2002/0087056 A1 | 7/2002 | Aceti | |
| 2002/0092612 A1 | 7/2002 | Davies | 156/292 |
| 2002/0099308 A1 | 7/2002 | Bojan et al. | |
| 2002/0120216 A1 | 8/2002 | Fritz | 600/583 |
| 2002/0120261 A1 | 8/2002 | Morris | 606/41 |
| 2002/0130042 A1 | 9/2002 | Moerman | 204/403.01 |
| 2002/0133377 A1 | 9/2002 | Brown | 705/3 |
| 2002/0136667 A1 | 9/2002 | Subramanian | 422/100 |
| 2002/0136863 A1 | 9/2002 | Subramanian | 428/156 |
| 2002/0137998 A1 | 9/2002 | Smart | 600/347 |
| 2002/0138040 A1 | 9/2002 | Flora | 604/116 |
| 2002/0148739 A2 | 10/2002 | Liamos | 205/787 |
| 2002/0160520 A1 | 10/2002 | Orloff | 436/72 |
| 2002/0161289 A1 | 10/2002 | Hopkins | 600/322 |
| 2002/0168290 A1 | 11/2002 | Yuzhakov | 422/56 |
| 2002/0176984 A1 | 11/2002 | Smart | 428/336 |
| 2002/0177761 A1 | 11/2002 | Orloff | 600/309 |
| 2002/0188224 A1 | 12/2002 | Roe | 600/584 |
| 2003/0018282 A1 | 1/2003 | Effenhauser | 600/583 |
| 2003/0018300 A1 | 1/2003 | Duchon | 604/164.01 |
| 2003/0028125 A1 | 2/2003 | Yuzhakov | |
| 2003/0028126 A1 | 2/2003 | List | 600/583 |
| 2003/0050537 A1 | 3/2003 | Wessel | 600/300 |
| 2003/0050573 A1 | 3/2003 | Kuhr | 600/567 |
| 2003/0050656 A1 | 3/2003 | Schraga | 606/182 |
| 2003/0060730 A1 | 3/2003 | Perez | 606/182 |
| 2003/0069753 A1 | 4/2003 | Brown | 705/2 |
| 2003/0073089 A1 | 4/2003 | Mauze | 435/6 |
| 2003/0073229 A1 | 4/2003 | Greenstein | 435/287.2 |
| 2003/0073931 A1 | 4/2003 | Boecker et al. | |
| 2003/0083685 A1 | 5/2003 | Freeman | 606/181 |
| 2003/0083686 A1 | 5/2003 | Freeman | 606/181 |
| 2003/0088160 A1 | 5/2003 | Halleck | 600/300 |
| 2003/0088191 A1 | 5/2003 | Freeman et al. | 600/583 |
| 2003/0089730 A1 | 5/2003 | May | 221/232 |
| 2003/0093010 A1 | 5/2003 | Essenpreis | 600/583 |
| 2003/0100040 A1 | 5/2003 | Bonnecaze | 435/14 |
| 2003/0106810 A1 | 6/2003 | Douglas | 205/777.5 |
| 2003/0109777 A1 | 6/2003 | Kloepfer | 600/367 |
| 2003/0109860 A1 | 6/2003 | Black | |
| 2003/0111357 A1 | 6/2003 | Black | 205/775 |
| 2003/0113827 A1 | 6/2003 | Burkoth | 435/14 |
| 2003/0116447 A1 | 6/2003 | Sturridge | 205/777.5 |
| 2003/0135333 A1 | 7/2003 | Aceti | 702/31 |
| 2003/0136189 A1 | 7/2003 | Lauman et al. | |
| 2003/0139653 A1 | 7/2003 | Manser | 600/300 |
| 2003/0143113 A2 | 7/2003 | Yuzhakov | 422/56 |
| 2003/0144608 A1 | 7/2003 | Kojima | 600/583 |
| 2003/0144609 A1 | 7/2003 | Kennedy | 600/583 |
| 2003/0146110 A1 | 8/2003 | Karinka | 205/777.5 |
| 2003/0149348 A1 | 8/2003 | Raskas | 600/310 |
| 2003/0149377 A1 | 8/2003 | Erickson | 600/573 |

| Publication No. | Date | Name | Citation |
|---|---|---|---|
| 2003/0153900 A1 | 8/2003 | Aceti | 604/890.1 |
| 2003/0159944 A1 | 8/2003 | Pottgen | 205/777.5 |
| 2003/0163351 A1 | 8/2003 | Brown | 705/2 |
| 2003/0178322 A1 | 9/2003 | Iyengar | 205/775 |
| 2003/0191415 A1 | 10/2003 | Moerman | 600/584 |
| 2003/0195435 A1 | 10/2003 | Williams | 600/583 |
| 2003/0195540 A1 | 10/2003 | Moerman | 606/181 |
| 2003/0199744 A1 | 10/2003 | Buse | 600/347 |
| 2003/0199789 A1 | 10/2003 | Boecker | 600/575 |
| 2003/0199790 A1 | 10/2003 | Boecker | 600/576 |
| 2003/0199791 A1 | 10/2003 | Boecker | 600/576 |
| 2003/0199891 A1 | 10/2003 | Argauer | 606/181 |
| 2003/0199893 A1 | 10/2003 | Boecker | 606/181 |
| 2003/0199894 A1 | 10/2003 | Boecker | 606/181 |
| 2003/0199895 A1 | 10/2003 | Boecker | 606/181 |
| 2003/0199896 A1 | 10/2003 | Boecker | 606/181 |
| 2003/0199897 A1 | 10/2003 | Boecker | 606/181 |
| 2003/0199898 A1 | 10/2003 | Boecker | 606/181 |
| 2003/0199899 A1 | 10/2003 | Boecker | 606/181 |
| 2003/0199900 A1 | 10/2003 | Boecker | 606/181 |
| 2003/0199901 A1 | 10/2003 | Boecker | 606/181 |
| 2003/0199902 A1 | 10/2003 | Boecker | 606/181 |
| 2003/0199903 A1 | 10/2003 | Boecker | 606/181 |
| 2003/0199904 A1 | 10/2003 | Boecker | 606/181 |
| 2003/0199905 A1 | 10/2003 | Boecker | 606/181 |
| 2003/0199906 A1 | 10/2003 | Boecker | 606/181 |
| 2003/0199907 A1 | 10/2003 | Boecker | 606/181 |
| 2003/0199908 A1 | 10/2003 | Boecker | 606/181 |
| 2003/0199909 A1 | 10/2003 | Boecker | 606/181 |
| 2003/0199910 A1 | 10/2003 | Boecker | 606/181 |
| 2003/0199911 A1 | 10/2003 | Boecker | 606/181 |
| 2003/0199912 A1 | 10/2003 | Pugh | 606/182 |
| 2003/0201194 A1 | 10/2003 | Heller | 205/777.5 |
| 2003/0203352 A1 | 10/2003 | Haviland | 435/4 |
| 2003/0206828 A1 | 11/2003 | Bell | 422/44 |
| 2003/0208140 A1 | 11/2003 | Pugh | 600/584 |
| 2003/0212344 A1 | 11/2003 | Yuzhakov | 600/583 |
| 2003/0212345 A1 | 11/2003 | McAllister | 600/584 |
| 2003/0212346 A1 | 11/2003 | Yuzhakov et al. | 600/584 |
| 2003/0212347 A1 | 11/2003 | Sohrab | 600/584 |
| 2003/0212423 A1 | 11/2003 | Pugh | 606/181 |
| 2003/0212424 A1 | 11/2003 | Briggs | 606/181 |
| 2003/0212579 A1 | 11/2003 | Brown | 705/2 |
| 2003/0216767 A1 | 11/2003 | List | 606/181 |
| 2003/0217918 A1 | 11/2003 | Davies | 204/403.14 |
| 2003/0220552 A1 | 11/2003 | Reghabi | 600/365 |
| 2003/0220663 A1 | 11/2003 | Fletcher | 606/182 |
| 2003/0223906 A1 | 12/2003 | McAllister | 422/58 |
| 2003/0225317 A1 | 12/2003 | Schell | 600/300 |
| 2003/0225429 A1 | 12/2003 | Garthe | 606/182 |
| 2003/0225430 A1 | 12/2003 | Schraga | 606/182 |
| 2003/0228637 A1 | 12/2003 | Wang | 435/7.9 |
| 2003/0229514 A2 | 12/2003 | Brown | 705/2 |
| 2003/0232370 A1 | 12/2003 | Trifiro | 435/6 |
| 2003/0233055 A1 | 12/2003 | Erickson | 600/573 |
| 2003/0233112 A1 | 12/2003 | Alden et al. | 606/181 |
| 2003/0233113 A1 | 12/2003 | Alden et al. | 606/182 |
| 2004/0006285 A1 | 1/2004 | Douglas | 600/583 |
| 2004/0007585 A1 | 1/2004 | Griffith | 221/232 |
| 2004/0009100 A1 | 1/2004 | Simons | 422/102 |
| 2004/0010279 A1 | 1/2004 | Freeman | 606/182 |
| 2004/0015064 A1 | 1/2004 | Parsons | 600/347 |
| 2004/0019250 A1 | 1/2004 | Catelli | 600/1 |
| 2004/0019259 A1 | 1/2004 | Brown | 600/300 |
| 2004/0026243 A1 | 2/2004 | Davies | 204/403.14 |
| 2004/0030353 A1 | 2/2004 | Schmelzeisen-R | 606/201 |
| 2004/0031682 A1 | 2/2004 | Wilsey | 204/403.1 |
| 2004/0034318 A1 | 2/2004 | Fritz | 604/19 |
| 2004/0038045 A1 | 2/2004 | Smart et al. | 428/446 |
| 2004/0039303 A1 | 2/2004 | Wurster | 600/584 |
| 2004/0039342 A1 | 2/2004 | Eppstein | 604/200 |
| 2004/0039407 A1 | 2/2004 | Schraga | 606/181 |
| 2004/0039408 A1 | 2/2004 | Abulhaj | 606/181 |
| 2004/0049219 A1 | 3/2004 | Briggs | 606/181 |
| 2004/0049220 A1 | 3/2004 | Boecker | 606/181 |
| 2004/0050694 A1 | 3/2004 | Yang | 204/403.02 |
| 2004/0054267 A1 | 3/2004 | Feldman | 600/316 |
| 2004/0055898 A1 | 3/2004 | Heller et al. | 205/777.5 |
| 2004/0059256 A1 | 3/2004 | Perez | 600/583 |
| 2004/0060818 A1 | 4/2004 | Feldman | 204/403.01 |
| 2004/0061841 A1 | 4/2004 | Black | 355/30 |
| 2004/0064068 A1 | 4/2004 | DeNuzzio | 600/583 |
| 2004/0087990 A1 | 5/2004 | Boecker et al. | 606/181 |
| 2004/0092842 A1 | 5/2004 | Boecker | 600/575 |
| 2004/0092994 A1 | 5/2004 | Briggs | 606/181 |
| 2004/0092995 A1 | 5/2004 | Boecker | 606/181 |
| 2004/0096991 A1 | 5/2004 | Zhang | 436/518 |
| 2004/0098009 A1 | 5/2004 | Boecker | 606/181 |
| 2004/0098010 A1 | 5/2004 | Davison | 606/181 |
| 2004/0102803 A1 | 5/2004 | Boecker | 606/183 |
| 2004/0106855 A1 | 6/2004 | Brown | 600/301 |
| 2004/0106858 A1 | 6/2004 | Say | 600/345 |
| 2004/0106859 A1 | 6/2004 | Say | 600/345 |
| 2004/0106860 A1 | 6/2004 | Say | 600/345 |
| 2004/0106904 A1 | 6/2004 | Gonnelli | 604/173 |
| 2004/0106941 A1 | 6/2004 | Roe | 606/181 |
| 2004/0107116 A1 | 6/2004 | Brown | 705/2 |
| 2004/0115754 A1 | 6/2004 | Chang | 435/14 |
| 2004/0115831 A1 | 6/2004 | Meathrel | 436/514 |
| 2004/0116780 A1 | 6/2004 | Brown | 600/300 |
| 2004/0116829 A1 | 6/2004 | Raney | 600/573 |
| 2004/0117207 A1 | 6/2004 | Brown | 705/2 |
| 2004/0117208 A1 | 6/2004 | Brown | 705/2 |
| 2004/0117209 A1 | 6/2004 | Brown | 705/2 |
| 2004/0117210 A1 | 6/2004 | Brown | 705/2 |
| 2004/0122339 A1 | 6/2004 | Roe | |
| 2004/0127818 A1 | 7/2004 | Roe | 600/583 |
| 2004/0127819 A1 | 7/2004 | Roe | 600/583 |
| 2004/0127928 A1 | 7/2004 | Whitson | 606/181 |
| 2004/0127929 A1 | 7/2004 | Roe | 606/181 |
| 2004/0132167 A1 | 7/2004 | Rule | 435/287.1 |
| 2004/0133125 A1 | 7/2004 | Miyashita | 600/573 |
| 2004/0133127 A1 | 7/2004 | Roe | 600/583 |
| 2004/0137640 A1 | 7/2004 | Hirao | 436/514 |
| 2004/0138541 A1 | 7/2004 | Ward | 600/345 |
| 2004/0138588 A1 | 7/2004 | Saikley | 600/583 |
| 2004/0138688 A1 | 7/2004 | Giraud | 606/181 |
| 2004/0146958 A1 | 7/2004 | Bae | 435/14 |
| 2004/0154932 A1 | 8/2004 | Deng | 205/777.5 |
| 2004/0157017 A1 | 8/2004 | Mauze | 428/35.7 |
| 2004/0157149 A1 | 8/2004 | Hofmann | 430/131 |
| 2004/0157319 A1 | 8/2004 | Keen | 435/287.2 |
| 2004/0157338 A1 | 8/2004 | Burke | 436/147 |
| 2004/0157339 A1 | 8/2004 | Burke | 436/149 |
| 2004/0158137 A1 | 8/2004 | Eppstein | 600/347 |
| 2004/0158271 A1 | 8/2004 | Hamamoto | 606/181 |
| 2004/0161737 A1 | 8/2004 | Yang | 435/5 |
| 2004/0162473 A1 | 8/2004 | Sohrab | 600/345 |
| 2004/0162474 A1 | 8/2004 | Kiser | 600/345 |
| 2004/0162506 A1 | 8/2004 | Duchon et al. | 600/583 |
| 2004/0162573 A1 | 8/2004 | Keheiri | 606/182 |
| 2004/0167383 A1 | 8/2004 | Kim | 600/365 |
| 2004/0171057 A1 | 9/2004 | Mauze et al. | 435/6 |
| 2004/0171968 A1 | 9/2004 | Katsuki | 600/583 |
| 2004/0172000 A1 | 9/2004 | Roe | 604/361 |
| 2004/0173472 A1 | 9/2004 | Jung | 205/777.5 |
| 2004/0173488 A1 | 9/2004 | Griffin | 206/363 |
| 2004/0176705 A1 | 9/2004 | Stevens | 600/584 |
| 2004/0176732 A1 | 9/2004 | Frazier | 604/345 |
| 2004/0178066 A1 | 9/2004 | Miyazaki | 204/403.01 |
| 2004/0178067 A1 | 9/2004 | Miyazaki | 204/403.1 |
| 2004/0178216 A1 | 9/2004 | Brickwood | 221/268 |
| 2004/0180379 A1 | 9/2004 | van Duyne | 435/7.1 |
| 2004/0182703 A1 | 9/2004 | Bell | 204/403.11 |
| 2004/0185568 A1 | 9/2004 | Matsumoto | 436/8 |
| 2004/0186359 A1 | 9/2004 | Beaudoin | 600/310 |

| | | | | | | |
|---|---|---|---|---|---|---|
| 2004/0186394 A1 | 9/2004 | Roe ............ 600/598 | | 2004/0267160 A9 | 12/2004 | Perez ............ 600/583 |
| 2004/0186500 A1 | 9/2004 | Koike ............ 606/181 | | 2004/0267229 A1 | 12/2004 | Moerman ............ 604/500 |
| 2004/0193201 A1 | 9/2004 | Kim ............ 606/181 | | 2004/0267299 A1 | 12/2004 | Kuriger ............ 606/181 |
| 2004/0193377 A1 | 9/2004 | Brown ............ 702/19 | | 2004/0267300 A1 | 12/2004 | Mace ............ 606/182 |
| 2004/0194302 A1 | 10/2004 | Bhullar ............ 29/847 | | 2005/0000806 A1 | 1/2005 | Hsieh ............ 203/403.1 |
| 2004/0197231 A1 | 10/2004 | Katsuki ............ 422/68.1 | | 2005/0000807 A1 | 1/2005 | Wang ............ 204/403.81 |
| 2004/0197821 A1 | 10/2004 | Bauer ............ 437/7.1 | | 2005/0000808 A1 | 1/2005 | Cui ............ 203/403.14 |
| 2004/0199062 A1 | 10/2004 | Petersson ............ 600/316 | | 2005/0003470 A1 | 1/2005 | Nelson ............ 435/14 |
| 2004/0199409 A1 | 10/2004 | Brown ............ 705/3 | | 2005/0004437 A1 | 1/2005 | Kaufmann ............ 600/300 |
| 2004/0200720 A1 | 10/2004 | Musho ............ 204/403.01 | | 2005/0004494 A1 | 1/2005 | Perez ............ 600/583 |
| 2004/0200721 A1 | 10/2004 | Bhullar ............ 204/403.01 | | 2005/0008537 A1 | 1/2005 | Mosolu ............ 422/56 |
| 2004/0202576 A1 | 10/2004 | Aceti ............ 422/82.05 | | 2005/0008851 A1 | 1/2005 | Ezoe ............ 428/336 |
| 2004/0204662 A1 | 10/2004 | Perez ............ 600/583 | | 2005/0009191 A1 | 1/2005 | Swenson ............ 436/43 |
| 2004/0206625 A1 | 10/2004 | Bhullar ............ 204/403.1 | | 2005/0010090 A1 | 1/2005 | Acosta ............ 600/316 |
| 2004/0206636 A1 | 10/2004 | Hodges ............ 205/792 | | 2005/0010093 A1 | 1/2005 | Ford ............ 600/345 |
| 2004/0206658 A1 | 10/2004 | Hammerstedt ............ 206/524.1 | | 2005/0010134 A1 | 1/2005 | Douglas ............ 600/573 |
| 2004/0209307 A1 | 10/2004 | Valkirs ............ 435/7.1 | | 2005/0010137 A1 | 1/2005 | Hodges ............ 600/583 |
| 2004/0209350 A1 | 10/2004 | Sakata ............ 435/287.1 | | 2005/0010198 A1 | 1/2005 | Marchitto ............ 606/9 |
| 2004/0209354 A1 | 10/2004 | Mathies ............ 435/287.2 | | 2005/0011759 A1 | 1/2005 | Moerman ............ 204/403.03 |
| 2004/0210279 A1 | 10/2004 | Gruzdev ............ 607/89 | | 2005/0013731 A1 | 1/2005 | Burke ............ 422/56 |
| 2004/0211666 A1 | 10/2004 | Pamidi ............ 204/403.01 | | 2005/0014997 A1 | 1/2005 | Ruchti ............ 600/310 |
| 2004/0214253 A1 | 10/2004 | Paek ............ 435/7.92 | | 2005/0015020 A1 | 1/2005 | Levaughn ............ 600/583 |
| 2004/0215224 A1 | 10/2004 | Sakata ............ 606/181 | | 2005/0016844 A1 | 1/2005 | Burke ............ 204/403.1 |
| 2004/0215225 A1 | 10/2004 | Nakayama ............ 606/182 | | 2005/0019212 A1 | 1/2005 | Bhullar ............ 422/56 |
| 2004/0216516 A1 | 11/2004 | Sato ............ 73/64.56 | | 2005/0019219 A1 | 1/2005 | Oshiman ............ 422/82.12 |
| 2004/0217019 A1 | 11/2004 | Cai ............ 205/792 | | 2005/0019805 A1 | 1/2005 | Groll ............ 435/6 |
| 2004/0219500 A1 | 11/2004 | Brown ............ 434/307 R | | 2005/0019945 A1 | 1/2005 | Groll ............ 436/169 |
| 2004/0219535 A1 | 11/2004 | Bell ............ 435/6 | | 2005/0019953 A1 | 1/2005 | Groll ............ 436/514 |
| 2004/0220456 A1 | 11/2004 | Eppstein ............ 600/309 | | 2005/0021066 A1 | 1/2005 | Kuhr ............ 606/181 |
| 2004/0220495 A1 | 11/2004 | Cahir ............ 600/562 | | 2005/0027181 A1 | 2/2005 | Goode et al. |
| 2004/0220564 A1 | 11/2004 | Ho ............ 606/47 | | 2005/0027211 A1 | 2/2005 | Kuhr ............ 600/583 |
| 2004/0220603 A1 | 11/2004 | Rutynowski ............ 606/181 | | 2005/0027562 A1 | 2/2005 | Brown ............ 705/2 |
| 2004/0222092 A1 | 11/2004 | Musho ............ 204/401 | | 2005/0033341 A1 | 2/2005 | Vreeke ............ 606/181 |
| 2004/0224369 A1 | 11/2004 | Cai ............ 435/7.7 | | 2005/0034983 A1 | 2/2005 | Chambers ............ 204/403.01 |
| 2004/0225230 A1 | 11/2004 | Liamos ............ 600/583 | | 2005/0036020 A1 | 2/2005 | Li ............ 347/100 |
| 2004/0225311 A1 | 11/2004 | Levaughn ............ 606/181 | | 2005/0036146 A1 | 2/2005 | Braig ............ 356/246 |
| 2004/0225312 A1 | 11/2004 | Orloff ............ 606/181 | | 2005/0036906 A1 | 2/2005 | Nakahara et al. ............ 422/58 |
| 2004/0230216 A1 | 11/2004 | Levaughn ............ 606/181 | | 2005/0036909 A1 | 2/2005 | Erickson ............ 422/61 |
| 2004/0231984 A1 | 11/2004 | Lauks ............ 204/416 | | 2005/0037482 A1 | 2/2005 | Braig et al. ............ 435/287 |
| 2004/0232009 A1 | 11/2004 | Okuda ............ 205/789 | | 2005/0038329 A1 | 2/2005 | Morris ............ 600/319 |
| 2004/0236250 A1 | 11/2004 | Hodges ............ 600/583 | | 2005/0038330 A1 | 2/2005 | Jansen ............ 600/345 |
| 2004/0236251 A1 | 11/2004 | Roe ............ 600/583 | | 2005/0038463 A1 | 2/2005 | Davar ............ 606/181 |
| 2004/0236268 A1 | 11/2004 | Mitragotri ............ 604/20 | | 2005/0038464 A1 | 2/2005 | Schraga ............ 606/182 |
| 2004/0236362 A1 | 11/2004 | Schraga ............ 606/181 | | 2005/0038465 A1 | 2/2005 | Shraga ............ 606/182 |
| 2004/0238357 A1 | 12/2004 | Bhullar et al. ............ 204/400 | | 2005/0038674 A1 | 2/2005 | Braig ............ 705/2 |
| 2004/0238358 A1 | 12/2004 | Forrow ............ 204/403 | | 2005/0042766 A1 | 2/2005 | Ohman ............ 436/174 |
| 2004/0238359 A1 | 12/2004 | Ikeda ............ 204/403.1 | | 2005/0043894 A1 | 2/2005 | Fernandez ............ 702/19 |
| 2004/0241746 A1 | 12/2004 | Adlassnig ............ 435/7.1 | | 2005/0043965 A1 | 2/2005 | Heller ............ 705/2 |
| 2004/0242977 A1 | 12/2004 | Dosmann ............ 600/315 | | 2005/0045476 A1 | 3/2005 | Neel ............ 204/403.2 |
| 2004/0243164 A1 | 12/2004 | D'Agostino ............ 606/181 | | 2005/0049473 A1 | 3/2005 | Desai ............ 600/347 |
| 2004/0243165 A1 | 12/2004 | Koike ............ 606/181 | | 2005/0050859 A1 | 3/2005 | Coppeta ............ 53/471 |
| 2004/0245101 A1 | 12/2004 | Willner ............ 204/403 | | 2005/0054082 A1 | 3/2005 | Pachl ............ 435/287.2 |
| 2004/0248282 A1 | 12/2004 | Sobha ............ 435/287.2 | | 2005/0059895 A1 | 3/2005 | Brown ............ 600/481 |
| 2004/0248312 A1 | 12/2004 | Vreeke ............ 436/95 | | 2005/0060194 A1 | 3/2005 | Brown ............ 705/2 |
| 2004/0249254 A1 | 12/2004 | Racchini ............ 600/347 | | 2005/0067280 A1 | 3/2005 | Reid ............ 204/403.14 |
| 2004/0249310 A1 | 12/2004 | Shartle ............ 600/583 | | 2005/0067737 A1 | 3/2005 | Rappin ............ 264/272.19 |
| 2004/0249311 A1 | 12/2004 | Haar ............ 600/584 | | 2005/0070771 A1 | 3/2005 | Rule ............ 600/316 |
| 2004/0249405 A1 | 12/2004 | Watanabe ............ 606/181 | | 2005/0070819 A1 | 3/2005 | Poux ............ 600/576 |
| 2004/0249406 A1 | 12/2004 | Griffin ............ 606/182 | | 2005/0070945 A1 | 3/2005 | Schraga ............ 606/182 |
| 2004/0251131 A1 | 12/2004 | Ueno ............ 204/403 | | 2005/0072670 A1 | 4/2005 | Hasegawa ............ 204/403.01 |
| 2004/0253634 A1 | 12/2004 | Wang ............ 435/7.1 | | 2005/0077176 A1 | 4/2005 | Hodges ............ 204/403.01 |
| 2004/0254434 A1 | 12/2004 | Goodnow ............ 600/365 | | 2005/0077584 A1 | 4/2005 | Uhland ............ 257/414 |
| 2004/0254599 A1 | 12/2004 | Lipoma ............ 606/181 | | 2005/0079542 A1 | 4/2005 | Cullen ............ 435/7.1 |
| 2004/0256228 A1 | 12/2004 | Huang ............ 204/434 | | 2005/0080652 A1 | 4/2005 | Brown ............ 705/2 |
| 2004/0256248 A1 | 12/2004 | Burke ............ 205/792 | | 2005/0085839 A1 | 4/2005 | Allen ............ 606/181 |
| 2004/0256685 A1 | 12/2004 | Chou ............ 257/414 | | 2005/0085840 A1 | 4/2005 | Yi ............ 606/182 |
| 2004/0258564 A1 | 12/2004 | Charlton ............ 422/58 | | 2005/0086083 A1 | 4/2005 | Brown ............ 705/2 |
| 2004/0260204 A1 | 12/2004 | Boecker ............ 600/584 | | 2005/0090754 A1 | 4/2005 | Wolf ............ 600/509 |
| 2004/0260324 A1 | 12/2004 | Fukuzawa ............ 606/181 | | 2005/0090850 A1 | 4/2005 | Toes ............ 606/182 |
| 2004/0260325 A1 | 12/2004 | Kuhr ............ 606/181 | | 2005/0096520 A1 | 5/2005 | Maekawa ............ 600/365 |
| 2004/0260326 A1 | 12/2004 | Lipoma ............ 606/182 | | 2005/0096565 A1 | 5/2005 | Chang ............ 600/584 |
| 2004/0260511 A1 | 12/2004 | Burke ............ 702/182 | | 2005/0096586 A1 | 5/2005 | Trautman ............ 604/46 |
| 2004/0267105 A1 | 12/2004 | Monfre ............ 600/344 | | 2005/0096587 A1 | 5/2005 | Santini, Jr. ............ 604/66 |

| | | | |
|---|---|---|---|
| 2005/0096686 A1 | 5/2005 | Allen | 606/181 |
| 2005/0098431 A1 | 5/2005 | Hodges | 204/403.01 |
| 2005/0098432 A1 | 5/2005 | Grundel | 204/403.2 |
| 2005/0098433 A1 | 5/2005 | Grundel | 204/403.2 |
| 2005/0098434 A1 | 5/2005 | Grundel | 204/403.02 |
| 2005/0100880 A1 | 5/2005 | Chang | 435/4 |
| 2005/0101841 A9 | 5/2005 | Kaylor | 600/300 |
| 2005/0101979 A1 | 5/2005 | Alden | 606/181 |
| 2005/0101980 A1 | 5/2005 | Alden | 606/181 |
| 2005/0101981 A1 | 5/2005 | Alden | 606/181 |
| 2005/0103624 A1 | 5/2005 | Bhullar | 204/403.01 |
| 2005/0106713 A1 | 5/2005 | Phan | 435/287.2 |
| 2005/0109637 A1 | 5/2005 | Iyengar | 205/775 |
| 2005/0112782 A1 | 5/2005 | Buechler | 436/518 |
| 2005/0113658 A1 | 5/2005 | Jacobson | 600/342 |
| 2005/0113717 A1 | 5/2005 | Matzinger | 600/573 |
| 2005/0114062 A1 | 5/2005 | Davies | 702/104 |
| 2005/0114154 A1 | 5/2005 | Wolkowicz | 705/1 |
| 2005/0114444 A1 | 5/2005 | Brown | 709/203 |
| 2005/0118056 A1 | 6/2005 | Swanson | 423/23 |
| 2005/0119681 A1 | 6/2005 | Marshall | 606/181 |
| 2005/0123443 A1 | 6/2005 | Fujiwara | 422/58 |
| 2005/0123680 A1 | 6/2005 | Kang | 427/248.1 |
| 2005/0124869 A1 | 6/2005 | Hefti | 600/316 |
| 2005/0125017 A1 | 6/2005 | Kudrna | 606/181 |
| 2005/0125018 A1 | 6/2005 | Galloway | 606/181 |
| 2005/0125019 A1 | 6/2005 | Kudrna | 606/182 |
| 2005/0126929 A1 | 6/2005 | Mansouri | 205/778 |
| 2005/0130248 A1 | 6/2005 | Willner | 435/14 |
| 2005/0130249 A1 | 6/2005 | Parris | 435/14 |
| 2005/0130292 A1 | 6/2005 | Ahn | 435/287.1 |
| 2005/0131286 A1 | 6/2005 | Parker | 600/328 |
| 2005/0131441 A1 | 6/2005 | Iio | 606/182 |
| 2005/0133368 A1 | 6/2005 | Davies | 204/403.01 |
| 2005/0136471 A1 | 6/2005 | Bhullar | 435/6 |
| 2005/0136501 A1 | 6/2005 | Kuriger | 435/14 |
| 2005/0136529 A1 | 6/2005 | Yang | 435/287 |
| 2005/0136550 A1 | 6/2005 | Yang | 436/514 |
| 2005/0137531 A1 | 6/2005 | Gonnelli | 604/173 |
| 2005/0137536 A1 | 6/2005 | Gonnelli | 604/264 |
| 2005/0143675 A1 | 6/2005 | Neel | 600/583 |
| 2005/0143713 A1 | 6/2005 | Delmore | 604/506 |
| 2005/0143771 A1 | 6/2005 | Stout | 606/181 |
| 2005/0145490 A1 | 7/2005 | Shinno | 204/403 |
| 2005/0145491 A1 | 7/2005 | Amano | 204/403 |
| 2005/0145520 A1 | 7/2005 | Ilo | 206/365 |
| 2005/0149088 A1 | 7/2005 | Fukuda | 606/181 |
| 2005/0149089 A1 | 7/2005 | Trissel | 606/181 |
| 2005/0150762 A1 | 7/2005 | Butters | 204/403 |
| 2005/0150763 A1 | 7/2005 | Butters | 204/403 |
| 2005/0154277 A1 | 7/2005 | Ting | 600/407 |
| 2005/0154374 A1 | 7/2005 | Hunter | 604/890 |
| 2005/0154410 A1 | 7/2005 | Conway | 606/181 |
| 2005/0154616 A1 | 7/2005 | Iliff | 705/3 |
| 2005/0158850 A1 | 7/2005 | Kubo | 435/287.2 |
| 2005/0159656 A1 | 7/2005 | Hockersmith | 600/315 |
| 2005/0159768 A1 | 7/2005 | Boehm | 606/182 |
| 2005/0164322 A1 | 7/2005 | Heller | 435/14 |
| 2005/0164329 A1 | 7/2005 | Wallace-Davis | 435/25 |
| 2005/0165285 A1 | 7/2005 | Iliff | 600/300 |
| 2005/0165393 A1 | 7/2005 | Eppstein | 606/41 |
| 2005/0165622 A1 | 7/2005 | Neel | 705/2 |
| 2005/0169961 A1 | 8/2005 | Hunter | 424/423 |
| 2005/0170448 A1 | 8/2005 | Burson | 435/14 |
| 2005/0171567 A1 | 8/2005 | DeHart | 606/181 |
| 2005/0172021 A1 | 8/2005 | Brown | 709/224 |
| 2005/0172022 A1 | 8/2005 | Brown | 709/224 |
| 2005/0173245 A1 | 8/2005 | Feldman | 204/403.01 |
| 2005/0173246 A1 | 8/2005 | Hodges | 204/403.11 |
| 2005/0175509 A1 | 8/2005 | Nakaminami | 422/82.03 |
| 2005/0176084 A1 | 8/2005 | Burkoth | 435/14 |
| 2005/0176133 A1 | 8/2005 | Miyashita | 435/287.1 |
| 2005/0177071 A1 | 8/2005 | Nakayama | 600/583 |
| 2005/0177201 A1 | 8/2005 | Freeman | 607/46 |
| 2005/0177398 A1 | 8/2005 | Watanabe et al. | 705/3 |
| 2005/0178218 A1 | 8/2005 | Montagu | 73/864.34 |
| 2005/0181010 A1 | 8/2005 | Hunter | 424/423 |
| 2005/0181497 A1 | 8/2005 | Salto et al. | 435/287.1 |
| 2005/0182307 A1 | 8/2005 | Currie | 600/300 |
| 2005/0187439 A1 | 8/2005 | Blank | 600/310 |
| 2005/0187444 A1 | 8/2005 | Hubner | 600/322 |
| 2005/0192488 A1 | 9/2005 | Bryenton | 600/301 |
| 2005/0196821 A1 | 9/2005 | Monfre | 435/14 |
| 2005/0197666 A1 | 9/2005 | Raney | 606/181 |
| 2005/0201897 A1 | 9/2005 | Zimmer | 422/82.05 |
| 2005/0202567 A1 | 9/2005 | Zanzucchi | 436/95 |
| 2005/0203358 A1 | 9/2005 | Monfre | 600/331 |
| 2005/0203364 A1 | 9/2005 | Monfre | 600/365 |
| 2005/0204939 A1 | 9/2005 | Krejci | 101/129 |
| 2005/0205422 A1 | 9/2005 | Moser | 204/403.06 |
| 2005/0205816 A1 | 9/2005 | Hayenga | 251/61.1 |
| 2005/0209515 A1 | 9/2005 | Hockersmith | 600/316 |
| 2005/0209564 A1 | 9/2005 | Bonner | 604/173 |
| 2005/0209625 A1 | 9/2005 | Chan | 606/181 |
| 2005/0211571 A1 | 9/2005 | Schulein | 205/777.5 |
| 2005/0211572 A1 | 9/2005 | Buck | 205/778 |
| 2005/0214881 A1 | 9/2005 | Azarnia | 435/7.92 |
| 2005/0214892 A1 | 9/2005 | Kovatchev | 435/25 |
| 2005/0215871 A1 | 9/2005 | Feldman | 600/309 |
| 2005/0215872 A1 | 9/2005 | Berner | 600/347 |
| 2005/0215923 A1 | 9/2005 | Wiegel | 600/573 |
| 2005/0215925 A1 | 9/2005 | Chan | 600/583 |
| 2005/0216046 A1 | 9/2005 | Yeoh | 606/181 |
| 2005/0218024 A1 | 10/2005 | Lang | 206/438 |
| 2005/0221276 A1 | 10/2005 | Rozakis | 435/4 |
| 2005/0221470 A1 | 10/2005 | Matsumoto | 435/287.1 |
| 2005/0222599 A1 | 10/2005 | Czernecki | 606/182 |
| 2005/0227372 A1 | 10/2005 | Khan | 436/514 |
| 2005/0228242 A1 | 10/2005 | Kawamura | 600/300 |
| 2005/0228883 A1 | 10/2005 | Brown | 709/224 |
| 2005/0230252 A1 | 10/2005 | Tsai | 204/450 |
| 2005/0230253 A1 | 10/2005 | Marquant | 204/451 |
| 2005/0232813 A1 | 10/2005 | Karmali | 422/58 |
| 2005/0232815 A1 | 10/2005 | Ruhl | 422/66 |
| 2005/0234368 A1 | 10/2005 | Wong | 600/583 |
| 2005/0234486 A1 | 10/2005 | Allen | 606/181 |
| 2005/0234487 A1 | 10/2005 | Shi | 600/181 |
| 2005/0234488 A1 | 10/2005 | Allen | 606/181 |
| 2005/0234489 A1 | 10/2005 | Allen | 606/181 |
| 2005/0234490 A1 | 10/2005 | Allen | 606/181 |
| 2005/0234491 A1 | 10/2005 | Allen | 606/181 |
| 2005/0234492 A1 | 10/2005 | Tsai | 606/181 |
| 2005/0234494 A1 | 10/2005 | Conway | 606/181 |
| 2005/0234495 A1 | 10/2005 | Schraga | 606/181 |
| 2005/0235060 A1 | 10/2005 | Brown | 709/224 |
| 2005/0239154 A1 | 10/2005 | Feldman | 435/14 |
| 2005/0239156 A1 | 10/2005 | Drucker | 435/14 |
| 2005/0239194 A1 | 10/2005 | Takahashi | 435/287.2 |
| 2005/0240090 A1 | 10/2005 | Ruchti | 600/316 |
| 2005/0240119 A1 | 10/2005 | Draudt | 600/583 |
| 2005/0240207 A1 | 10/2005 | Marshall | 606/181 |
| 2005/0240778 A1 | 10/2005 | Saito | 713/186 |
| 2005/0245798 A1 | 11/2005 | Yamaguchi | 600/345 |
| 2005/0245843 A1 | 11/2005 | Day | 600/583 |
| 2005/0245844 A1 | 11/2005 | Mace | 600/583 |
| 2005/0245845 A1 | 11/2005 | Roe | 600/583 |
| 2005/0245954 A1 | 11/2005 | Roe | 606/181 |
| 2005/0245955 A1 | 11/2005 | Schraga | 606/181 |
| 2005/0256534 A1 | 11/2005 | Alden | 606/182 |
| 2005/0258035 A1 | 11/2005 | Harding | 204/403.01 |
| 2005/0258036 A1 | 11/2005 | Harding | 204/403.01 |
| 2005/0258050 A1 | 11/2005 | Harding | 205/775 |
| 2005/0265094 A1 | 12/2005 | Harding | 365/203 |
| 2005/0276133 A1 | 12/2005 | Harding | 365/203 |
| 2005/0278945 A1 | 12/2005 | Feldman | 29/830 |
| 2005/0279631 A1 | 12/2005 | Celentano | 204/403.01 |

| Pub. No. | Date | Inventor | Class |
|---|---|---|---|
| 2005/0279647 A1 | 12/2005 | Beaty | 205/792 |
| 2005/0283094 A1 | 12/2005 | Thym | 600/583 |
| 2005/0284110 A1 | 12/2005 | Lang | 53/473 |
| 2005/0284757 A1 | 12/2005 | Allen | 204/400 |
| 2005/0287620 A1 | 12/2005 | Heller | 435/14 |
| 2005/0288637 A1 | 12/2005 | Kuhr | 604/204 |
| 2005/0288698 A1 | 12/2005 | Matsumoto | 606/181 |
| 2005/0288699 A1 | 12/2005 | Schraga | 606/181 |
| 2006/0000549 A1 | 1/2006 | Lang | 156/320 |
| 2006/0003398 A1 | 1/2006 | Heller | 435/14 |
| 2006/0004270 A1 | 1/2006 | Bedard | 600/316 |
| 2006/0004271 A1 | 1/2006 | Peyser | 600/362 |
| 2006/0004272 A1 | 1/2006 | Shah | 600/365 |
| 2006/0006574 A1 | 1/2006 | Lang | 264/165 |
| 2006/0008389 A1 | 1/2006 | Sacherer | 422/102 |
| 2006/0015129 A1 | 1/2006 | Shahrokni | 606/181 |
| 2006/0016698 A1 | 1/2006 | Lee | 205/777.5 |
| 2006/0020228 A1 | 1/2006 | Fowler | 600/583 |
| 2006/0024774 A1 | 2/2006 | Zocchi | 435/14 |
| 2006/0025662 A1 | 2/2006 | Buse | 600/347 |
| 2006/0029979 A1 | 2/2006 | Bai | 435/7.1 |
| 2006/0029991 A1 | 2/2006 | Hagino | 435/14 |
| 2006/0030028 A1 | 2/2006 | Nakaminami | 435/287.2 |
| 2006/0030788 A1 | 2/2006 | Wong | 600/583 |
| 2006/0034728 A1 | 2/2006 | Kloepfer | 422/68.1 |
| 2006/0040333 A1 | 2/2006 | Zocchi | 435/14 |
| 2006/0047220 A1 | 3/2006 | Sakata | 600/583 |
| 2006/0047294 A1 | 3/2006 | Mori | 606/181 |
| 2006/0052723 A1 | 3/2006 | Roe | 600/583 |
| 2006/0052724 A1 | 3/2006 | Roe | 600/583 |
| 2006/0052809 A1 | 3/2006 | Karbowniczek | 606/181 |
| 2006/0052810 A1 | 3/2006 | Freeman | 606/181 |
| 2006/0058827 A1 | 3/2006 | Sakata | 606/181 |
| 2006/0058828 A1 | 3/2006 | Shi | 606/181 |
| 2006/0062852 A1 | 3/2006 | Holmes | 424/484 |
| 2006/0063988 A1 | 3/2006 | Schurman | 600/316 |
| 2006/0064035 A1 | 3/2006 | Wang | 600/583 |
| 2006/0079739 A1 | 4/2006 | Chen Wang | 600/300 |
| 2006/0079810 A1 | 4/2006 | Patel | 600/583 |
| 2006/0079811 A1 | 4/2006 | Roe | 600/583 |
| 2006/0079920 A1 | 4/2006 | Schraga | 606/181 |
| 2006/0081469 A1 | 4/2006 | Lee | 204/403.02 |
| 2006/0085020 A1 | 4/2006 | Freeman | 606/181 |
| 2006/0085137 A1 | 4/2006 | Bartkowiak | 702/19 |
| 2006/0086624 A1 | 4/2006 | Tapsak | 205/775 |
| 2006/0088945 A1 | 4/2006 | Douglas | 436/518 |
| 2006/0089566 A1 | 4/2006 | DeHart | 600/573 |
| 2006/0091006 A1 | 5/2006 | Wang | 204/403.02 |
| 2006/0094944 A1 | 5/2006 | Chuang | 600/347 |
| 2006/0094947 A1 | 5/2006 | Kovatchev | 600/365 |
| 2006/0094986 A1 | 5/2006 | Neel | 600/583 |
| 2006/0095061 A1 | 5/2006 | Trautman | 606/185 |
| 2006/0096859 A1 | 5/2006 | Lau | 204/403.14 |
| 2006/0099107 A1 | 5/2006 | Yamamoto | 422/57 |
| 2006/0099703 A1 | 5/2006 | Choi | 435/287.1 |
| 2006/0100542 A9 | 5/2006 | Wong, D | 600/583 |
| 2006/0100543 A1 | 5/2006 | Raney | 600/583 |
| 2006/0100654 A1 | 5/2006 | Fukuda | 606/181 |
| 2006/0100655 A1 | 5/2006 | Leong | 606/181 |
| 2006/0100656 A1 | 5/2006 | Olsen | 606/181 |
| 2006/0106373 A1 | 5/2006 | Cahir | 606/9 |
| 2006/0108236 A1 | 5/2006 | Kasielke | 205/792 |
| 2006/0113187 A1 | 6/2006 | Deng | 204/403.01 |
| 2006/0115857 A1 | 6/2006 | Keen | 435/7.1 |
| 2006/0116562 A1 | 6/2006 | Acosta | 600/316 |
| 2006/0116704 A1 | 6/2006 | Ashby | 606/167 |
| 2006/0116705 A1 | 6/2006 | Schraga | 606/181 |
| 2006/0119362 A1 | 6/2006 | Kermani | 324/324 |
| 2006/0121547 A1 | 6/2006 | McIntire | 435/14 |
| 2006/0121625 A1 | 6/2006 | Clemens | 436/514 |
| 2006/0121759 A1 | 6/2006 | Kasai | 439/188 |
| 2006/0122099 A1 | 6/2006 | Aoki | 514/3 |
| 2006/0122536 A1 | 6/2006 | Haar | 600/581 |
| 2006/0129065 A1 | 6/2006 | Matsumoto | 600/583 |
| 2006/0129172 A1 | 6/2006 | Crossman | 606/181 |
| 2006/0129173 A1 | 6/2006 | Wilkinson | 606/181 |
| 2006/0134713 A1 | 6/2006 | Rylatt | 435/7.92 |
| 2006/0140457 A1 | 6/2006 | Simshauser | 382/124 |
| 2006/0144704 A1 | 7/2006 | Ghesquiere | 204/403.01 |
| 2006/0151323 A1 | 7/2006 | Cho | 204/403.04 |
| 2006/0155215 A1 | 7/2006 | Cha | 600/583 |
| 2006/0155316 A1 | 7/2006 | Perez | 606/181 |
| 2006/0155317 A1 | 7/2006 | List | 606/181 |
| 2006/0156796 A1 | 7/2006 | Burke | 73/61.44 |
| 2006/0157362 A1 | 7/2006 | Schraga | 206/363 |
| 2006/0161078 A1 | 7/2006 | Schraga | 600/583 |
| 2006/0161194 A1 | 7/2006 | Freeman | 606/185 |
| 2006/0166302 A1 | 7/2006 | Clarke | 435/25 |
| 2006/0167382 A1 | 7/2006 | Deshmukh | 600/583 |
| 2006/1051342 | 7/2006 | Yaguchi | 206/306 |
| 2006/0169599 A1 | 8/2006 | Feldman | 205/792 |
| 2006/0173254 A1 | 8/2006 | Acosta | 600/316 |
| 2006/0173255 A1 | 8/2006 | Acosta | 600/316 |
| 2006/0173379 A1 | 8/2006 | Rasch-Menges | 600/583 |
| 2006/0173380 A1 | 8/2006 | Hoenes | 600/583 |
| 2006/0173478 A1 | 8/2006 | Schraga | 606/181 |
| 2006/0175216 A1 | 8/2006 | Freeman | 206/363 |
| 2006/0178573 A1 | 8/2006 | Kermani | 600/347 |
| 2006/0178599 A1 | 8/2006 | Faupel | 600/578 |
| 2006/0178600 A1 | 8/2006 | Kennedy | 600/584 |
| 2006/0178686 A1 | 8/2006 | Schraga | 606/181 |
| 2006/0178687 A1 | 8/2006 | Freeman | 606/181 |
| 2006/0178688 A1 | 8/2006 | Freeman | 606/181 |
| 2006/0178689 A1 | 8/2006 | Freeman | 606/181 |
| 2006/0178690 A1 | 8/2006 | Freeman | 606/181 |
| 2006/0183871 A1 | 8/2006 | Ward | 525/464 |
| 2006/0183983 A1 | 8/2006 | Acosta | 600/316 |
| 2006/0184101 A1 | 8/2006 | Srinivasan | 604/68 |
| 2006/0188395 A1 | 8/2006 | Taniike | 422/57 |
| 2006/0189895 A1 | 8/2006 | Neel | 600/584 |
| 2006/0191787 A1 | 8/2006 | Wang | 204/400 |
| 2006/0195023 A1 | 8/2006 | Acosta | 600/316 |
| 2006/0195047 A1 | 8/2006 | Freeman | 600/583 |
| 2006/0195128 A1 | 8/2006 | Alden | 606/181 |
| 2006/0195129 A1 | 8/2006 | Freeman | 606/181 |
| 2006/0195130 A1 | 8/2006 | Freeman | 606/181 |
| 2006/0195131 A1 | 8/2006 | Freeman | 606/181 |
| 2006/0195132 A1 | 8/2006 | Freeman | 606/181 |
| 2006/0195133 A1 | 8/2006 | Freeman | 606/181 |
| 2006/0196031 A1 | 9/2006 | Hoenes | 29/432 |
| 2006/0196795 A1 | 9/2006 | Windus-Smith | 206/438 |
| 2006/0200044 A1 | 9/2006 | Freeman | 600/583 |
| 2006/0200045 A1 | 9/2006 | Roe | 600/583 |
| 2006/0200046 A1 | 9/2006 | Windus-Smith | 600/583 |
| 2006/0200181 A1 | 9/2006 | Fukuzawa | 606/181 |
| 2006/0200981 A1 | 9/2006 | Bhullar | 29/847 |
| 2006/0200982 A1 | 9/2006 | Bhullar | 29/847 |
| 2006/0204399 A1 | 9/2006 | Freeman | 422/58 |
| 2006/0205029 A1 | 9/2006 | Heller | 435/25 |
| 2006/0205060 A1 | 9/2006 | Kim | 435/287.2 |
| 2006/0206135 A1 | 9/2006 | Uehata | 606/181 |
| 2006/0211127 A1 | 9/2006 | Iwaki | 436/169 |
| 2006/0211927 A1 | 9/2006 | Acosta | 600/316 |
| 2006/0211931 A1 | 9/2006 | Blank | 600/344 |
| 2006/0219551 A1 | 10/2006 | Edelbrock | 204/403.14 |
| 2006/0222567 A1 | 10/2006 | Kloepfer | 422/68.1 |
| 2006/0224171 A1 | 10/2006 | Sakata | 606/181 |
| 2006/0224172 A1 | 10/2006 | LeVaughn | 606/181 |
| 2006/0229532 A1 | 10/2006 | Wong | 600/583 |
| 2006/0229533 A1 | 10/2006 | Hoenes | 600/584 |
| 2006/0229651 A1 | 10/2006 | Marshall | 606/181 |
| 2006/0231396 A1 | 10/2006 | Yamaoka | 204/403.14 |
| 2006/0231418 A1 | 10/2006 | Harding | 205/775 |
| 2006/0231442 A1 | 10/2006 | Windus-Smith | 206/438 |
| 2006/0234369 A1 | 10/2006 | Sih | 435/287.1 |
| 2006/0235284 A1 | 10/2006 | Lee | 600/345 |

| | | | | | |
|---|---|---|---|---|---|
| 2006/0235454 A1 | 10/2006 | LeVaughn .................... 606/181 | EP | 0735363 | 10/1996 |
| 2006/0241517 A1 | 10/2006 | Fowler ........................ 600/583 | EP | 0505504 | 3/1997 |
| 2006/0241666 A1 | 10/2006 | Briggs ........................ 606/181 | EP | 0406304 | 8/1997 |
| 2006/0241667 A1 | 10/2006 | Freeman ..................... 606/181 | EP | 0537761 | 8/1997 |
| 2006/0241668 A1 | 10/2006 | Schraga ...................... 606/181 | EP | 0795601 | 9/1997 |
| 2006/0241669 A1 | 10/2006 | Stout .......................... 606/182 | EP | 0562370 | 11/1997 |
| 2006/0247554 A1 | 11/2006 | Roe ............................ 600/583 | EP | 0415393 | 12/1997 |
| 2006/0247555 A1 | 11/2006 | Harttig ....................... 600/584 | EP | 0560336 | 5/1998 |
| 2006/0247670 A1 | 11/2006 | LeVaughn .................... 606/181 | EP | 0878 708 | 11/1998 |
| 2006/0247671 A1 | 11/2006 | Levaughn ..................... 606/182 | EP | 0 898 936 A2 | 3/1999 |
| 2006/0259057 A1 | 11/2006 | Kim ........................... 606/181 | EP | 0505475 | 3/1999 |
| 2006/0259058 A1 | 11/2006 | Schiff ......................... 606/181 | EP | 0901018 | 3/1999 |
| 2006/0259060 A1 | 11/2006 | Whitson ...................... 606/182 | EP | 0470649 | 6/1999 |
| 2006/0264718 A1 | 11/2006 | Ruchti ........................ 600/310 | EP | 0 951 939 | 10/1999 |
| 2006/0264996 A1 | 11/2006 | Levaughn ..................... 606/181 | EP | 0 951 939 A2 | 10/1999 |
| 2006/0264997 A1 | 11/2006 | Colonna ...................... 606/181 | EP | 0847447 | 11/1999 |
| 2006/0271083 A1 | 11/2006 | Boecker ...................... 606/181 | EP | 0964059 | 12/1999 |
| 2006/0271084 A1 | 11/2006 | Schraga ...................... 606/182 | EP | 0969097 | 1/2000 |
| 2006/0276724 A1 | 12/2006 | Freeman ..................... 600/583 | EP | 0 985 376 | 5/2000 |
| 2006/0277048 A1 | 12/2006 | Kintzig ....................... 704/275 | EP | 1021950 | 7/2000 |
| 2006/0278545 A1 | 12/2006 | Henning ..................... 206/363 | EP | 0894869 | 2/2001 |
| 2006/0282109 A1 | 12/2006 | Jansen ........................ 606/181 | EP | 1074832 | 2/2001 |
| 2006/0286620 A1 | 12/2006 | Werner ........................ 435/14 | EP | 1093854 | 4/2001 |
| 2006/0287664 A1 | 12/2006 | Grage ......................... 606/181 | EP | 1 101 443 | 5/2001 |
| 2006/0293577 A1 | 12/2006 | Morrison .................... 600/365 | EP | 1101443 | 5/2001 |
| 2007/0004989 A1 | 1/2007 | Dhillon ....................... 600/583 | EP | 1114995 | 7/2001 |
| 2007/0004990 A1 | 1/2007 | Kistner ....................... 600/583 | EP | 0736607 | 8/2001 |
| 2007/0007183 A1 | 1/2007 | Schulat ....................... 209/573 | EP | 1 157 660 | 11/2001 |
| 2007/0009381 A1 | 1/2007 | Schulat ......................... 422/58 | EP | 0874984 | 11/2001 |
| 2007/0010839 A1 | 1/2007 | Galloway .................... 606/167 | EP | 0730037 | 12/2001 |
| 2007/0010841 A1 | 1/2007 | Teo ............................. 606/181 | EP | 0636879 | 1/2002 |
| 2007/0015978 A1 | 1/2007 | Kanayama ................... 600/310 | EP | 01174083 | 1/2002 |
| 2007/0016079 A1 | 1/2007 | Freeman ..................... 600/476 | EP | 0851224 | 3/2002 |
| 2007/0016103 A1 | 1/2007 | Calasso ...................... 600/583 | EP | 0759553 | 5/2002 |
| 2007/0016104 A1 | 1/2007 | Jansen ........................ 600/583 | EP | 0856586 | 5/2002 |
| 2007/0038235 A1 | 2/2007 | Freeman et al. | EP | 0817809 | 7/2002 |
| 2007/0129650 A1 | 6/2007 | Freeman et al. | EP | 0872728 | 7/2002 |
| 2007/0142748 A1 | 6/2007 | Deshmukh et al. | EP | 0795748 | 8/2002 |
| 2007/0173741 A1 | 7/2007 | Deshmukh et al. | EP | 0685737 | 9/2002 |
| 2007/0276290 A1 | 11/2007 | Boecker et al. | EP | 0958495 | 11/2002 |
| 2008/0047764 A1 | 2/2008 | Lee et al. | EP | 0937249 | 12/2002 |
| 2008/0194987 A1 | 8/2008 | Boecker | EP | 0880692 | 1/2004 |
| | | | EP | 01374770 | 1/2004 |
| | FOREIGN PATENT DOCUMENTS | | EP | 1246688 | 5/2004 |
| | | | EP | 1502614 | 2/2005 |
| DE | 200 09 475 | 9/2000 | EP | 1790288 A1 | 5/2007 |
| DE | 29824204 | 10/2000 | EP | 2039294 A1 | 3/2009 |
| DE | 10032042 | 1/2002 | FR | 2 555 432 A | 5/1985 |
| DE | 10057832 | 2/2002 | GB | 2168815 | 6/1986 |
| DE | 10057832 C1 | 2/2002 | GB | 233936 A | 6/1999 |
| DE | 10142232 | 3/2003 | GB | 2335860 A | 10/1999 |
| DE | 10208575 C1 | 8/2003 | GB | 2335990 A | 10/1999 |
| DE | 10245721 | 12/2003 | WO | WO 80/01389 | 7/1980 |
| DE | 10361560 A1 | 7/2005 | WO | WO 85/04089 | 9/1985 |
| EP | 0199484 A2 | 10/1986 | WO | WO 86/07632 | 12/1985 |
| EP | 0289 269 | 11/1988 | WO | WO 91/09139 | 6/1991 |
| EP | 0320109 | 6/1989 | WO | WO 93/06979 | 4/1993 |
| EP | 0 364 208 A1 | 4/1990 | WO | WO 93/25898 | 12/1993 |
| EP | 0170375 | 5/1990 | WO | WO 94/27140 | 11/1994 |
| EP | 0136362 | 12/1990 | WO | WO 94/29703 | 12/1994 |
| EP | 0453283 | 10/1991 | WO | WO 94/29704 | 12/1994 |
| EP | 0263948 | 2/1992 | WO | WO 94/29731 | 12/1994 |
| EP | 0374355 | 6/1993 | WO | WO 95/00662 | 1/1995 |
| EP | 0351891 | 9/1993 | WO | WO 95/06240 | 3/1995 |
| EP | 0593096 | 4/1994 | WO | WO 95/10223 | 4/1995 |
| EP | 0415388 | 5/1995 | WO | WO 95/22597 | 8/1995 |
| EP | 0505494 | 7/1995 | WO | WO 96/30431 | 10/1996 |
| EP | 0359831 | 8/1995 | WO | WO 97/02359 | 1/1997 |
| EP | 0471986 | 10/1995 | WO | WO 97/02487 | 1/1997 |
| EP | 0368474 | 12/1995 | WO | WO 97/11883 A1 | 4/1997 |
| EP | 0461601 | 12/1995 | WO | WO 97/18464 | 5/1997 |
| EP | 0429076 | 1/1996 | WO | WO 97/30344 | 8/1997 |
| EP | 0552223 | 7/1996 | WO | WO 97/42882 | 11/1997 |

| | | | | | | |
|---|---|---|---|---|---|---|
| WO | WO 97/45720 | 12/1997 | | WO | WO 02/41227 | 5/2002 |
| WO | WO 98/03431 | 1/1998 | | WO | WO 02/41779 | 5/2002 |
| WO | WO 98/19159 | 5/1998 | | WO | WO 02/44948 | 6/2002 |
| WO | WO 98/20332 | 5/1998 | | WO | WO /0249507 | 6/2002 |
| WO | WO 98/20348 | 5/1998 | | WO | WO 02/059734 | 8/2002 |
| WO | WO 98/24366 | 6/1998 | | WO | WO 02/069791 | 9/2002 |
| WO | WO 98/24373 | 6/1998 | | WO | WO 02/077638 | 10/2002 |
| WO | WO 98/35225 | 8/1998 | | WO | WO 02/100251 | 12/2002 |
| WO | WO 99/03584 | 1/1999 | | WO | WO 02/100252 | 12/2002 |
| WO | WO 99/05966 | 2/1999 | | WO | WO 02/100253 | 12/2002 |
| WO | WO 99/07431 A1 | 2/1999 | | WO | WO 02/100254 | 12/2002 |
| WO | WO 99/13100 | 3/1999 | | WO | WO 02/100460 | 12/2002 |
| WO | WO 99/17854 | 4/1999 | | WO | WO 02/100461 | 12/2002 |
| WO | WO 99/18532 | 4/1999 | | WO | WO 02/101343 | 12/2002 |
| WO | WO 99/19507 | 4/1999 | | WO | WO 02/101359 | 12/2002 |
| WO | WO 99/19717 | 4/1999 | | WO | WO 03/000321 | 1/2003 |
| WO | WO 99/27483 | 6/1999 | | WO | WO 03/023389 | 3/2003 |
| WO | WO 99/27852 | 6/1999 | | WO | WO 03/042691 | 5/2003 |
| WO | WO 99/62576 | 12/1999 | | WO | WO 03/045557 | 6/2003 |
| WO | WO 99/64580 | 12/1999 | | WO | WO 03/046542 | 6/2003 |
| WO | WO 00/06024 | 2/2000 | | WO | WO 03/049609 | 6/2003 |
| WO | WO 00/09184 | 2/2000 | | WO | WO 03/050534 | 6/2003 |
| WO | WO 00/11578 | 3/2000 | | WO | WO 03/066128 | 8/2003 |
| WO | WO 00/15103 | 3/2000 | | WO | WO 03/070099 | 8/2003 |
| WO | WO 00/17799 | 3/2000 | | WO | WO 03/071940 | 9/2003 |
| WO | WO 00/17800 | 3/2000 | | WO | WO 03/082091 A2 | 10/2003 |
| WO | WO 00/18293 | 4/2000 | | WO | WO 03/088851 A1 | 10/2003 |
| WO | WO 00/19346 | 4/2000 | | WO | WO /03088834 | 10/2003 |
| WO | WO 00/30186 | 5/2000 | | WO | WO 03/094752 | 11/2003 |
| WO | WO 00/32097 | 6/2000 | | WO | WO 03/101297 | 12/2003 |
| WO | WO 00/32098 | 6/2000 | | WO | WO 2004/008130 | 1/2004 |
| WO | WO 00/33236 | 6/2000 | | WO | WO 2004/022133 | 3/2004 |
| WO | WO 00/39914 | 7/2000 | | WO | WO 2004/026130 | 4/2004 |
| WO | WO 00/42422 | 7/2000 | | WO | WO 2004/040285 A2 | 5/2004 |
| WO | WO 00/44084 | 7/2000 | | WO | WO 2004/040287 A1 | 5/2004 |
| WO | WO 00/50771 | 8/2000 | | WO | WO 2004/040948 | 5/2004 |
| WO | WO 00/60340 | 10/2000 | | WO | WO 2004/041082 | 5/2004 |
| WO | WO 00/64022 | 10/2000 | | WO | WO 2004/045375 | 6/2004 |
| WO | WO 00/67245 | 11/2000 | | WO | WO 2004/054455 | 7/2004 |
| WO | WO 00/67268 | 11/2000 | | WO | WO 2004/060174 | 7/2004 |
| WO | WO 00/72452 | 11/2000 | | WO | WO 2004/060446 | 7/2004 |
| WO | WO 01/00090 | 1/2001 | | WO | WO 2004/091693 | 10/2004 |
| WO | WO 01/15807 | 3/2001 | | WO | WO 2004/098405 | 11/2004 |
| WO | WO 01/16578 A1 | 3/2001 | | WO | WO 2004/003147 | 12/2004 |
| WO | WO 01/75433 | 3/2001 | | WO | WO 2004/107964 | 12/2004 |
| WO | WO 01/23885 | 4/2001 | | WO | WO 2004/107975 | 12/2004 |
| WO | WO 01/25775 | 4/2001 | | WO | WO 2004/112602 | 12/2004 |
| WO | WO 01/26813 | 4/2001 | | WO | WO 2004/112612 A1 | 12/2004 |
| WO | WO 01/33216 | 5/2001 | | WO | WO 2005/001418 | 1/2005 |
| WO | WO 01/34029 | 5/2001 | | WO | WO 2005/006939 | 1/2005 |
| WO | WO 01/36955 | 5/2001 | | WO | WO 2005/011774 | 2/2005 |
| WO | WO 01/37174 | 5/2001 | | WO | WO 2005/016125 | 2/2005 |
| WO | WO 01/45014 A1 | 6/2001 | | WO | WO 2005/018425 | 3/2005 |
| WO | WO 01/40788 | 7/2001 | | WO | WO 2005/018430 | 3/2005 |
| WO | WO 01/57510 | 8/2001 | | WO | WO 2005/018454 | 3/2005 |
| WO | WO 01/64105 | 9/2001 | | WO | WO 2005/018709 | 3/2005 |
| WO | WO 01/66010 | 9/2001 | | WO | WO 2005/018710 | 3/2005 |
| WO | WO 01/69505 | 9/2001 | | WO | WO 2005/018711 | 3/2005 |
| WO | WO 01/72220 A | 10/2001 | | WO | WO 2005/022143 | 3/2005 |
| WO | WO 01/72225 | 10/2001 | | WO | WO 2005/023088 | 3/2005 |
| WO | WO 01/73124 | 10/2001 | | WO | WO 2005/033659 | 4/2005 |
| WO | WO 01/73395 | 10/2001 | | WO | WO 2005/034720 | 4/2005 |
| WO | WO 01/89691 | 11/2001 | | WO | WO 2005/034721 | 4/2005 |
| WO | WO 01/95806 | 12/2001 | | WO | WO 2005/034741 | 4/2005 |
| WO | WO 02/00101 | 1/2002 | | WO | WO 2005/034778 | 4/2005 |
| WO | WO 02/02796 | 1/2002 | | WO | WO 2005/035017 | 4/2005 |
| WO | WO 02/08750 | 1/2002 | | WO | WO 2005/035018 | 4/2005 |
| WO | WO 02/08753 | 1/2002 | | WO | WO 2005/037095 | 4/2005 |
| WO | WO 02/08950 | 1/2002 | | WO | WO 2005/046477 | 5/2005 |
| WO | WO 02/18940 | 3/2002 | | WO | WO 2005/065399 | 7/2005 |
| WO | WO 02/21317 | 3/2002 | | WO | WO 2005/065414 | 7/2005 |
| WO | WO 02/25551 | 3/2002 | | WO | WO 2005/065415 | 7/2005 |
| WO | WO 02/32559 | 4/2002 | | WO | WO 2005/065545 A2 | 7/2005 |

| | | | | | | |
|---|---|---|---|---|---|---|
| WO | WO 2005/072604 | 8/2005 | | WO | WO 2006/001973 | 1/2006 |
| WO | WO 2005/084557 | 9/2005 | | WO | WO 2006/011062 | 2/2006 |
| WO | WO 2005/104948 A1 | 11/2005 | | WO | WO 2006/013045 | 2/2006 |
| WO | WO 2005/116622 | 12/2005 | | WO | WO 2006/027702 A2 | 3/2006 |
| WO | WO 2005/119234 | 12/2005 | | WO | WO 2006/032391 | 3/2006 |
| WO | WO 2005/120365 A1 | 12/2005 | | WO | WO 2006/072004 | 7/2006 |
| WO | WO 2005/121759 | 12/2005 | | | | |

* cited by examiner

METHOD AND APPARATUS FOR PENETRATING TISSUE

CROSS-REFERENCE TO RELATED APPLICATION

This application is a divisional of U.S. Ser. No. 10/335,218, filed Dec. 31, 2002, now U.S. Pat. No. 7,331,931 which is a continuation-in-part of U.S. Ser. No. 10/127,395, filed Apr. 19, 2002, now U.S. Pat. No. 7,025,774 which is a continuation-in-part of U.S. Ser. No. 10/237,261, Sep. 5, 2002 now U.S. Pat. No. 7,344,507. All applications listed above are fully incorporated herein by reference for all purposes.

BACKGROUND OF THE INVENTION

Lancing devices are known in the medical health-care products industry for piercing the skin to produce blood for analysis. Typically, a drop of blood for this type of analysis is obtained by making a small incision in the fingertip, creating a small wound, which generates a small blood droplet on the surface of the skin.

Early methods of lancing included piercing or slicing the skin with a needle or razor. Current methods utilize lancing devices that contain a multitude of spring, cam and mass actuators to drive the lancet. These include cantilever springs, diaphragms, coil springs, as well as gravity plumbs used to drive the lancet. The device may be held against the skin and mechanically triggered to ballistically launch the lancet. Unfortunately, the pain associated with each lancing event using known technology discourages patients from testing. In addition to vibratory stimulation of the skin as the driver impacts the end of a launcher stop, known spring based devices have the possibility of harmonically oscillating against the patient tissue, causing multiple strikes due to recoil. This recoil and multiple strikes of the lancet against the patient is one major impediment to patient compliance with a structured glucose monitoring regime.

Another impediment to patient compliance is the lack of spontaneous blood flow generated by known lancing technology. In addition to the pain as discussed above, a patient may need more than one lancing event to obtain a blood sample since spontaneous blood generation is unreliable using known lancing technology. Thus the pain is multiplied by the number of tries it takes to successfully generate spontaneous blood flow. Different skin thickness may yield different results in terms of pain perception, blood yield and success rate of obtaining blood between different users of the lancing device. Known devices poorly account for these skin thickness variations.

A still further impediment to improved compliance with glucose monitoring are the many steps and hassle associated with each lancing event. Many diabetic patients that are insulin dependent may need to self-test for blood glucose levels five to six times daily. The large number of steps required in traditional methods of glucose testing, ranging from lancing, to milking of blood, applying blood to the test strip, and getting the measurements from the test strip, discourages many diabetic patients from testing their blood glucose levels as often as recommended. Older patients and those with deteriorating motor skills encounter difficulty loading lancets into launcher devices, transferring blood onto a test strip, or inserting thin test strips into slots on glucose measurement meters. Additionally, the wound channel left on the patient by known systems may also be of a size that discourages those who are active with their hands or who are worried about healing of those wound channels from testing their glucose levels.

SUMMARY OF THE INVENTION

Accordingly, an object of the present invention is to provide improved tissue penetrating systems, and their methods of use.

Another object of the present invention is to provide tissue penetrating systems, and their methods of use, that provide reduced pain when penetrating a target tissue.

Yet another object of the present invention is to provide tissue penetrating systems, and their methods of use, that provide controlled depth of penetration.

Still a further object of the present invention is to provide tissue penetrating systems, and their methods of use, that provide controlled velocities into and out of target tissue.

A further object of the present invention is to provide tissue penetrating systems, and their methods of use, that provide stimulation to a target tissue.

Another object of the present invention is to provide tissue penetrating systems, and their methods of use, that apply a pressure to a target tissue.

Yet another object of the present invention is to provide tissue penetrating systems, and their methods of use, with penetrating members that remain in sterile environments prior to launch.

Still another object of the present invention is to provide tissue penetrating systems, and their methods of use, with penetrating members that remain in sterile environments prior to launch, and the penetrating members are not used to breach the sterile environment.

A further object of the present invention is to provide improved tissue penetrating systems, and their methods of use, that have user interfaces.

Another object of the present invention is to provide improved tissue penetrating systems, and their methods of use, that have human interfaces.

Yet another object of the present invention is to provide tissue penetrating systems, and their methods of use, that have low volume sample chambers.

Still another object of the present invention is to provide tissue penetrating systems, and their methods of use, that have sample chambers with volumes that do not exceed 1 µL.

Another object of the present invention is to provide tissue penetrating systems, and their methods of use, that have multiple penetrating members housed in a cartridge.

These and other objects of the present invention are achieved in a body fluid sampling system for use on a tissue site that includes an electrically powered drive force generator. A penetrating member is operatively coupled to the force generator. The force generator moves the member along a path out of a housing having a penetrating member exit, into the tissue site, stops in the tissue site, and withdraws out of the tissue site. A cartridge houses the penetrating member. The cartridge has first and second seals coupled to the penetrating member to maintain a sterile environment around a portion of the penetration member prior to penetrating member actuation. A user interface is configured to relay at least one of, penetrating member performance or a penetrating member setting.

In another embodiment of the present invention, a body fluid sampling system for use on a tissue site includes an electrically powered drive force generator. A penetrating member is operatively coupled to the force generator. The force generator moves the member along a path out of a housing having a penetrating member exit, into the tissue site, stops in the tissue site, and withdraws out of the tissue site. A cartridge houses the penetrating member. The cartridge has first and second seals coupled to the penetrating member to maintain a sterile environment around a portion of the penetration member prior to penetrating member actuation. A human interface provides at least one output.

In another embodiment of the present invention, a body fluid sampling system for use on a tissue site provides an electrically powered drive force generator. A penetrating member is operatively coupled to the force generator. The force generator moves the member along a path out of a housing having a penetrating member exit, into the tissue site, stops in the tissue site, and withdraws out of the tissue site. A cartridge houses the penetrating member. The cartridge has first and second seals coupled to the penetrating member to maintain a sterile environment around a portion of the penetration member prior to penetrating member actuation. A user interface is configured to relay at least one of, penetrating member performance or a penetrating member setting.

In another embodiment, a body fluid sampling system for use on a tissue site, the system includes an electrically powered drive force generator. A penetrating member is operatively coupled to the force generator. The force generator moves the member along a path out of a housing having a penetrating member exit, into the tissue site, stops in the tissue site, and withdraws out of the tissue site. A cartridge houses the penetrating member. The cartridge has first and second seals coupled to the penetrating member to maintain a sterile environment around a portion of the penetration member prior to penetrating member actuation. A human interface provides at least one output.

In another embodiment of the present invention, a body fluid sampling system for use on a tissue site includes a drive force generator. A penetrating member is operatively coupled to the force generator. The force generator moves the member along a path out of a housing having a penetrating member exit, into the tissue site, stops in the tissue site, and withdraws out of the tissue site. The drive force generator is configured to be controlled to follow a predetermined velocity trajectory into the tissue and out of the tissue. A cartridge houses the penetrating member. The cartridge has first and second seals coupled to the penetrating member to maintain a sterile environment around a portion of the penetration member prior to penetrating member actuation. A user interface is configured to relay at least one of, penetrating member performance or a penetrating member setting.

In another embodiment of the present invention, a body fluid sampling system for use on a tissue site includes a drive force generator. A penetrating member is operatively coupled to the force generator. The force generator moves the member along a path out of a housing having a penetrating member exit, into the tissue site, stops in the tissue site, and withdraws out of the tissue site. The drive force generator is configured to be controlled to follow a predetermined velocity trajectory into the tissue and out of the tissue. A cartridge houses the penetrating member. The cartridge has first and second seals coupled to the penetrating member to maintain a sterile environment around a portion of the penetration member prior to penetrating member actuation. A human interface provides at least one output.

In another embodiment of the present invention, a body fluid sampling system for use on a tissue site includes a drive force generator. A penetrating member is operatively coupled to the force generator. The force generator moves the member along a path out of a housing having a penetrating member exit, into the tissue site, stops in the tissue site, and withdraws out of the tissue site. A position sensor is positioned to provide an indication of a position of the penetrating member during actuation. A cartridge houses the penetrating member. The cartridge has first and second seals coupled to the penetrating member to maintain a sterile environment around a portion of the penetration member prior to penetrating member actuation. A user interface is configured to relay at least one of, penetrating member performance or a penetrating member setting.

In another embodiment of the present invention, a body fluid sampling system for use on a tissue site includes a drive force generator. A penetrating member is operatively coupled to the force generator. The force generator moves the member along a path out of a housing having a penetrating member exit, into the tissue site, stops in the tissue site, and withdraws out of the tissue site. A position sensor is positioned to provide an indication of a position of the penetrating member during actuation. A cartridge houses the penetrating member. The cartridge has first and second seals coupled to the penetrating member to maintain a sterile environment around a portion of the penetration member prior to penetrating member actuation. A human interface provides at least one output.

In another embodiment of the present invention, a body fluid sampling system for use on a tissue site includes a drive force generator. A penetrating member is operatively coupled to the force generator. The force generator moves the member along a path out of a housing having a penetrating member exit, into the tissue site, stops in the tissue site, and withdraws out of the tissue site. The penetrating member is an elongate member without a molded attachment. A coupler, on the force generator, is configured to engage at least a portion of the elongate portion of the penetrating member, drive the member along a path into a tissue site and withdrawn it from a tissue site. A cartridge houses the penetrating member. The cartridge has first and second seals coupled to the penetrating member to maintain a sterile environment around a portion of the penetration member prior to penetrating member actuation. A user interface is configured to relay at least one of, penetrating member performance or a penetrating member setting.

In another embodiment of the present invention, a body fluid sampling system for use on a tissue site includes a drive force generator. A penetrating member is operatively coupled to the force generator. The force generator moves the member along a path out of a housing having a penetrating member exit, into the tissue site, stops in the tissue site, and withdraws out of the tissue site. The penetrating member is an elongate member without a molded attachment. A coupler, on the force generator, is configured to engage at least a portion of the elongate portion of the penetrating member, drive the member along a path into a tissue site and withdrawn it from a tissue site. A cartridge houses the penetrating member. The cartridge has first and second seals coupled to the penetrating member to maintain a sterile environment around a portion of the penetration member prior to penetrating member actuation. A human interface provides at least one output.

In another embodiment, a body fluid sampling system for use on a tissue site includes a drive force generator. A plurality of cartridges each contain a penetrating member. Each of the cartridges is coupled together to define a flexible array. A transport device moves each of the cartridges into a launch position to operatively couple the penetrating member to the force generator. Each cartridge has first and second seals coupled to the penetrating member to maintain a sterile environment around a portion of the penetration member prior to penetrating member actuation. A user interface is configured to relay at least one of, penetrating member performance or a penetrating member setting.

In another embodiment of the present invention, a body fluid sampling system for use on a tissue site includes a drive force generator. A plurality of cartridges each contain a penetrating member. Each of the cartridges is coupled together to define a flexible array. A transport device moves each of the cartridges into a launch position to operatively couple the penetrating member to the force generator. Each cartridge has first and second seals coupled to the penetrating member to maintain a sterile environment around a portion of the penetration member prior to penetrating member actuation. A human interface provides at least one output.

In another embodiment of the present invention, a body fluid sampling system for use on a tissue site includes a drive force generator. A penetrating member has an elongate portion without a molded attachment and is operatively coupled to the force generator. A sterility enclosure covers at least a tip of the penetrating member. The sterility enclosure is removed from the penetrating member prior to actuation of the member and positioned so that the penetrating member will not contact the enclosure during actuation. A user interface is configured to relay at least one of, penetrating member performance or a penetrating member setting.

In another embodiment of the present invention, a body fluid sampling system for use on a tissue site includes a drive force generator. A penetrating member has an elongate portion without a molded attachment and is operatively coupled to the force generator. A sterility enclosure covers at least a tip of the penetrating member. The sterility enclosure is removed from the penetrating member prior to actuation of the member and is positioned so that the penetrating member will not contact the enclosure during actuation. A human interface provides at least one output.

In another embodiment of the present invention, a body fluid sampling system for use on a tissue site includes a drive force generator. A penetrating member has an elongate portion without a molded attachment and is operatively coupled to the force generator. A sterility enclosure creates a sterile environment around at least a tip of the penetrating member. The penetrating member breaches the sterile environment during actuation. A user interface is configured to relay at least one of, penetrating member performance or a penetrating member setting.

In another embodiment of the present invention, a body fluid sampling system for use on a tissue site includes a drive force generator. A penetrating member has an elongate portion without a molded attachment and is operatively coupled to the force generator. A sterility enclosure creates a sterile environment around at least a tip of the penetrating member. The penetrating member breaches the sterile environment during actuation. A human interface provides at least one output.

In another embodiment of the present invention, a body fluid sampling system for use on a tissue site includes a drive force generator. A penetrating member is operatively coupled to the force generator. The force generator moves the member along a path out of a housing having a penetrating member exit, into the tissue site, stops in the tissue site, and withdraws out of the tissue site. A skin stabilizer device is provided that is suitable for stretching a surface of a tissue site. The skin stabilizer at least partially surrounds the penetrating member exit. A cartridge houses the penetrating member. The cartridge has first and second seals coupled to the penetrating member to maintain a sterile environment around a portion of the penetration member prior to penetrating member actuation. A user interface is configured to relay at least one of, penetrating member performance or a penetrating member setting.

In another embodiment of the present invention, a body fluid sampling system for use on a tissue site includes a drive force generator. A penetrating member is operatively coupled to the force generator. The force generator moves the member along a path out of a housing having a penetrating member exit, into the tissue site, stops in the tissue site, and withdraws out of the tissue site. A skin stabilizer device is provided that is suitable for stretching a surface of a tissue site. The skin stabilizer at least partially surrounds the penetrating member exit. A cartridge houses the penetrating member. The cartridge has first and second seals coupled to the penetrating member to maintain a sterile environment around a portion of the penetration member prior to penetrating member actuation. A human interface provides at least one output.

In another embodiment of the present invention, a body fluid sampling system for use on a tissue site includes a drive force generator. A penetrating member is operatively coupled to the force generator. The force generator moves the member along a path out of a housing having a penetrating member exit, into the tissue site, stops in the tissue site, and withdraws out of the tissue site. A cartridge houses the penetrating member. The cartridge has first and second seals coupled to the penetrating member to maintain a sterile environment around a portion of the penetration member prior to penetrating member actuation. A user interface is configured to relay at least one of, penetrating member performance or a penetrating member setting.

In another embodiment of the present invention, a body fluid sampling system for use on a tissue site includes a drive force generator. A penetrating member is operatively coupled to the force generator. The force generator moves the member along a path out of a housing having a penetrating member exit, into the tissue site, stops in the tissue site, and withdraws out of the tissue site. A cartridge houses the penetrating member. The cartridge has first and second seals coupled to the penetrating member to maintain a sterile environment around a portion of the penetration member prior to penetrating member actuation. A human interface provides at least one output.

In another embodiment of the present invention, a body fluid sampling system for use on a tissue site includes a drive force generator. A penetrating member is operatively coupled to the force generator. The force generator moves the member along a path out of a housing having a penetrating member exit, into the tissue site, stops in the tissue site, and withdraws out of the tissue site. An analyte detection member is positioned to receive fluid from a wound created by the penetrating member. The detection member is configured to determine a concentration of an analyte in the fluid using a sample of less than 1 µL of the fluid. A cartridge houses the penetrating member. The cartridge has first and second seals coupled to the penetrating member to maintain a sterile environment around a portion of the penetration member prior to penetrating member actuation. A user interface is configured to relay at least one of, penetrating member performance or a penetrating member setting.

In another embodiment of the present invention, a body fluid sampling system for use on a tissue site includes a drive force generator. A penetrating member is operatively coupled to the force generator. The force generator moves the member along a path out of a housing having a penetrating member exit, into the tissue site, stops in the tissue site, and withdraws out of the tissue site. An analyte detection member is positioned to receive fluid from a wound created by the penetrating member. The detection member is configured to determine a concentration of an analyte in the fluid using a sample of less than 1 µL of the fluid. A cartridge houses the penetrating member. The cartridge has first and second seals coupled to the penetrating member to maintain a sterile environment around a portion of the penetration member prior to penetrating member actuation. A human interface provides at least one output.

A further understanding of the nature and advantages of the invention will become apparent by reference to the remaining portions of the specification and drawings.

DESCRIPTION OF THE SPECIFIC EMBODIMENTS

Figure 1:
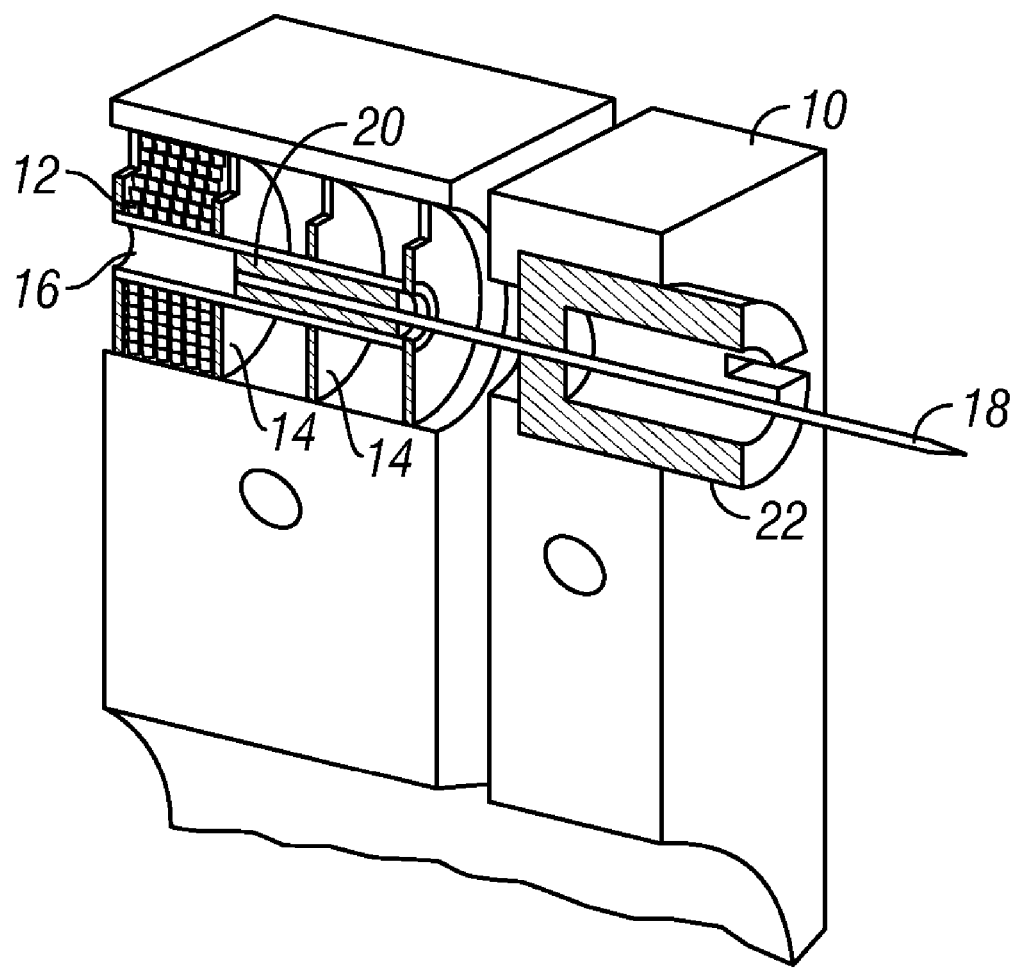
FIG. 1 illustrates an embodiment of a controllable force driver in the form of a cylindrical electric penetrating member driver using a coiled solenoid-type configuration.

The present invention provides a solution for body fluid sampling. Specifically, some embodiments of the present invention provides a penetrating member device for consistently creating a wound with spontaneous body fluid flow from a patient. The invention may be a multiple penetrating member device with an optional high density design. It may use penetrating members of smaller size than known penetrating members. The device may be used for multiple lancing events without having to remove a disposable from the device or for the user to handle sharps. The invention may provide improved sensing capabilities. At least some of these and other objectives described herein will be met by embodiments of the present invention.

It is to be understood that both the foregoing general description and the following detailed description are exemplary and explanatory only and are not restrictive of the invention, as claimed. It should be noted that, as used in the specification and the appended claims, the singular forms "a", "an" and "the" include plural referents unless the context clearly dictates otherwise. Thus, for example, reference to "a material" may include mixtures of materials, reference to "a chamber" may include multiple chambers, and the like. References cited herein are hereby incorporated by reference in their entirety, except to the extent that they conflict with teachings explicitly set forth in this specification.

In this specification and in the claims which follow, reference will be made to a number of terms which shall be defined to have the following meanings:

"Optional" or "optionally" means that the subsequently described circumstance may or may not occur, so that the description includes instances where the circumstance occurs and instances where it does not. For example, if a device optionally contains a feature for analyzing a blood sample, this means that the analysis feature may or may not be present, and, thus, the description includes structures wherein a device possesses the analysis feature and structures wherein the analysis feature is not present.

"Analyte detecting member" refers to any use, singly or in combination, of chemical test reagents and methods, electrical test circuits and methods, physical test components and methods, optical test components and methods, and biological test reagents and methods to yield information about a blood sample. Such methods are well known in the art and may be based on teachings of, e.g. Tietz Textbook of Clinical Chemistry, 3d Ed., Sec. V, pp. 776-78 (Burtis & Ashwood, Eds., W.B. Saunders Company, Philadelphia, 1999); U.S. Pat. No. 5,997,817 to Chrismore et al. (Dec. 7, 1999); U.S. Pat. No. 5,059,394 to Phillips et al. (Oct. 22, 1991); U.S. Pat. No. 5,001,054 to Wagner et al. (Mar. 19, 1991); and U.S. Pat. No. 4,392,933 to Nakamura et al. (Jul. 12, 1983), the teachings of which are hereby incorporated by reference, as well as others. Analyte detecting member may include tests in the sample test chamber that test electrochemical properties of the blood, or they may include optical means for sensing optical properties of the blood (e.g. oxygen saturation level), or they may include biochemical reagents (e.g. antibodies) to sense properties (e.g. presence of antigens) of the blood. The analyte detecting member may comprise biosensing or reagent material that will react with an analyte in blood (e.g. glucose) or other body fluid so that an appropriate signal correlating with the presence of the analyte is generated and can be read by the reader apparatus. By way of example and not limitation, analyte detecting member may "associated with", "mounted within", or "coupled to" a chamber or other structure when the analyte detecting member participates in the function of providing an appropriate signal about the blood sample to the reader device. Analyte detecting member may also include nanowire analyte detecting members as described herein. Analyte detecting member may use potentiometric, coulometric, or other method useful for detection of analyte levels.

The present invention may be used with a variety of different penetrating member drivers. It is contemplated that these penetrating member drivers may be spring based, solenoid based, magnetic driver based, nanomuscle based, or based on any other mechanism useful in moving a penetrating member along a path into tissue. It should be noted that the present invention is not limited by the type of driver used with the penetrating member feed mechanism. One suitable penetrating member driver for use with the present invention is shown in FIG. 1. This is an embodiment of a solenoid type electromagnetic driver that is capable of driving an iron core or slug mounted to the penetrating member assembly using a direct current (DC) power supply. The electromagnetic driver includes a driver coil pack that is divided into three separate coils along the path of the penetrating member, two end coils and a middle coil. Direct current is alternated to the coils to advance and retract the penetrating member. Although the driver coil pack is shown with three coils, any suitable number of coils may be used, for example, 4, 5, 6, 7 or more coils may be used.

Referring to the embodiment of FIG. 1, the stationary iron housing 10 may contain the driver coil pack with a first coil 12 flanked by iron spacers 14 which concentrate the magnetic flux at the inner diameter creating magnetic poles. The inner insulating housing 16 isolates the penetrating member 18 and iron core 20 from the coils and provides a smooth, low friction guide surface. The penetrating member guide 22 further centers the penetrating member 18 and iron core 20. The penetrating member 18 is protracted and retracted by alternating the current between the first coil 12, the middle coil, and the third coil to attract the iron core 20. Reversing the coil sequence and attracting the core and penetrating member back into the housing retracts the penetrating member. The penetrating member guide 22 also serves as a stop for the iron core 20 mounted to the penetrating member 18.

Figure 2A:
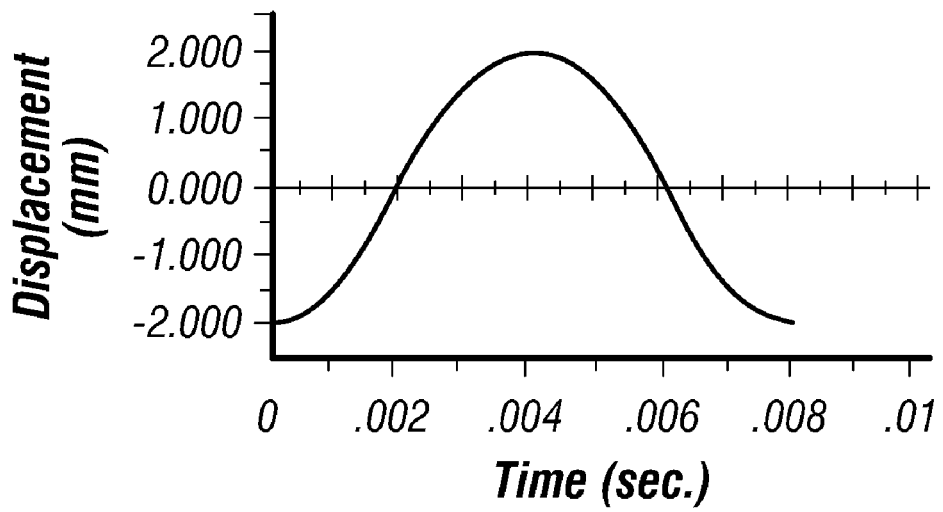
FIG. 2A illustrates a displacement over time profile of a penetrating member driven by a harmonic spring/mass system.
Figure 2B:
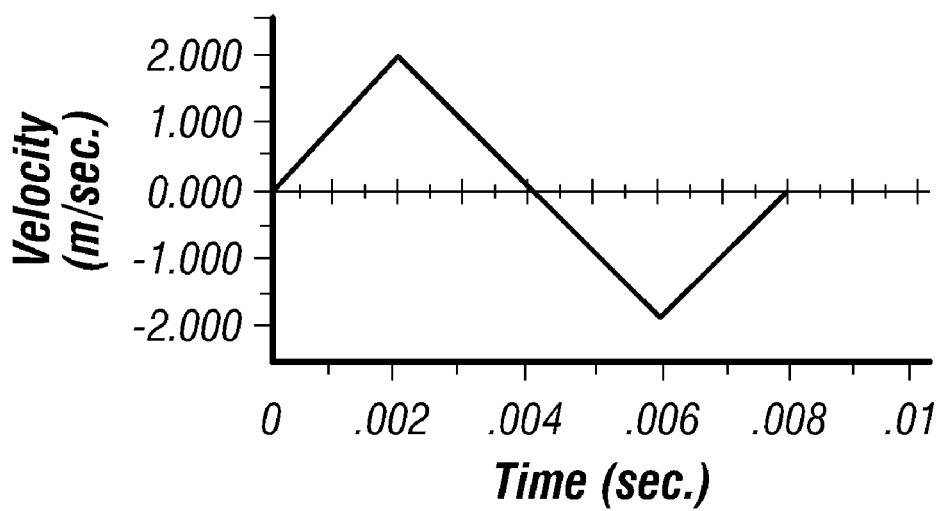
FIG. 2B illustrates the velocity over time profile of a penetrating member driver by a harmonic spring/mass system.
Figure 2C:
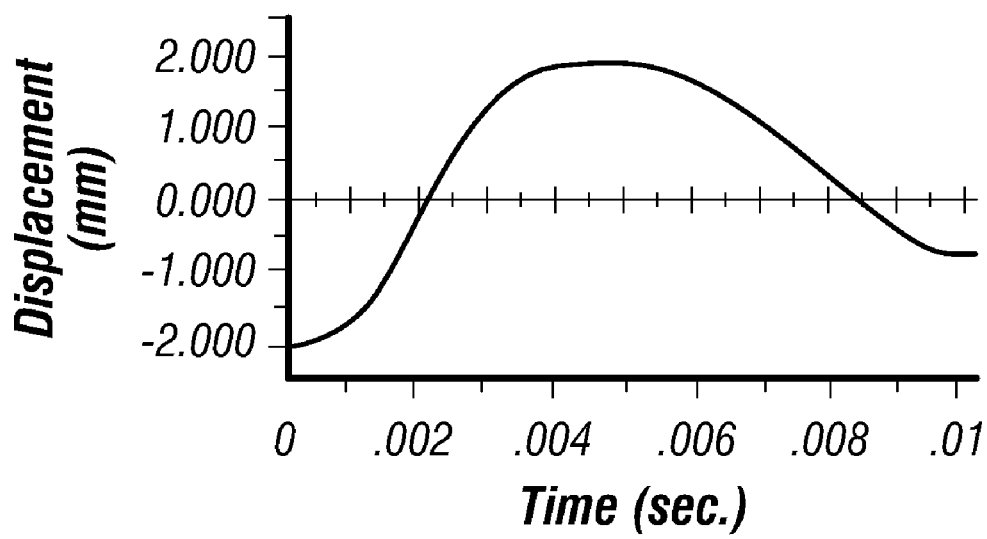
FIG. 2C illustrates a displacement over time profile of an embodiment of a controllable force driver.
Figure 2D:
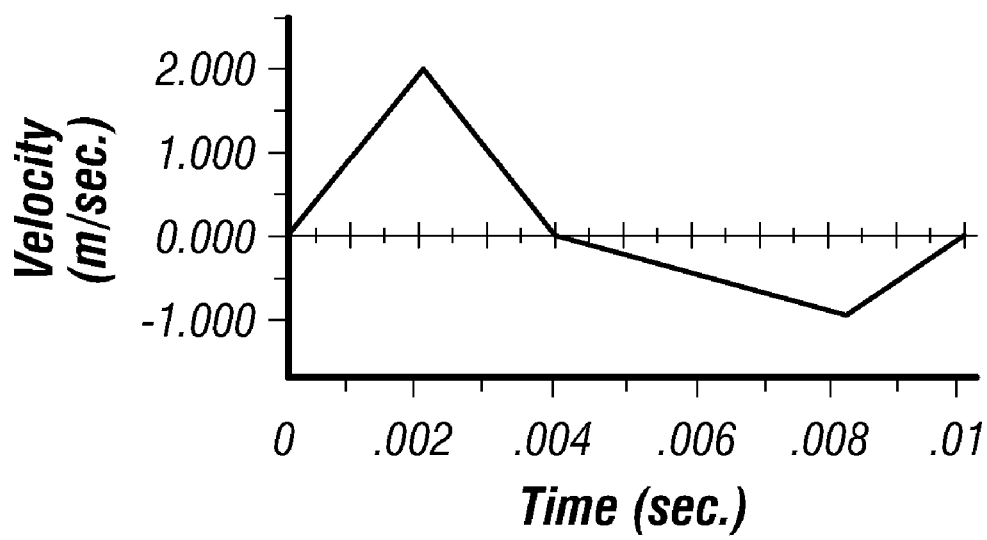
FIG. 2D illustrates a velocity over time profile of an embodiment of a controllable force driver.
Figure 3:
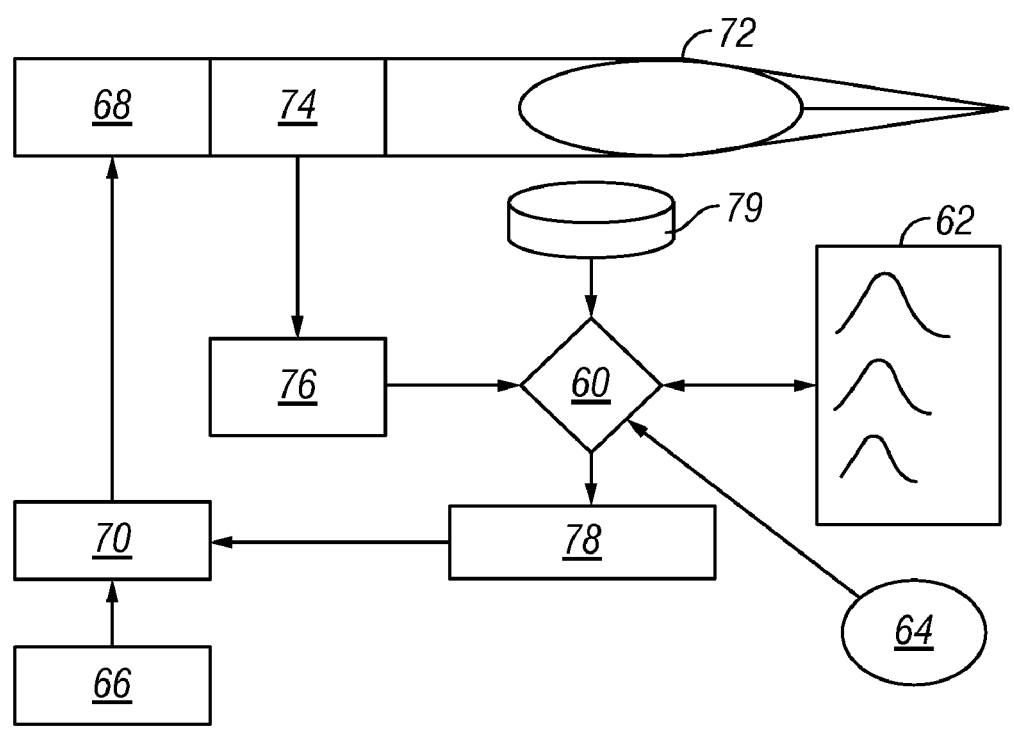
FIG. 3 is a diagrammatic view illustrating a controlled feed-back loop.

As discussed above, tissue penetration devices which employ spring or cam driving methods have a symmetrical or nearly symmetrical actuation displacement and velocity profiles on the advancement and retraction of the penetrating member as shown in FIGS. 2 and 3. In most of the available lancet devices, once the launch is initiated, the stored energy determines the velocity profile until the energy is dissipated. Controlling impact, retraction velocity, and dwell time of the penetrating member within the tissue can be useful in order to achieve a high success rate while accommodating variations in skin properties and minimize pain. Advantages can be achieved by taking into account of the fact that tissue dwell time is related to the amount of skin deformation as the penetrating member tries to puncture the surface of the skin and variance in skin deformation from patient to patient based on skin hydration.

In this embodiment, the ability to control velocity and depth of penetration may be achieved by use of a controllable force driver where feedback is an integral part of driver control. Such drivers can control either metal or polymeric penetrating members or any other type of tissue penetration element. The dynamic control of such a driver is illustrated in FIG. 2C which illustrates an embodiment of a controlled displacement profile and FIG. 2D which illustrates an embodiment of a the controlled velocity profile. These are compared to FIGS. 2A and 2B, which illustrate embodiments of displacement and velocity profiles, respectively, of a harmonic spring/mass powered driver. Reduced pain can be achieved by using impact velocities of greater than about 2 m/s entry of a tissue penetrating element, such as a lancet, into tissue. Other suitable embodiments of the penetrating member driver are described in commonly assigned, copending U.S. patent application Ser. No. 10/127,395, filed Apr. 19, 2002 and previously incorporated herein.

FIG. 3 illustrates the operation of a feedback loop using a processor 60. The processor 60 stores profiles 62 in non-volatile memory. A user inputs information 64 about the desired circumstances or parameters for a lancing event. The processor 60 selects a driver profile 62 from a set of alternative driver profiles that have been preprogrammed in the processor 60 based on typical or desired tissue penetration device performance determined through testing at the factory or as programmed in by the operator. The processor 60 may customize by either scaling or modifying the profile based on additional user input information 64. Once the processor has chosen and customized the profile, the processor 60 is ready to modulate the power from the power supply 66 to the penetrating member driver 68 through an amplifier 70. The processor 60 may measure the location of the penetrating member 72 using a position sensing mechanism 74 through an analog to digital converter 76 linear encoder or other such transducer. Examples of position sensing mechanisms have been described in the embodiments above and may be found in the specification for commonly assigned, copending U.S. patent application Ser. No. 10/127,395, filed Apr. 19, 2002 and previously incorporated herein. The processor 60 calculates the movement of the penetrating member by comparing the actual profile of the penetrating member to the predetermined profile. The processor 60 modulates the power to the penetrating member driver 68 through a signal generator 78, which may control the amplifier 70 so that the actual velocity profile of the penetrating member does not exceed the predetermined profile by more than a preset error limit. The error limit is the accuracy in the control of the penetrating member.

After the lancing event, the processor 60 can allow the user to rank the results of the lancing event. The processor 60 stores these results and constructs a database 80 for the individual user. Using the database 79, the processor 60 calculates the profile traits such as degree of painlessness, success rate, and blood volume for various profiles 62 depending on user input information 64 to optimize the profile to the individual user for subsequent lancing cycles. These profile traits depend on the characteristic phases of penetrating member advancement and retraction. The processor 60 uses these calculations to optimize profiles 62 for each user. In addition to user input information 64, an internal clock allows storage in the database 79 of information such as the time of day to generate a time stamp for the lancing event and the time between lancing events to anticipate the user's diurnal needs. The database stores information and statistics for each user and each profile that particular user uses.

In addition to varying the profiles, the processor 60 can be used to calculate the appropriate penetrating member diameter and geometry suitable to realize the blood volume required by the user. For example, if the user requires about 1-5 microliter volume of blood, the processor 60 may select a 200 micron diameter penetrating member to achieve these results. For each class of lancet, both diameter and lancet tip geometry, is stored in the processor 60 to correspond with upper and lower limits of attainable blood volume based on the predetermined displacement and velocity profiles.

The lancing device is capable of prompting the user for information at the beginning and the end of the lancing event to more adequately suit the user. The goal is to either change to a different profile or modify an existing profile. Once the profile is set, the force driving the penetrating member is varied during advancement and retraction to follow the profile. The method of lancing using the lancing device comprises selecting a profile, lancing according to the selected profile, determining lancing profile traits for each characteristic phase of the lancing cycle, and optimizing profile traits for subsequent lancing events.

Figure 4:
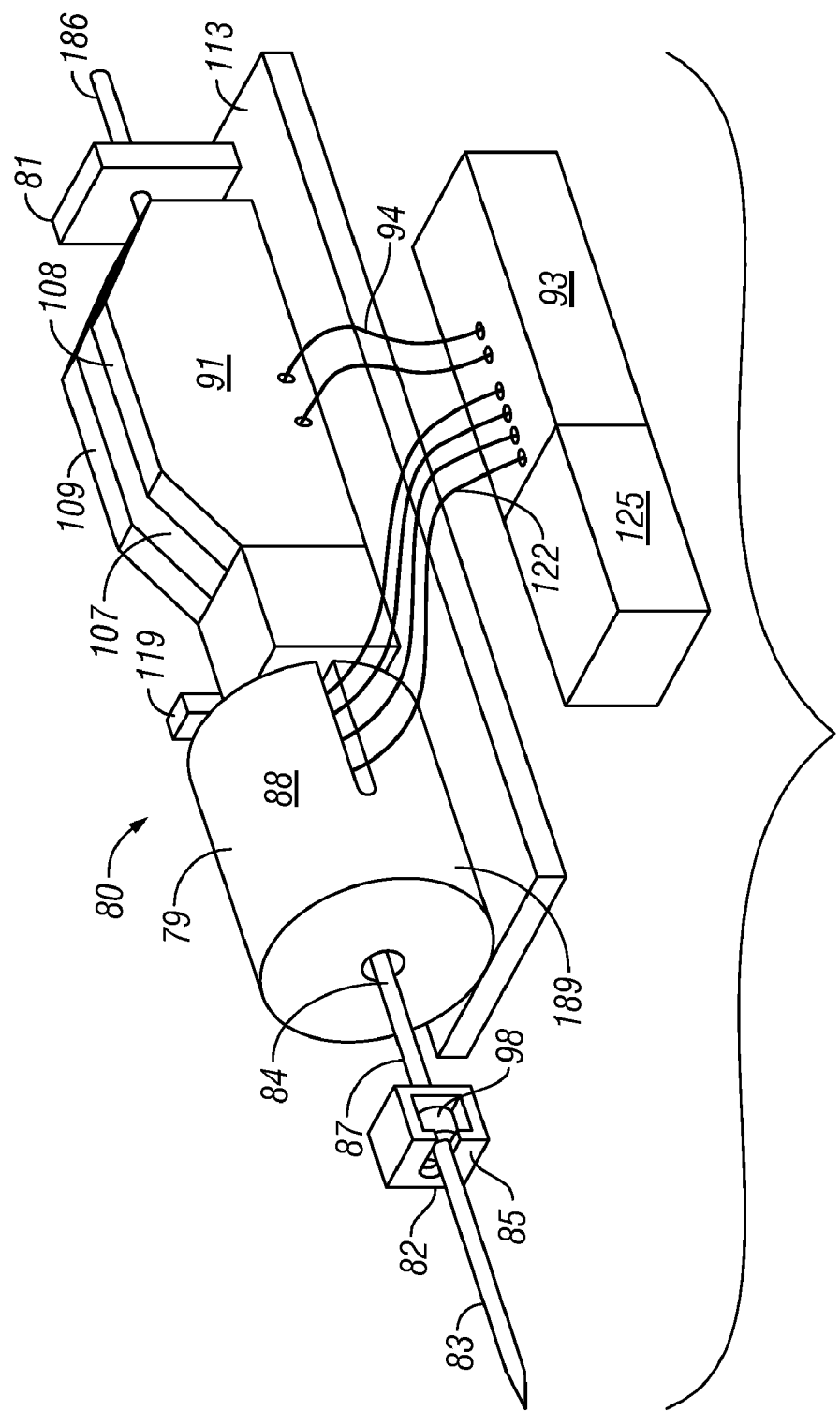
FIG. 4 is a perspective view of a tissue penetration device having features of the invention.

FIG. 4 illustrates an embodiment of a tissue penetration device, more specifically, a lancing device 80 that includes a controllable driver 179 coupled to a tissue penetration element. The lancing device 80 has a proximal end 81 and a distal end 82. At the distal end 82 is the tissue penetration element in the form of a penetrating member 83, which is coupled to an elongate coupler shaft 84 by a drive coupler 85. The elongate coupler shaft 84 has a proximal end 86 and a distal end 87. A driver coil pack 88 is disposed about the elongate coupler shaft 84 proximal of the penetrating member 83. A position sensor 91 is disposed about a proximal portion 92 of the elongate coupler shaft 84 and an electrical conductor 94 electrically couples a processor 93 to the position sensor 91. The elongate coupler shaft 84 driven by the driver coil pack 88 controlled by the position sensor 91 and processor 93 form the controllable driver, specifically, a controllable electromagnetic driver.

Figure 5:
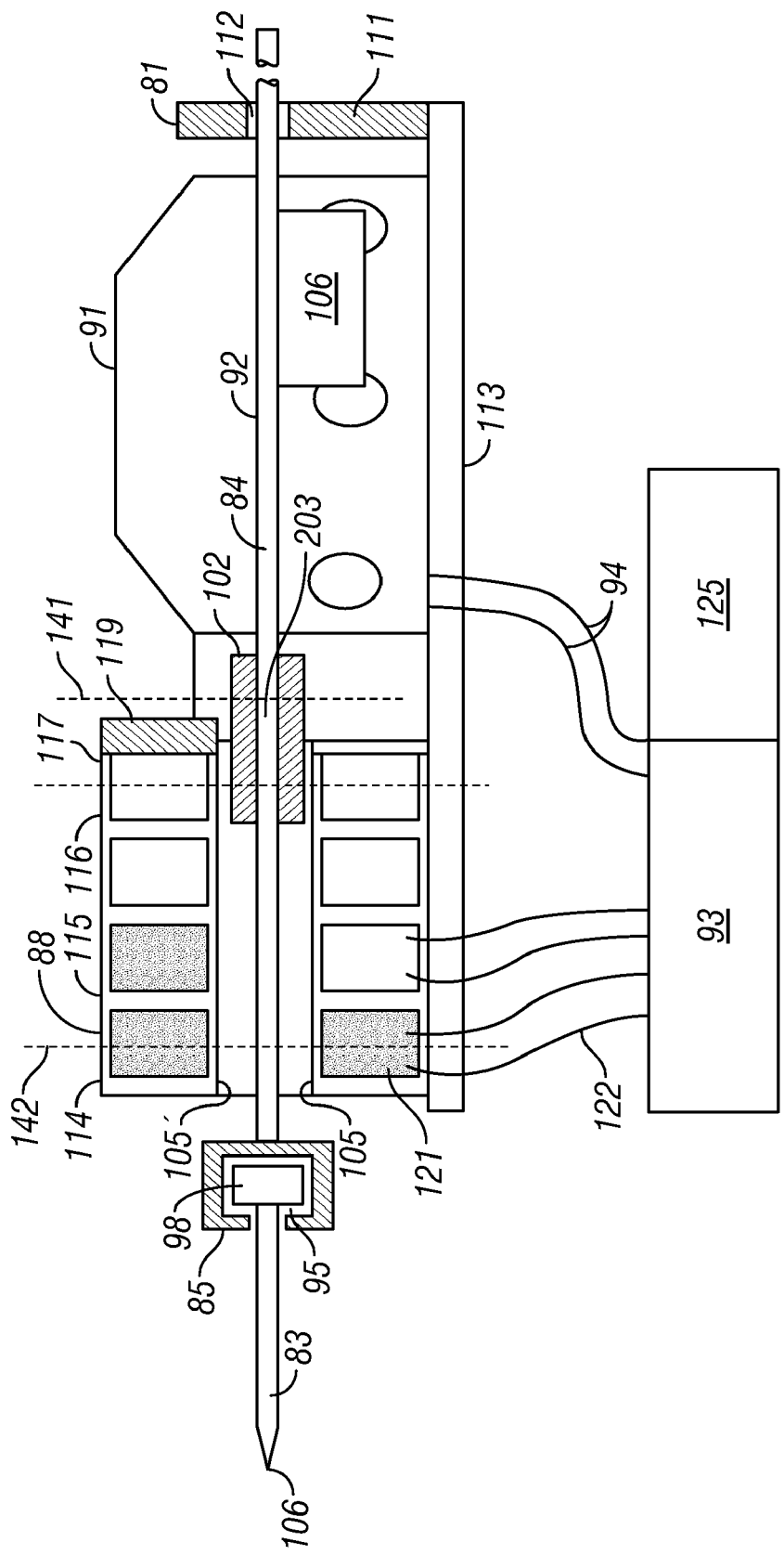
FIG. 5 is an elevation view in partial longitudinal section of the tissue penetration device of FIG. 4.

Referring to FIG. 5, the lancing device 80 can be seen in more detail, in partial longitudinal section. The penetrating member 83 has a proximal end 95 and a distal end 96 with a sharpened point at the distal end 96 of the penetrating member 83 and a drive head 98 disposed at the proximal end 95 of the penetrating member 83. A penetrating member shaft 201 is disposed between the drive head 98 and the sharpened point 97. The penetrating member shaft 201 may be comprised of stainless steel, or any other suitable material or alloy and have a transverse dimension of about 0.1 to about 0.4 mm. The penetrating member shaft may have a length of about 3 mm to about 50 mm, specifically, about 15 mm to about 20 mm. The drive head 98 of the penetrating member 83 is an enlarged portion having a transverse dimension greater than a transverse dimension of the penetrating member shaft 201 distal of the drive head 98. This configuration allows the drive head 98 to be mechanically captured by the drive coupler 85. The drive head 98 may have a transverse dimension of about 0.5 to about 2 mm.

A magnetic member 102 is secured to the elongate coupler shaft 84 proximal of the drive coupler 85 on a distal portion 203 of the elongate coupler shaft 84. The magnetic member 102 is a substantially cylindrical piece of magnetic material having an axial lumen 204 extending the length of the magnetic member 102. The magnetic member 102 has an outer transverse dimension that allows the magnetic member 102 to slide easily within an axial lumen 105 of a low friction, possibly lubricious, polymer guide tube 105' disposed within the driver coil pack 88. The magnetic member 102 may have an outer transverse dimension of about 1.0 to about 5.0 mm, specifically, about 2.3 to about 2.5 mm. The magnetic member 102 may have a length of about 3.0 to about 5.0 mm, specifically, about 4.7 to about 4.9 mm. The magnetic member 102 can be made from a variety of magnetic materials including ferrous metals such as ferrous steel, iron, ferrite, or the like. The magnetic member 102 may be secured to the distal portion 203 of the elongate coupler shaft 84 by a variety of methods including adhesive or epoxy bonding, welding, crimping or any other suitable method.

Proximal of the magnetic member 102, an optical encoder flag 206 is secured to the elongate coupler shaft 84. The optical encoder flag 206 is configured to move within a slot 107 in the position sensor 91. The slot 107 of the position sensor 91 is formed between a first body portion 108 and a second body portion 109 of the position sensor 91. The slot 107 may have separation width of about 1.5 to about 2.0 mm. The optical encoder flag 206 can have a length of about 14 to about 18 mm, a width of about 3 to about 5 mm and a thickness of about 0.04 to about 0.06 mm.

The optical encoder flag 206 interacts with various optical beams generated by LEDs disposed on or in the position sensor body portions 108 and 109 in a predetermined manner. The interaction of the optical beams generated by the LEDs of the position sensor 91 generates a signal that indicates the longitudinal position of the optical flag 206 relative to the position sensor 91 with a substantially high degree of resolution. The resolution of the position sensor 91 may be about 200 to about 400 cycles per inch, specifically, about 350 to about 370 cycles per inch. The position sensor 91 may have a speed response time (position/time resolution) of 0 to about 120,000 Hz, where one dark and light stripe of the flag constitutes one Hertz, or cycle per second. The position of the optical encoder flag 206 relative to the magnetic member 102, driver coil pack 88 and position sensor 91 is such that the optical encoder 91 can provide precise positional information about the penetrating member 83 over the entire length of the penetrating member's power stroke.

An optical encoder that is suitable for the position sensor 91 is a linear optical incremental encoder, model HEDS 9200, manufactured by Agilent Technologies. The model HEDS 9200 may have a length of about 20 to about 30 mm, a width of about 8 to about 12 mm, and a height of about 9 to about 11 mm. Although the position sensor 91 illustrated is a linear optical incremental encoder, other suitable position sensor embodiments could be used, provided they posses the requisite positional resolution and time response. The HEDS 9200 is a two channel device where the channels are 90 degrees out of phase with each other. This results in a resolution of four times the basic cycle of the flag. These quadrature outputs make it possible for the processor to determine the direction of penetrating member travel. Other suitable position sensors include capacitive encoders, analog reflective sensors, such as the reflective position sensor discussed above, and the like.

A coupler shaft guide 111 is disposed towards the proximal end 81 of the lancing device 80. The guide 111 has a guide lumen 112 disposed in the guide 111 to slidingly accept the proximal portion 92 of the elongate coupler shaft 84. The guide 111 keeps the elongate coupler shaft 84 centered horizontally and vertically in the slot 102 of the optical encoder 91.

The driver coil pack 88, position sensor 91 and coupler shaft guide 111 are all secured to a base 113. The base 113 is longitudinally coextensive with the driver coil pack 88, position sensor 91 and coupler shaft guide 111. The base 113 can take the form of a rectangular piece of metal or polymer, or may be a more elaborate housing with recesses, which are configured to accept the various components of the lancing device 80.

As discussed above, the magnetic member 102 is configured to slide within an axial lumen 105 of the driver coil pack 88. The driver coil pack 88 includes a most distal first coil 114, a second coil 115, which is axially disposed between the first coil 114 and a third coil 116, and a proximal-most fourth coil 117. Each of the first coil 114, second coil 115, third coil 116 and fourth coil 117 has an axial lumen. The axial lumens of the first through fourth coils are configured to be coaxial with the axial lumens of the other coils and together form the axial lumen 105 of the driver coil pack 88 as a whole. Axially adjacent each of the coils 114-117 is a magnetic disk or washer 118 that augments completion of the magnetic circuit of the coils 114-117 during a lancing cycle of the device 80. The magnetic washers 118 of the embodiment of FIG. 5 are made of ferrous steel but could be made of any other suitable magnetic material, such as iron or ferrite. The outer shell 89 of the driver coil pack 88 is also made of iron or steel to complete the magnetic path around the coils and between the washers 118. The magnetic washers 118 have an outer diameter commensurate with an outer diameter of the driver coil pack 88 of about 4.0 to about 8.0 mm. The magnetic washers 118 have an axial thickness of about 0.05, to about 0.4 mm, specifically, about 0.15 to about 0.25 mm.

Wrapping or winding an elongate electrical conductor 121 about an axial lumen until a sufficient number of windings have been achieved forms the coils 114-117. The elongate electrical conductor 121 is generally an insulated solid copper wire with a small outer transverse dimension of about 0.06 mm to about 0.88 mm, specifically, about 0.3 mm to about 0.5 mm. In one embodiment, 32 gauge copper wire is used for the coils 114-117. The number of windings for each of the coils 114-117 of the driver pack 88 may vary with the size of the coil, but for some embodiments each coil 114-117 may have about 30 to about 80 turns, specifically, about 50 to about 60 turns. Each coil 114-117 can have an axial length of about 1.0 to about 3.0 mm, specifically, about 1.8 to about 2.0 mm. Each coil 114-117 can have an outer transverse dimension or diameter of about 4.0, to about 2.0 mm, specifically, about 9.0 to about 12.0 mm. The axial lumen 105 can have a transverse dimension of about 1.0 to about 3.0 mm.

It may be advantageous in some driver coil 88 embodiments to replace one or more of the coils with permanent magnets, which produce a magnetic field similar to that of the coils when the coils are activated. In particular, it may be desirable in some embodiments to replace the second coil 115, the third coil 116 or both with permanent magnets. In addition, it may be advantageous to position a permanent magnet at or near the proximal end of the coil driver pack in order to provide fixed magnet zeroing function for the magnetic member (Adams magnetic Products 23A0002 flexible magnet material (800) 747-7543).

A permanent bar magnet 119 disposed on the proximal end of the driver coil pack 88. As shown in FIG. 5, the bar magnet 119 is arranged so as to have one end disposed adjacent the travel path of the magnetic member 102 and has a polarity configured so as to attract the magnetic member 102 in a centered position with respect to the bar magnet 119. Note that the polymer guide tube 105' can be configured to extend proximally to insulate the inward radial surface of the bar magnet 119 from an outer surface of the magnetic member 102. This arrangement allows the magnetic member 119 and thus the elongate coupler shaft 84 to be attracted to and held in a zero point or rest position without the consumption of electrical energy from the power supply 125.

Having a fixed zero or start point for the elongate coupler shaft 84 and penetrating member 83 may be useful to properly controlling the depth of penetration of the penetrating member 83 as well as other lancing parameters. This can be because some methods of depth penetration control for a controllable driver measure the acceleration and displacement of the elongate coupler shaft 84 and penetrating member 83 from a known start position. If the distance of the penetrating member tip 96 from the target tissue is known, acceleration and displacement of the penetrating member is known and the start position of the penetrating member is know, the time and position of tissue contact and depth of penetration can be determined by the processor 93.

Figure 23A:
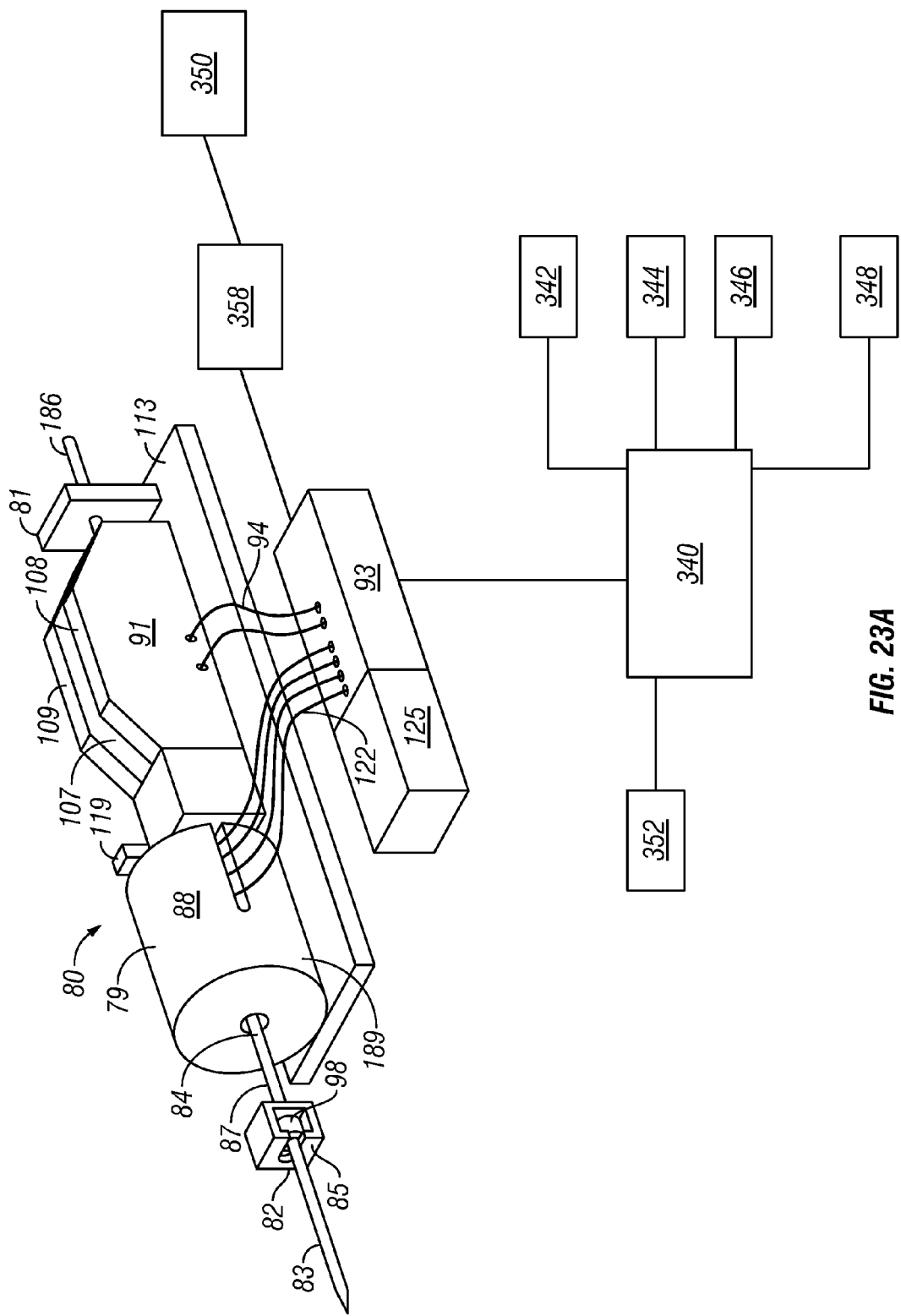
FIG. 23A shows an embodiment of a device with a user interface.

Any number of configurations for a magnetic bar 119 can be used for the purposes discussed above. In particular, a second permanent bar magnet (not shown) could be added to the proximal end of the driver coil pack 88 with the magnetic fields of the two bar magnets configured to complement each other. In addition, a disc magnet 119' could be used as illustrated in FIG. 23(a). The disc magnet is shown disposed at the proximal end of the driver coiled pack 88 with a polymer non-magnetic disc disposed between the proximal-most coil 117 and the disc magnet and positions the disc magnet away from the proximal end of the proximal-most coil 117. The polymer non-magnetic disc spacer is used so that the magnetic member 102 can be centered in a zero or start position slightly proximal of the proximal-most coil 117 of the driver coil pack 88. This allows the magnetic member to be attracted by the proximal-most coil 117 at the initiation of the lancing cycle instead of being passive in the forward drive portion of the lancing cycle.

An inner lumen of the polymer non-magnetic disc can be configured to allow the magnetic member 102 to pass axially there through while an inner lumen of the disc magnet can be configured to allow the elongate coupler shaft 84 to pass through but not large enough for the magnetic member 102 to pass through. This results in the magnetic member 102 being attracted to the disc magnet and coming to rest with the proximal surface of the magnetic member 102 against a distal surface of the disc magnet. This arrangement provides for a positive and repeatable stop for the magnetic member, and hence the penetrating member.

Typically, when the electrical current in the coils 114-117 of the driver coil pack 88 is off, a magnetic member 102 made of soft iron is attracted to the bar magnet 119 or disc magnet. The magnetic field of the driver coil pack 88 and the bar magnet 119 or the disc magnet, or any other suitable magnet, can be configured such that when the electrical current in the coils 114-117 is turned on, the leakage magnetic field from the coils 114-117 has the same polarity as the bar magnet 119 or the disc magnet This results in a magnetic force that repels the magnetic member 102 from the bar magnet 119 or disc magnet and attracts the magnetic member 102 to the activated coils 114-117. For this configuration, the bar magnet 119 or disc magnet thus act to facilitate acceleration of the magnetic member 102 as opposed to working against the acceleration.

Electrical conductors 122 couple the driver coil pack 88 with the processor 93 which can be configured or programmed to control the current flow in the coils 114-117 of the driver coil pack 88 based on position feedback from the position sensor 91, which is coupled to the processor 93 by electrical conductors 94. A power source 125 is electrically coupled to the processor 93 and provides electrical power to operate the processor 93 and power the coil driver pack 88. The power source 125 may be one or more batteries that provide direct current power to the 93 processor.

Figure 29:
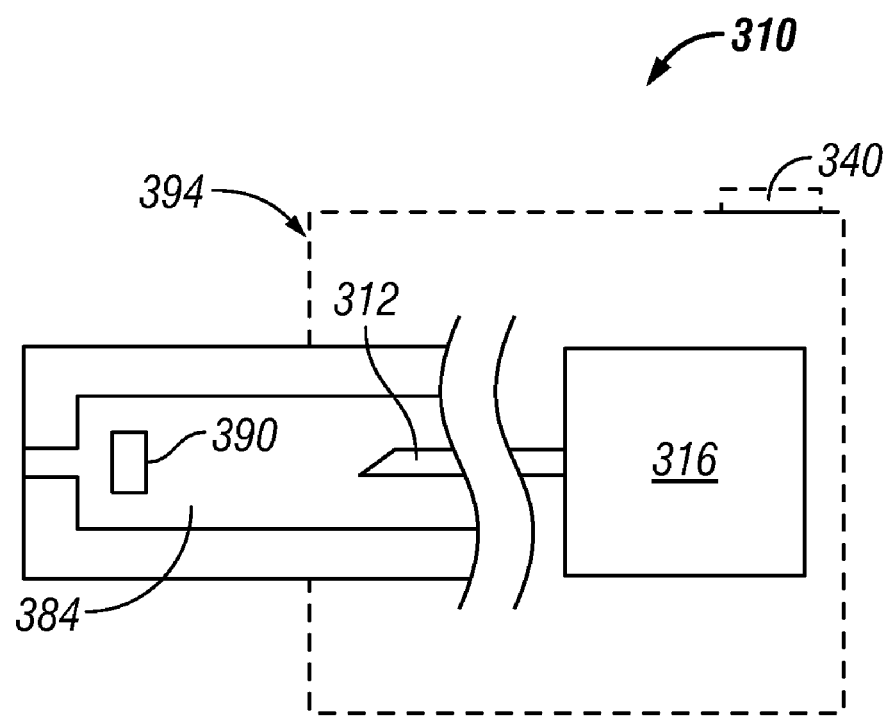
FIG. 29 shows a cutaway view of another embodiment of a system for sampling body fluid.

Referring to FIGS. 29A-29C, a flow diagram is shown that describes the operations performed by the processor 93 in controlling the penetrating member 83 of the lancing device 80 discussed above during an operating cycle. FIGS. 30-36 illustrate the interaction of the penetrating member 83 and skin 133 of the patient's finger 134 during an operation cycle of the penetrating member device 83. The processor 93 operates under control of programming steps that are stored in an associated memory. When the programming steps are executed, the processor 93 performs operations as described herein. Thus, the programming steps implement the functionality of the operations described with respect to the flow diagram of FIG. 29. The processor 93 can receive the programming steps from a program product stored in recordable media, including a direct access program product storage device such as a hard drive or flash ROM, a removable program product storage device such as a floppy disk, or in any other manner known to those of skill in the art. The processor 93 can also download the programming steps through a network connection or serial connection.

Figure 6A:
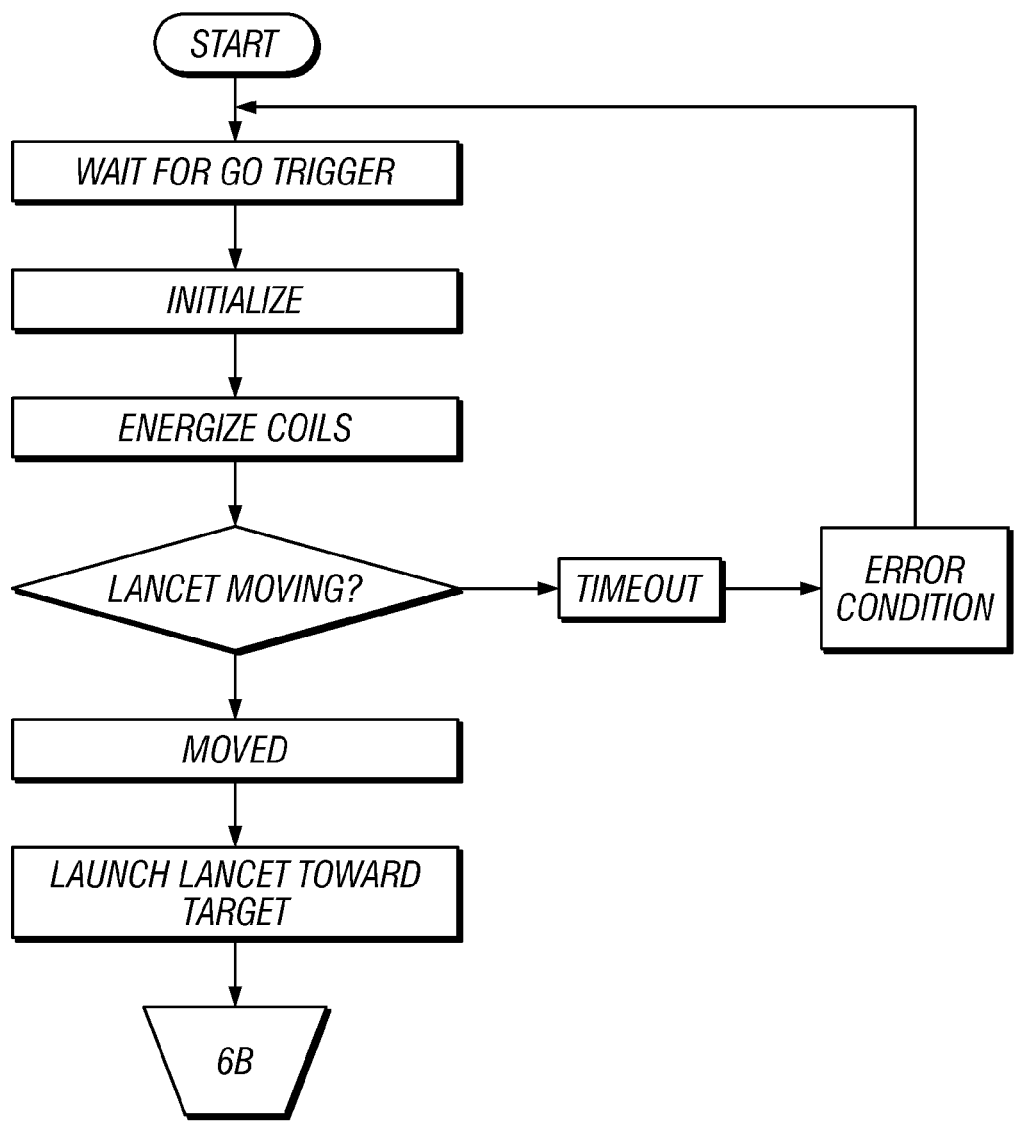
FIGS. 6A-6C show a flowchart illustrating a penetrating member control method.

In the first operation, represented by the flow diagram box numbered 245 in FIG. 6A, the processor 93 initializes values that it stores in memory relating to control of the penetrating member, such as variables that it uses to keep track of the controllable driver 179 during movement. For example, the processor may set a clock value to zero and a penetrating member position value to zero or to some other initial value. The processor 93 may also cause power to be removed from the coil pack 88 for a period of time, such as for about 10 ms, to allow any residual flux to dissipate from the coils.

In the initialization operation, the processor 93 also causes the penetrating member to assume an initial stationary position. When in the initial stationary position, the penetrating member 83 is typically fully retracted such that the magnetic member 102 is positioned substantially adjacent the fourth coil 117 of the driver coil pack 88, shown in FIG. 5 above. The processor 93 can move the penetrating member 83 to the initial stationary position by pulsing an electrical current to the fourth coil 117 to thereby attract the magnetic member 102 on the penetrating member 83 to the fourth coil 117. Alternatively, the magnetic member can be positioned in the initial stationary position by virtue of a permanent magnet, such as bar magnet 119, disc magnet or any other suitable magnet as discussed above with regard to the tissue penetration device illustrated in FIGS. 20 and 21.

In the next operation, represented by the flow diagram box numbered 247, the processor 93 energizes one or more of the coils in the coil pack 88. This should cause the penetrating member 83 to begin to move (i.e., achieve a non-zero speed) toward the skin target 133. The processor 93 then determines whether or not the penetrating member is indeed moving. The processor 93 can determine whether the penetrating member 83 is moving by monitoring the position of the penetrating member 83 to determine whether the position changes over time. The processor 93 can monitor the position of the penetrating member 83 by keeping track of the position of the optical encoder flag 106 secured to the elongate coupler shaft 84 wherein the encoder 91 produces a signal coupled to the processor 93 that indicates the spatial position of the penetrating member 83.

If the processor 93 determines (via timeout without motion events) that the penetrating member 83 is not moving, then the process proceeds to the operation, where the processor deems that an error condition is present. This means that some error in the system is causing the penetrating member 83 not to move. The error may be mechanical, electrical, or software related. For example, the penetrating member 83 may be stuck in the stationary position because something is impeding its movement.

Figure 7:
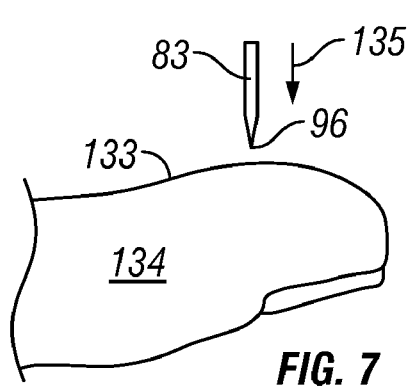
FIG. 7 is a diagrammatic view of a patient's finger and a penetrating member tip moving toward the skin of the finger.

If the processor 93 determines that the penetrating member 83 is indeed moving (a "Yes" result from the decision box numbered 249), then the process proceeds to the operation represented by the flow diagram box numbered 257. In this operation, the processor 93 causes the penetrating member 83 to continue to accelerate and launch toward the skin target 133, as indicated by the arrow 135 in FIG. 7. The processor 93 can achieve acceleration of the penetrating member 83 by sending an electrical current to an appropriate coil 114-117 such that the coil 114-117 exerts an attractive magnetic launching force on the magnetic member 102 and causes the magnetic member 102 and the penetrating member 83 coupled thereto to move in a desired direction. For example, the processor 93 can cause an electrical current to be sent to the third coil 116 so that the third coil 116 attracts the magnetic member 102 and causes the magnetic member 102 to move from a position adjacent the fourth coil 117 toward the third coil 116. The processor preferably determines which coil 114-117 should be used to attract the magnetic member 102 based on the position of the magnetic member 102 relative to the coils 114-117. In this manner, the processor 93 provides a controlled force to the penetrating member that controls the movement of the penetrating member.

During this operation, the processor 93 periodically or continually monitors the position and/or velocity of the penetrating member 83. In keeping track of the velocity and position of the penetrating member 83 as the penetrating member 83 moves towards the patient's skin 133 or other tissue, the processor 93 also monitors and adjusts the electrical current to the coils 114-117. In some embodiments, the processor 93 applies current to an appropriate coil 114-117 such that the penetrating member 83 continues to move according to a desired direction and acceleration. In the instant case, the processor 93 applies current to the appropriate coil 114-117 that will cause the penetrating member 83 to continue to move in the direction of the patient's skin 133 or other tissue to be penetrated.

The processor 93 may successively transition the current between coils 114-117 so that as the magnetic member 102 moves past a particular coil 114-117, the processor 93 then shuts off current to that coil 114-117 and then applies current to another coil 114-117 that will attract the magnetic member 102 and cause the magnetic member 102 to continue to move in the desired direction. In transitioning current between the coils 114-117, the processor 93 can take into account various factors, including the speed of the penetrating member 83, the position of the penetrating member 83 relative to the coils 114-117, the number of coils 114-117, and the level of current to be applied to the coils 114-117 to achieve a desired speed or acceleration.

Figure 6B:
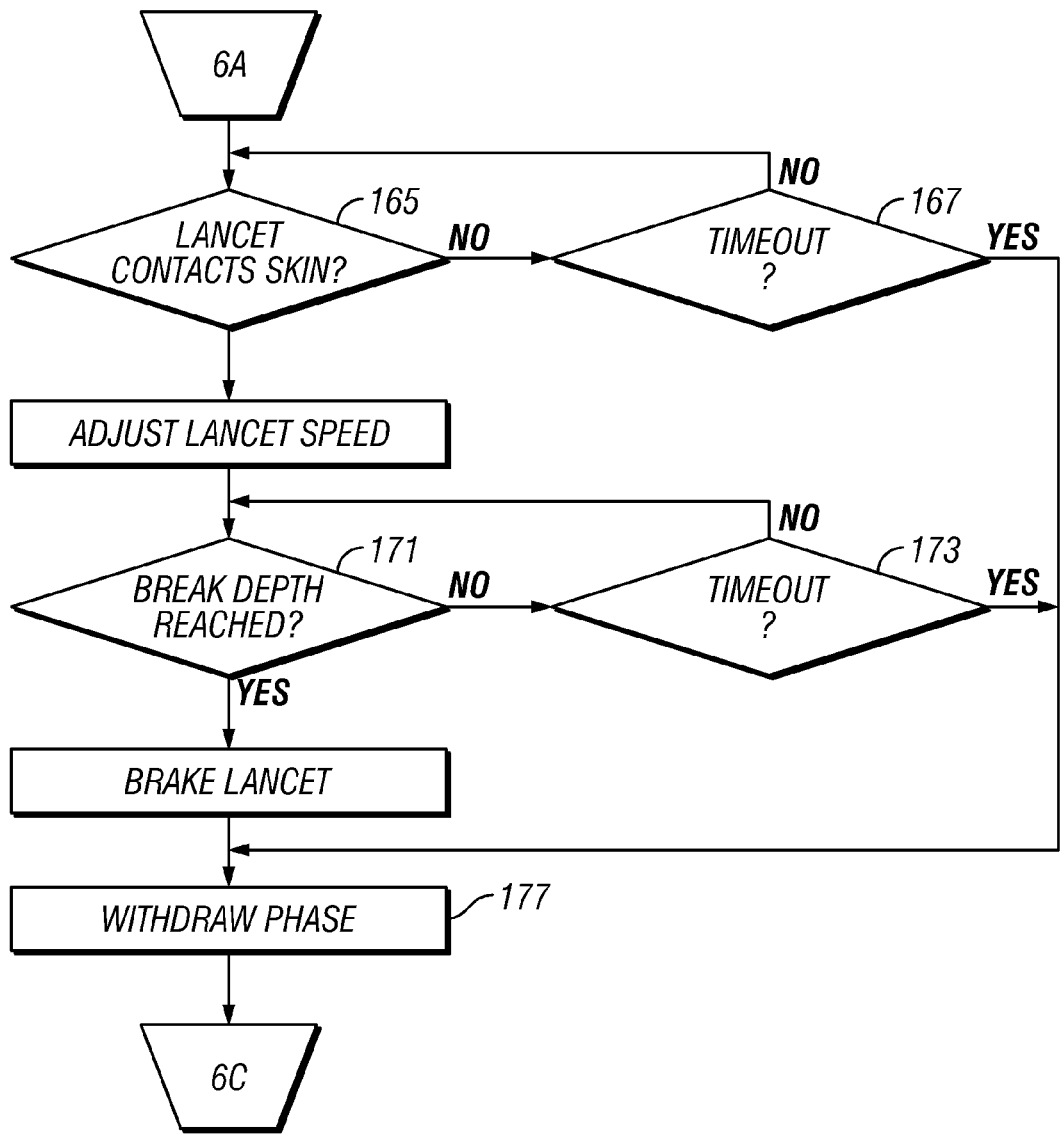
Figure 8:
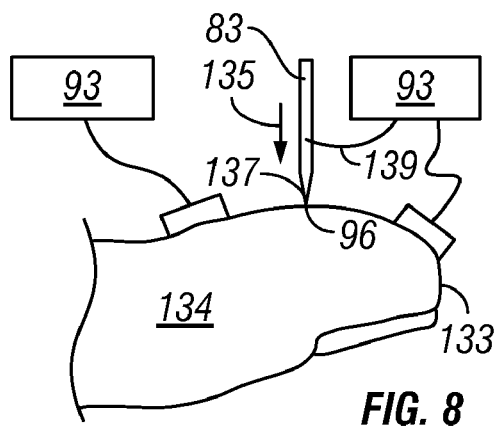
FIG. 8 is a diagrammatic view of a patient's finger and the penetrating member tip making contact with the skin of a patient's finger.

In the next operation, the processor 93 determines whether the cutting or distal end tip 96 of the penetrating member 83 has contacted the patient's skin 133, as shown in FIG. 8 and in FIG. 6B. The processor 93 may determine whether the penetrating member 83 has made contact with the target tissue 133 by a variety of methods, including some that rely on parameters which are measured prior to initiation of a lancing cycle and other methods that are adaptable to use during a lancing cycle without any predetermined parameters.

In one embodiment, the processor 93 determines that the skin has been contacted when the end tip 96 of the penetrating member 83 has moved a predetermined distance with respect to its initial position. If the distance from the tip 261 of the penetrating member 83 to the target tissue 133 is known prior to initiation of penetrating member 83 movement, the initial position of the penetrating member 83 is fixed and known, and the movement and position of the penetrating member 83 can be accurately measured during a lancing cycle, then the position and time of penetrating member contact can be determined.

This method requires an accurate measurement of the distance between the penetrating member tip 96 and the patient's skin 133 when the penetrating member 83 is in the zero time or initial position. This can be accomplished in a number of ways. One way is to control all of the mechanical parameters that influence the distance from the penetrating member tip 96 to the patient's tissue or a surface of the lancing device 80 that will contact the patient's skin 133. This could include the start position of the magnetic member 102, magnetic path tolerance, magnetic member 102 dimensions, driver coil pack 88 location within the lancing device 80 as a whole, length of the elongate coupling shaft 84, placement of the magnetic member 102 on the elongate coupling shaft 84, length of the penetrating member 83 etc.

If all these parameters, as well as others can be suitably controlled in manufacturing with a tolerance stack-up that is acceptable, then the distance from the penetrating member tip 96 to the target tissue 133 can be determined at the time of manufacture of the lancing device 80. The distance could then be programmed into the memory of the processor 93. If an adjustable feature is added to the lancing device 80, such as an adjustable length elongate coupling shaft 84, this can accommodate variations in all of the parameters noted above, except length of the penetrating member 83. An electronic alternative to this mechanical approach would be to calibrate a stored memory contact point into the memory of the processor 93 during manufacture based on the mechanical parameters described above.

In another embodiment, moving the penetrating member tip 96 to the target tissue 133 very slowly and gently touching the skin 133 prior to actuation can accomplish the distance from the penetrating member tip 96 to the tissue 133. The position sensor can accurately measure the distance from the initialization point to the point of contact, where the resistance to advancement of the penetrating member 83 stops the penetrating member movement. The penetrating member 83 is then retracted to the initialization point having measured the distance to the target tissue 133 without creating any discomfort to the user.

In another embodiment, the processor 93 may use software to determine whether the penetrating member 83 has made contact with the patient's skin 133 by measuring for a sudden reduction in velocity of the penetrating member 83 due to friction or resistance imposed on the penetrating member 83 by the patient's skin 133. The optical encoder 91 measures displacement of the penetrating member 83. The position output data provides input to the interrupt input of the processor 93. The processor 93 also has a timer capable of measuring the time between interrupts. The distance between interrupts is known for the optical encoder 91, so the velocity of the penetrating member 83 can be calculated by dividing the distance between interrupts by the time between the interrupts.

This method requires that velocity losses to the penetrating member 83 and elongate coupler 84 assembly due to friction are known to an acceptable level so that these velocity losses and resulting deceleration can be accounted for when establishing a deceleration threshold above which contact between penetrating member tip 96 and target tissue 133 will be presumed. This same concept can be implemented in many ways. For example, rather than monitoring the velocity of the penetrating member 83, if the processor 93 is controlling the penetrating member driver in order to maintain a fixed velocity, the power to the driver 88 could be monitored. If an amount of power above a predetermined threshold is required in order to maintain a constant velocity, then contact between the tip of the penetrating member 96 and the skin 133 could be presumed.

In yet another embodiment, the processor 93 determines skin 133 contact by the penetrating member 83 by detection of an acoustic signal produced by the tip 96 of the penetrating member 83 as it strikes the patient's skin 133. Detection of the acoustic signal can be measured by an acoustic detector 136 placed in contact with the patient's skin 133 adjacent a penetrating member penetration site 137, as shown in FIG. 8. Suitable acoustic detectors 136 include piezo electric transducers, microphones and the like. The acoustic detector 136 transmits an electrical signal generated by the acoustic signal to the processor 93 via electrical conductors 138. In another embodiment, contact of the penetrating member 83 with the patient's skin 133 can be determined by measurement of electrical continuity in a circuit that includes the penetrating member 83, the patient's finger 134 and an electrical contact pad 240 that is disposed on the patient's skin 133 adjacent the contact site 137 of the penetrating member 83, as shown in FIG. 8. In this embodiment, as soon as the penetrating member 83 contacts the patient's skin 133, the circuit 139 is completed and current flows through the circuit 139. Completion of the circuit 139 can then be detected by the processor 93 to confirm skin 133 contact by the penetrating member 83.

If the penetrating member 83 has not contacted the target skin 133, then the process proceeds to a timeout operation, in FIG. 6B. In the timeout operation, the processor 93 waits a predetermined time period. If the timeout period has not yet elapsed (a "No" outcome from the decision box 167), then the processor continues to monitor whether the penetrating member has contacted the target skin 133. The processor 93 preferably continues to monitor the position and speed of the penetrating member 83, as well as the electrical current to the appropriate coil 114-117 to maintain the desired penetrating member 83 movement.

If the timeout period elapses without the penetrating member 83 contacting the skin (a "Yes" output from the decision box 167), then it is deemed that the penetrating member 83 will not contact the skin and the process proceeds to a withdraw phase, where the penetrating member is withdrawn away from the skin 133, as discussed more fully below. The penetrating member 83 may not have contacted the target skin 133 for a variety of reasons, such as if the patient removed the skin 133 from the lancing device or if something obstructed the penetrating member 83 prior to it contacting the skin.

The processor 93 may also proceed to the withdraw phase prior to skin contact for other reasons. For example, at some point after initiation of movement of the penetrating member 83, the processor 93 may determine that the forward acceleration of the penetrating member 83 towards the patient's skin 133 should be stopped or that current to all coils 114-117 should be shut down. This can occur, for example, if it is determined that the penetrating member 83 has achieved sufficient forward velocity, but has not yet contacted the skin 133. In one embodiment, the average penetration velocity of the penetrating member 83 from the point of contact with the skin to the point of maximum penetration may be about 2.0 to about 10.0 m/s, specifically, about 3.8 to about 4.2 m/s. In another embodiment, the average penetration velocity of the penetrating member may be from about 2 to about 8 meters per second, specifically, about 2 to about 4 m/s.

The processor 93 can also proceed to the withdraw phase if it is determined that the penetrating member 83 has fully extended to the end of the power stroke of the operation cycle of lancing procedure. In other words, the process may proceed to withdraw phase when an axial center 141 of the magnetic member 102 has moved distal of an axial center 142 of the first coil 114 as show in FIG. 5. In this situation, any continued power to any of the coils 114-117 of the driver coil pack 88 serves to decelerate the magnetic member 102 and thus the penetrating member 83. In this regard, the processor 93 considers the length of the penetrating member 83 (which can be stored in memory) the position of the penetrating member 83 relative to the magnetic member 102, as well as the distance that the penetrating member 83 has traveled.

With reference again to the decision box 165 in FIG. 6B, if the processor 93 determines that the penetrating member 83 has contacted the skin 133 (a "Yes" outcome from the decision box 165), then the processor 93 can adjust the speed of the penetrating member 83 or the power delivered to the penetrating member 83 for skin penetration to overcome any frictional forces on the penetrating member 83 in order to maintain a desired penetration velocity of the penetrating member. The flow diagram box numbered 167 represents this.

Figure 9:
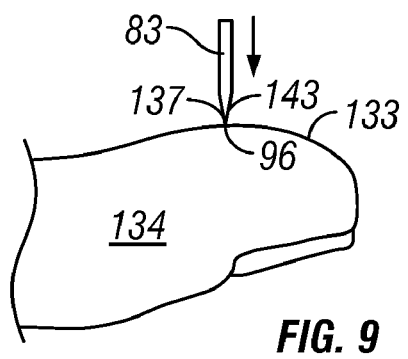
FIG. 9 is a diagrammatic view of the penetrating member tip depressing the skin of a patient's finger.
Figure 10:
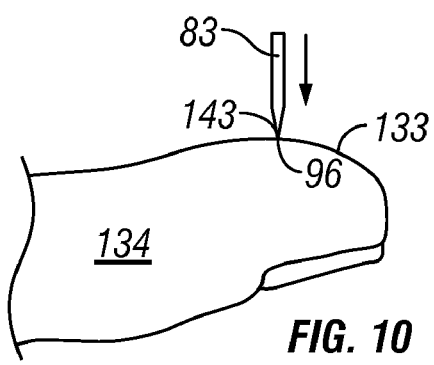
FIG. 10 is a diagrammatic view of the penetrating member tip further depressing the skin of a patient's finger.
Figure 11:
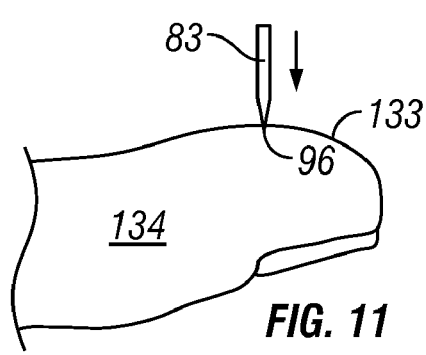
FIG. 11 is a diagrammatic view of the penetrating member tip penetrating the skin of a patient's finger.
Figure 24:
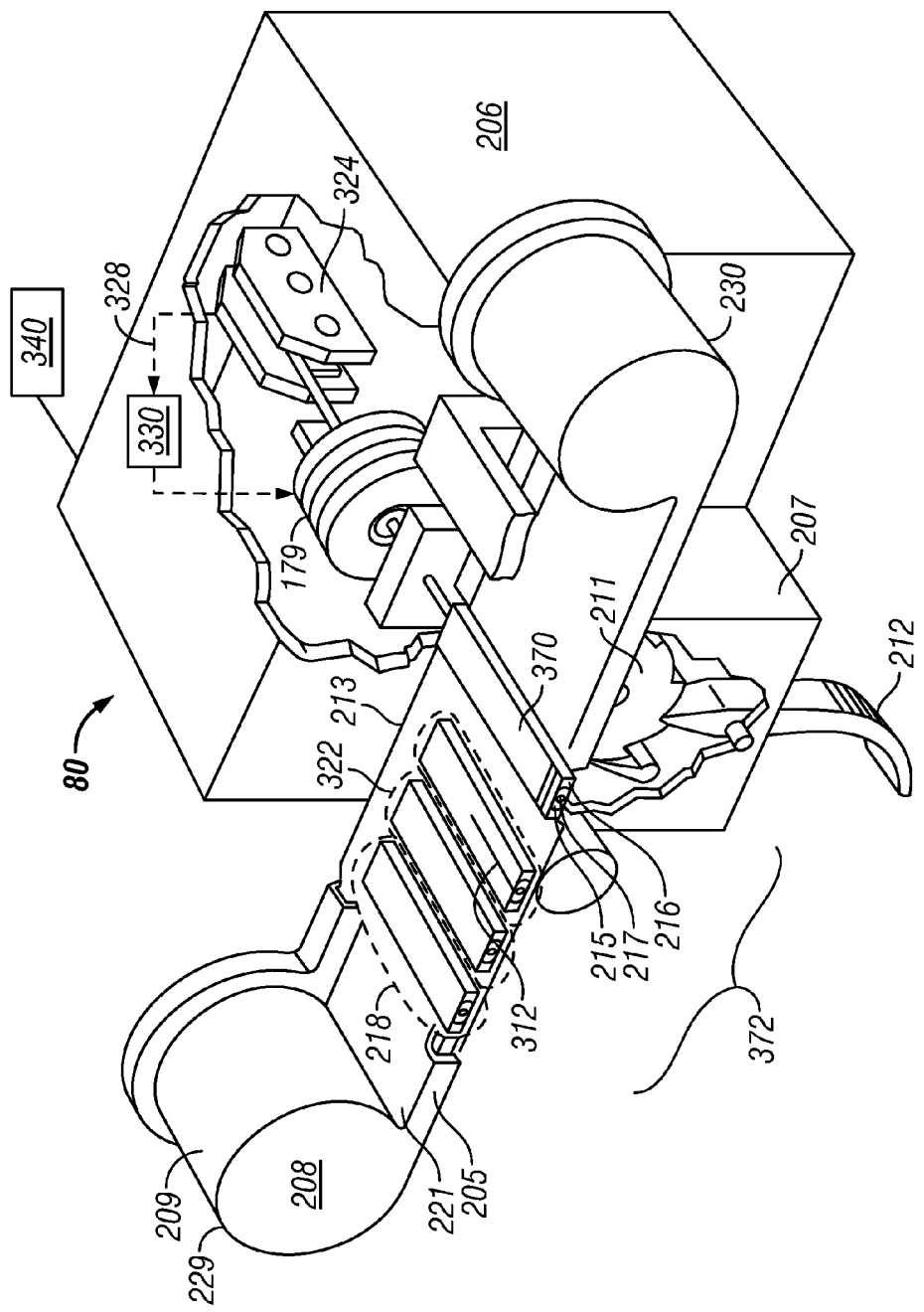
FIG. 24 is a cut away view of a system for sampling body fluid.
Figure 32:
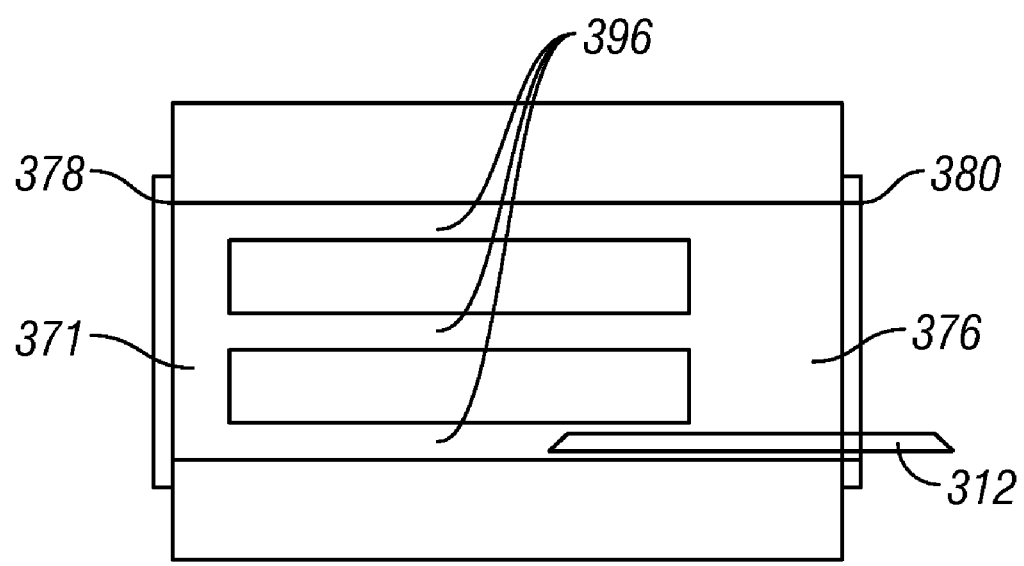
FIG. 32 is a cut away view of a cartridge according to the present invention.

As the velocity of the penetrating member 83 is maintained after contact with the skin 133, the distal tip 96 of the penetrating member 83 will first begin to depress or tent the contacted skin 137 and the skin 133 adjacent the penetrating member 83 to form a tented portion 243 as shown in FIG. 9 and further shown in FIG. 10. As the penetrating member 83 continues to move in a distal direction or be driven in a distal direction against the patient's skin 133, the penetrating member 83 will eventually begin to penetrate the skin 133, as shown in FIG. 11. Once penetration of the skin 133 begins, the static force at the distal tip 96 of the penetrating member 83 from the skin 133 will become a dynamic cutting force, which is generally less than the static tip force. As a result in the reduction of force on the distal tip 96 of the penetrating member 83 upon initiation of cutting, the tented portion 243 of the skin 133 adjacent the distal tip 96 of the penetrating member 83 which had been depressed as shown in FIGS. 32 and 24 will spring back as shown in FIG. 11.

In the next operation, represented by the decision box numbered 171 in FIG. 6B, the processor 93 determines whether the distal end 96 of the penetrating member 83 has reached a brake depth. The brake depth is the skin penetration depth for which the processor 93 determines that deceleration of the penetrating member 83 is to be initiated in order to achieve a desired final penetration depth 144 of the penetrating member 83 as show in FIG. 12. The brake depth may be pre-determined and programmed into the processor's memory, or the processor 93 may dynamically determine the brake depth during the actuation. The amount of penetration of the penetrating member 83 in the skin 133 of the patient may be measured during the operation cycle of the penetrating member device 80. In addition, as discussed above, the penetration depth suitable for successfully obtaining a useable sample can depend on the amount of tenting of the skin 133 during the lancing cycle. The amount of tenting of the patient's skin 133 can in turn depend on the tissue characteristics of the patient such as elasticity, hydration etc. A method for determining these characteristics is discussed below with regard to skin 133 tenting measurements during the lancing cycle and illustrated in FIGS. 37-41.

Penetration measurement can be carried out by a variety of methods that are not dependent on measurement of tenting of the patient's skin. In one embodiment, the penetration depth of the penetrating member 83 in the patient's skin 133 is measured by monitoring the amount of capacitance between the penetrating member 83 and the patient's skin 133. In this embodiment, a circuit includes the penetrating member 83, the patient's finger 134, the processor 93 and electrical conductors connecting these elements. As the penetrating member 83 penetrates the patient's skin 133, the greater the amount of penetration, the greater the surface contact area between the penetrating member 83 and the patient's skin 133. As the contact area increases, so does the capacitance between the skin 133 and the penetrating member 83. The increased capacitance can be easily measured by the processor 93 using methods known in the art and penetration depth can then be correlated to the amount of capacitance. The same method can be used by measuring the electrical resistance between the penetrating member 83 and the patient's skin.

If the brake depth has not yet been reached, then a "No" results from the decision box 171 and the process proceeds to the timeout operation represented by the flow diagram box numbered 173. In the timeout operation, the processor 93 waits a predetermined time period. If the timeout period has not yet elapsed (a "No" outcome from the decision box 173), then the processor continues to monitor whether the brake depth has been reached. If the timeout period elapses without the penetrating member 83 achieving the brake depth (a "Yes" output from the decision box 173), then the processor 93 deems that the penetrating member 83 will not reach the brake depth and the process proceeds to the withdraw phase, which is discussed more fully below. This may occur, for example, if the penetrating member 83 is stuck at a certain depth.

Figure 13:
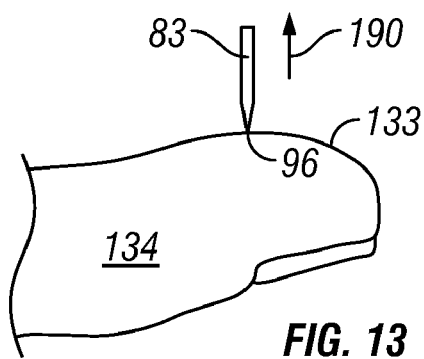
FIG. 13 is a diagrammatic view of the penetrating member tip withdrawing from the skin of a patient's finger.
Figure 26:
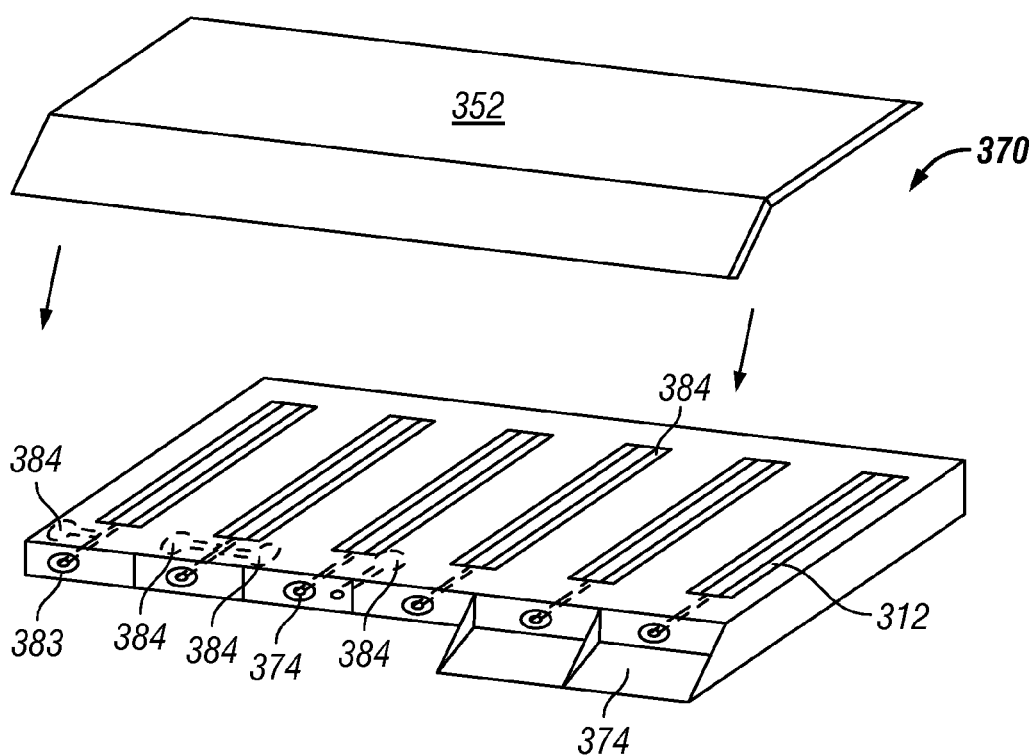
FIG. 26 is an exploded view of a cartridge having multiple penetrating members for use with a system for sampling body fluid.
Figure 33:
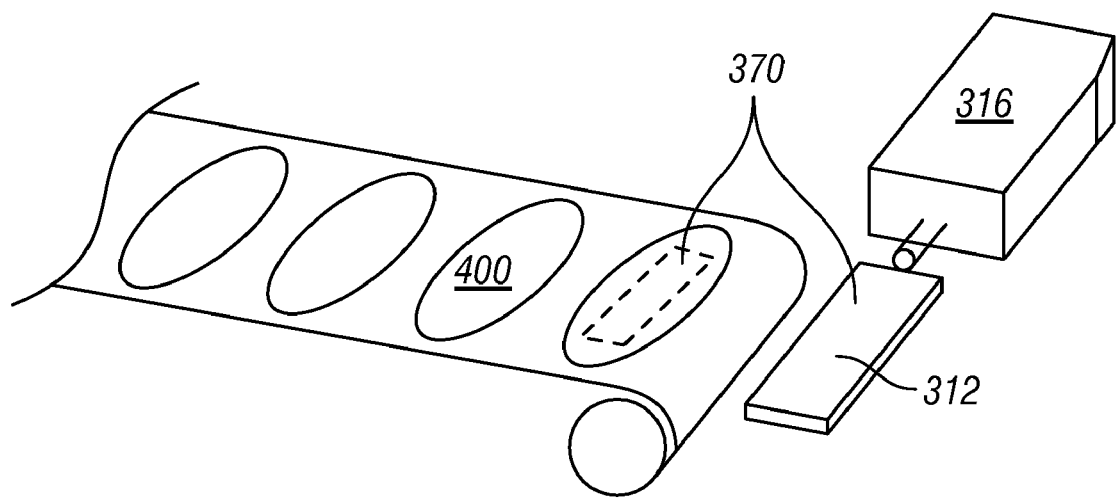
FIGS. 33-34 show views of a body sampling system using multiple cartridges.

With reference again to the decision box numbered 171 in FIG. 6B, if the penetrating member does reach the brake depth (a "Yes" result), then the process proceeds to the operation represented by the flow diagram box numbered 275. In this operation, the processor 93 causes a braking force to be applied to the penetrating member to thereby reduce the speed of the penetrating member 83 to achieve a desired amount of final skin penetration depth 144, as shown in FIG. 26. Note that FIGS. 32 and 33 illustrate the penetrating member making contact with the patient's skin and deforming or depressing the skin prior to any substantial penetration of the skin. The speed of the penetrating member 83 is preferably reduced to a value below a desired threshold and is ultimately reduced to zero. The processor 93 can reduce the speed of the penetrating member 83 by causing a current to be sent to a 114-117 coil that will exert an attractive braking force on the magnetic member 102 in a proximal direction away from the patient's tissue or skin 133, as indicated by the arrow 190 in FIG. 13. Such a negative force reduces the forward or distally oriented speed of the penetrating member 83. The processor 93 can determine which coil 114-117 to energize based upon the position of the magnetic member 102 with respect to the coils 114-117 of the driver coil pack 88, as indicated by the position sensor 91.

Figure 6C:
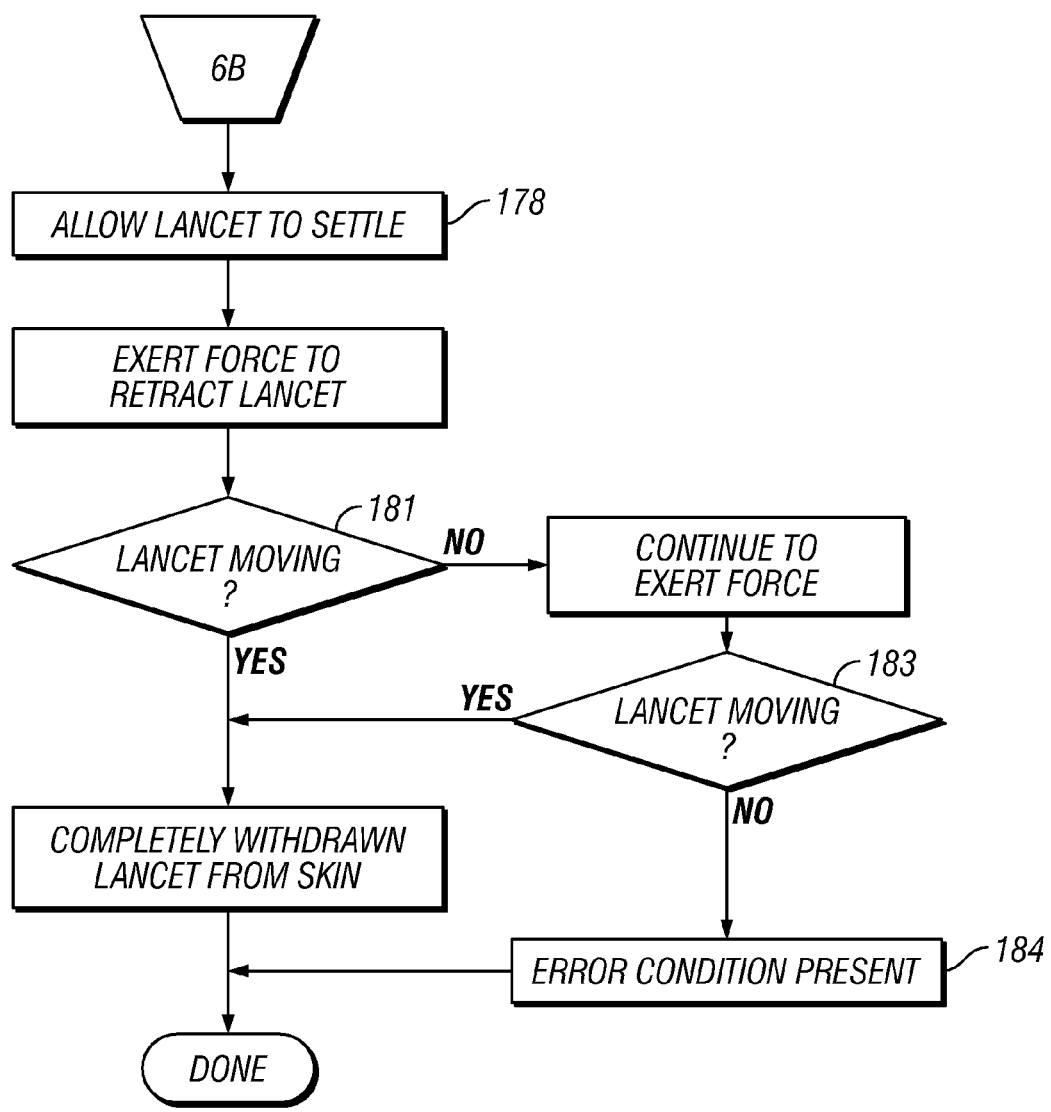
Figure 12:
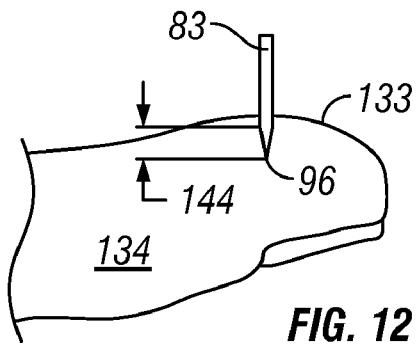
FIG. 12 is a diagrammatic view of the penetrating member tip penetrating the skin of a patient's finger to a desired depth.

In the next operation, the process proceeds to the withdraw phase, as represented by the flow diagram box numbered 177. The withdraw phase begins with the operation represented by the flow diagram box numbered 178 in FIG. 6C. Here, the processor 93 allows the penetrating member 83 to settle at a position of maximum skin penetration 144, as shown in FIG. 12. In this regard, the processor 93 waits until any motion in the penetrating member 83 (due to vibration from impact and spring energy stored in the skin, etc.) has stopped by monitoring changes in position of the penetrating member 83. The processor 93 preferably waits until several milliseconds (ms), such as on the order of about 8 ms, have passed with no changes in position of the penetrating member 83. This is an indication that movement of the penetrating member 83 has ceased entirely. In some embodiments, the penetrating member may be allowed to settle for about 1 to about 2000 milliseconds, specifically, about 50 to about 200 milliseconds. For other embodiments, the settling time may be about 1 to about 200 milliseconds.

Figure 14:
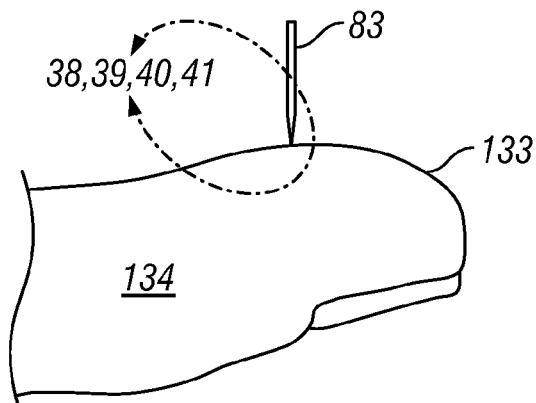
FIGS. 14-18 illustrate a method of tissue penetration that may measure elastic recoil of the skin.

It is at this stage of the lancing cycle that a software method can be used to measure the amount of tenting of the patient's skin 133 and thus determine the skin 133 characteristics such as elasticity, hydration and others. Referring to FIGS. 37-41, a penetrating member 83 is illustrated in various phases of a lancing cycle with target tissue 133. FIG. 14 shows tip 96 of penetrating member 83 making initial contact with the skin 133 at the point of initial impact.

Figure 15:
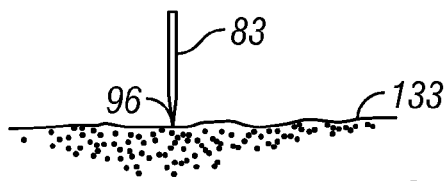
Figure 16:
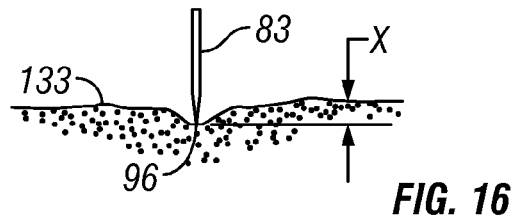
Figure 17:
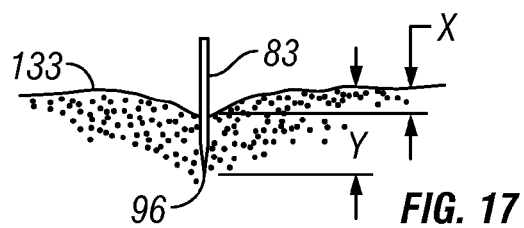

FIG. 15 illustrates an enlarged view of the penetrating member 83 making initial contact with the tissue 133 shown in FIG. 14. In FIG. 16, the penetrating member tip 96 has depressed or tented the skin 133 prior to penetration over a distance of X, as indicated by the arrow labeled X in FIG. 16. In FIG. 17, the penetrating member 83 has reached the full length of the cutting power stroke and is at maximum displacement. In this position, the penetrating member tip 96 has penetrated the tissue 133 a distance of Y, as indicated by the arrow labeled Y in FIG. 16. As can be seen from comparing FIG. 15 with FIG. 17, the penetrating member tip 96 was displaced a total distance of X plus Y from the time initial contact with the skin 133 was made to the time the penetrating member tip 96 reached its maximum extension as shown in FIG. 17. However, the penetrating member tip 96 has only penetrated the skin 133 a distance Y because of the tenting phenomenon.

Figure 18:
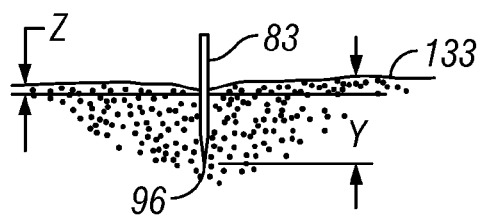

At the end of the power stroke of the penetrating member 83, as discussed above with regard to box 179 of FIG. 6C, the processor 93 allows the penetrating member to settle for about 8 msec. It is during this settling time that the skin 133 rebounds or relaxes back to approximately its original configuration prior to contact by the penetrating member 83 as shown in FIG. 18. The penetrating member tip 96 is still buried in the skin to a depth of Y, as shown in FIG. 18, however the elastic recoil of the tissue has displaced the penetrating member rearward or retrograde to the point of inelastic tenting that is indicated by the arrows Z in FIG. 18. During the rearward displacement of the penetrating member 83 due to the elastic tenting of the tissue 133, the processor reads and stores the position data generated by the position sensor 91 and thus measures the amount of elastic tenting, which is the difference between X and Z.

Figure 19:
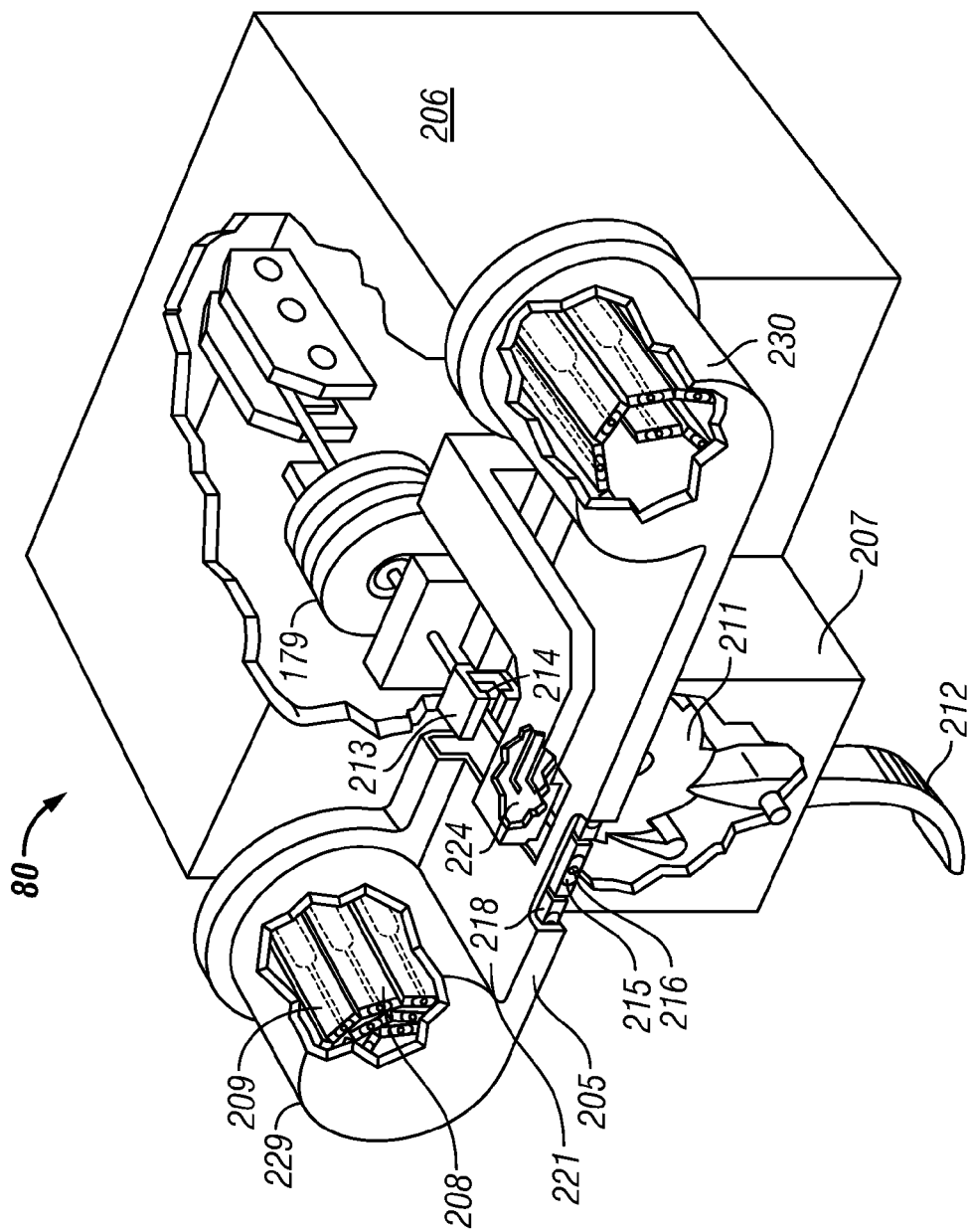
FIG. 19 is a perspective view in partial section of a tissue penetration sampling device with a cartridge of sampling modules.

Referring to FIG. 19, a tissue penetration sampling device 80 is shown with the controllable driver 179 of FIG. 4 coupled to a sampling module cartridge 205 and disposed within a driver housing 206. A ratchet drive mechanism 207 is secured to the driver housing 206, coupled to the sampling module cartridge 205 and configured to advance a sampling module belt 208 within the sampling module cartridge 205 so as to allow sequential use of each sampling module 209 in the sampling module belt 208. The ratchet drive mechanism 207 has a drive wheel 211 configured to engage the sampling modules 209 of the sampling module belt 208. The drive wheel 211 is coupled to an actuation lever 212 that advances the drive wheel 211 in increments of the width of a single sampling module 209. A T-slot drive coupler 213 is secured to the elongated coupler shaft 84.

A sampling module 209 is loaded and ready for use with the drive head 98 of the penetrating member 83 of the sampling module 209 loaded in the T-slot 214 of the drive coupler 213. A sampling site 215 is disposed at the distal end 216 of the sampling module 209 disposed about a penetrating member exit port 217. The distal end 216 of the sampling module 209 is exposed in a module window 218, which is an opening in a cartridge cover 221 of the sampling module cartridge 205. This allows the distal end 216 of the sampling module 209 loaded for use to be exposed to avoid contamination of the cartridge cover 221 with blood from the lancing process.

A reader module 222 is disposed over a distal portion of the sampling module 209 that is loaded in the drive coupler 213 for use and has two contact brushes 224 that are configured to align and make electrical contact with analyte detecting member contacts 225 of the sampling module 209 as shown in FIG. 77. With electrical contact between the analyte detecting member contacts 225 and contact brushes 224, the processor 93 of the controllable driver 179 can read a signal from an analytical region 226 of the sampling module 209 after a lancing cycle is complete and a blood sample enters the analytical region 226 of the sampling module 209. The contact brushes 224 can have any suitable configuration that will allow the sampling module belt 208 to pass laterally beneath the contact brushes 224 and reliably make electrical contact with the sampling module 209 loaded in the drive coupler 213 and ready for use. A spring loaded conductive ball bearing is one example of a contact brush 224 that could be used. A resilient conductive strip shaped to press against the inside surface of the flexible polymer sheet 227 along the analyte detecting member region 228 of the sampling module 209 is another embodiment of a contact brush 224.

The sampling module cartridge 205 has a supply canister 229 and a receptacle canister 230. The unused sampling modules of the sampling module belt 208 are disposed within the supply canister 229 and the sampling modules of the sampling module belt 208 that have been used are advanced serially after use into the receptacle canister 230.

Figure 20:
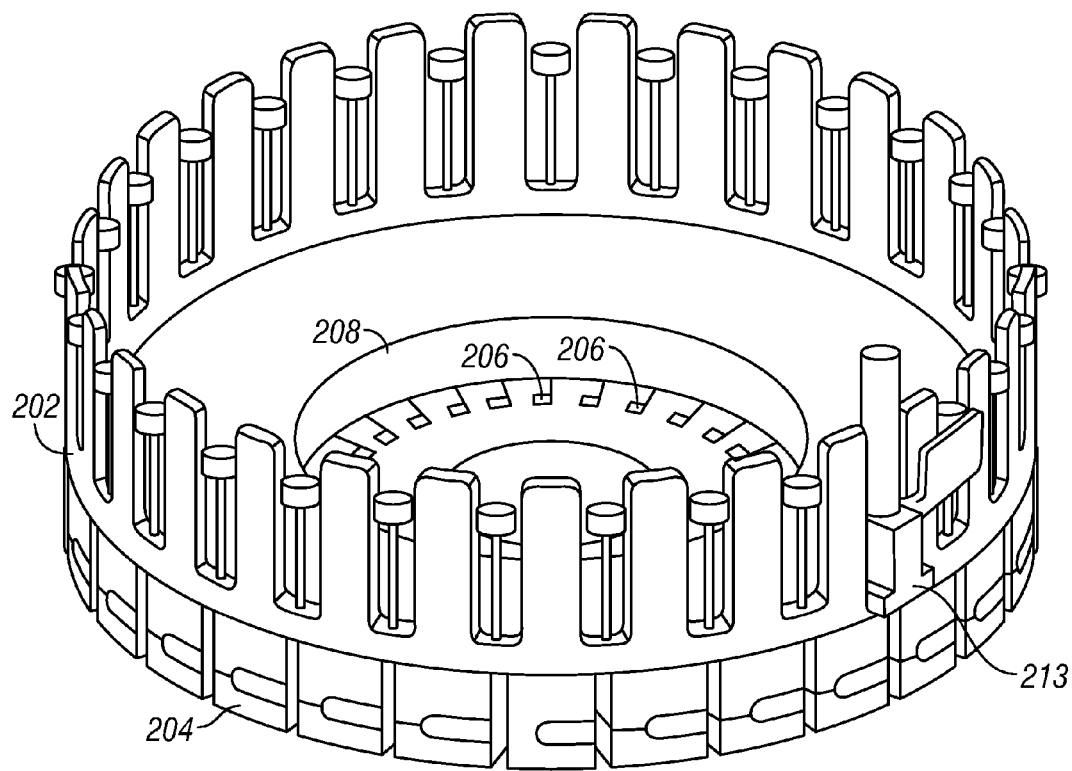
FIG. 20 is a perspective view of a sampling module cartridge with the sampling modules arranged in a ring configuration.

FIG. 20 illustrates a further embodiment of sampling module cartridges. FIG. 20 shows a sampling module cartridge 202 in a carousel configuration with adjacent sampling modules 204 connected rigidly and with analyte detecting members 206 from the analytical regions of the various sampling modules 204 disposed near an inner radius 208 of the carousel. The sampling modules 204 of the sampling module cartridge 202 are advanced through a drive coupler 213 but in a circular as opposed to a linear fashion.

Figure 21:
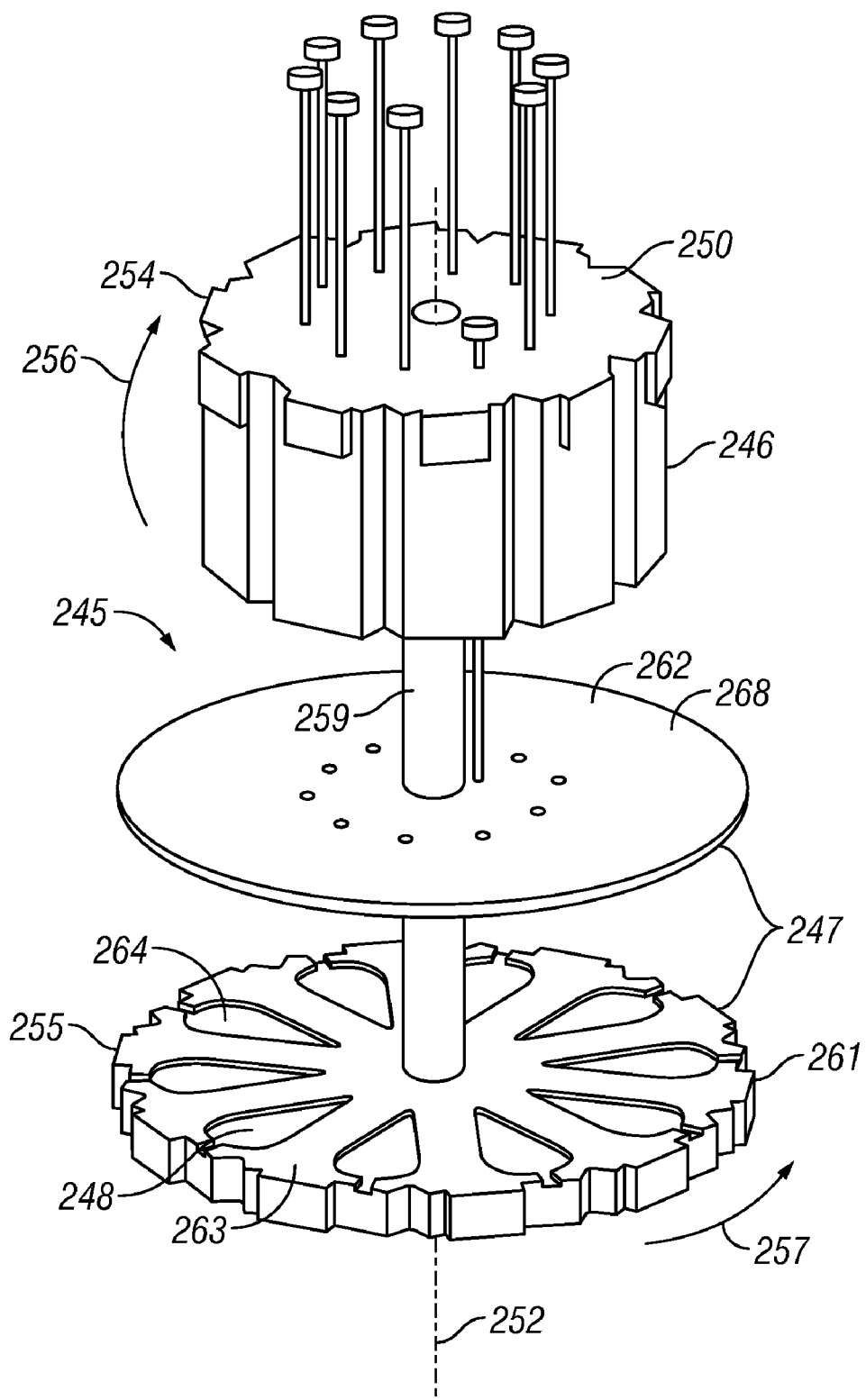
FIG. 21 illustrate an embodiment of a cartridge for use in sampling having a sampling cartridge body and a penetrating member cartridge body.

FIG. 21 shows an exploded view in perspective of the cartridge 245, which has a proximal end portion 254 and a distal end portion 255. The penetrating member cartridge body 246 is disposed at the proximal end portion 254 of the cartridge 245 and has a plurality of penetrating member module portions 250, such as the penetrating member module portion 250. Each penetrating member module portion 250 has a penetrating member channel 251 with a penetrating member 83 slidably disposed within the penetrating member channel 251. The penetrating member channels 251 are substantially parallel to the longitudinal axis 252 of the penetrating member cartridge body 246. The penetrating members 83 shown have a drive head 98, shaft portion 201 and sharpened tip 96. The drive head 98 of the penetrating members are configured to couple to a drive coupler (not shown), such as the drive coupler 85 discussed above.

The penetrating members 83 are free to slide in the respective penetrating member channels 251 and are nominally disposed with the sharpened tip 96 withdrawn into the penetrating member channel 251 to protect the tip 96 and allow relative rotational motion between the penetrating member cartridge body 246 and the sampling cartridge body 247 as shown by arrow 256 and arrow 257 in FIG. 21. The radial center of each penetrating member channel 251 is disposed a fixed, known radial distance from the longitudinal axis 252 of the penetrating member cartridge body 246 and a longitudinal axis 258 of the cartridge 245. By disposing each penetrating member channel 251 a fixed known radial distance from the longitudinal axes 252 and 258 of the penetrating member cartridge body 246 and cartridge 245, the penetrating member channels 251 can then be readily and repeatably aligned in a functional arrangement with penetrating member channels 253 of the sampling cartridge body 247. The penetrating member cartridge body 246 rotates about a removable pivot shaft 259 which has a longitudinal axis 260 that is coaxial with the longitudinal axes 252 and 250 of the penetrating member cartridge body 246 and cartridge 245.

The sampling cartridge body 247 is disposed at the distal end portion 255 of the cartridge and has a plurality of sampling module portions 248 disposed radially about the longitudinal axis 249 of the sampling cartridge body 247. The longitudinal axis 249 of the sampling cartridge body 247 is coaxial with the longitudinal axes 252, 258 and 260 of the penetrating member cartridge body 246, cartridge 245 and pivot shaft 259. The sampling cartridge body 247 may also rotate about the pivot shaft 259. In order to achieve precise relative motion between the penetrating member cartridge body 246 and the sampling cartridge body 247, one or both of the cartridge bodies 246 and 247 may be rotatable about the pivot shaft 259, however, it is not necessary for both to be rotatable about the pivot shaft 259, that is, one of the cartridge bodies 246 and 247 may be secured, permanently or removably, to the pivot shaft 259.

The sampling cartridge body 247 includes a base 261 and a cover sheet 262 that covers a proximal surface 263 of the base forming a fluid tight seal. Each sampling module portion 248 of the sampling cartridge body 247, such as the sampling module portion 248, has a sample reservoir 264 and a penetrating member channel 253. The sample reservoir 264 has a vent 965 at an outward radial end that allows the sample reservoir 264 to readily fill with a fluid sample. The sample reservoir 264 is in fluid communication with the respective penetrating member channel 253 which extends substantially parallel to the longitudinal axis 249 of the sampling cartridge body 247. The penetrating member channel 253 is disposed at the inward radial end of the sample reservoir 264. Still further description of the device of FIG. 21 may be found in commonly assigned, copending U.S. patent application Ser. No. 10/127,395 filed Apr. 19, 2002.

Figure 22A:
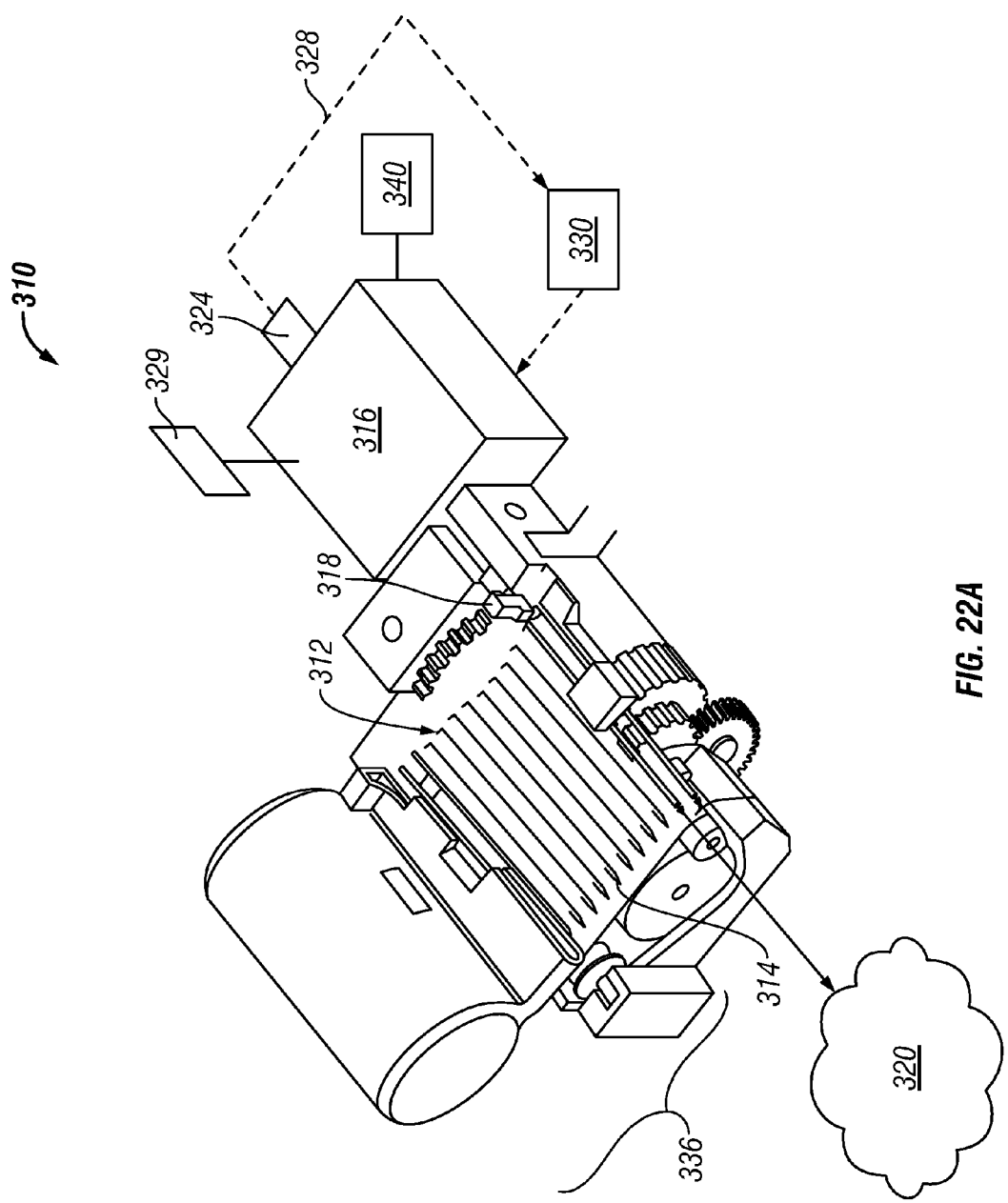
FIG. 22A shows a device for use on a tissue site having a plurality of penetrating members.

Referring to FIG. 22A, one embodiment of the present invention is a tissue penetrating system 310 with a plurality of penetrating members 312 that each have a tissue penetrating tip 314. The number of penetrating members 310 can vary, but numbers in the ranges of 10, 15, 25, 50, 75, 100, 500 or any other number, are suitable. Each penetrating member 312 can be a lancet, a traditional lancet with a molded body, a needle with a lumen, a knife like element, an elongate member without molded attachments, and the like, and may have a size in the range of 20 mm to 10 mm in length and between 0.012-0.040 mm in diameter. It should be understood of course that penetrating members of a variety of different sizes useful for lancing such as those of conventional lancets may be used in other embodiments. As seen in FIG. 22A, the penetrating member may have an elongate portion with a bend near a proximal end of the member.

Each penetrating member 312 is coupled to a penetrating member driver 316. Suitable penetrating member drivers 316 include but are not limited to, an electric drive force member, a voice coil drive force generator, a linear voice coil device, a rotary voice coil device, and the like. Suitable drive force generators can be found in commonly assigned, copending U.S. patent application Ser. No. 10/127,395 filed Apr. 19, 2002. In one embodiment, the penetrating member driver or drive force generator 316 may be a single actuator used to advance the penetrating member and to withdraw the member. The driver 316 may also be used to stop the penetrating member in the tissue site. Penetrating member driver 316 can be a non-spring actuator for drawing penetrating member 312 in a direction back towards penetrating member driver 316. A coupler 318 on penetrating member driver 316 is configured to engage at least a portion of an elongate portion of a penetrating member 312 in order to drive the penetrating member 312 along a path into and through target tissue 320, and then withdrawn from target tissue 320.

Figure 22B:
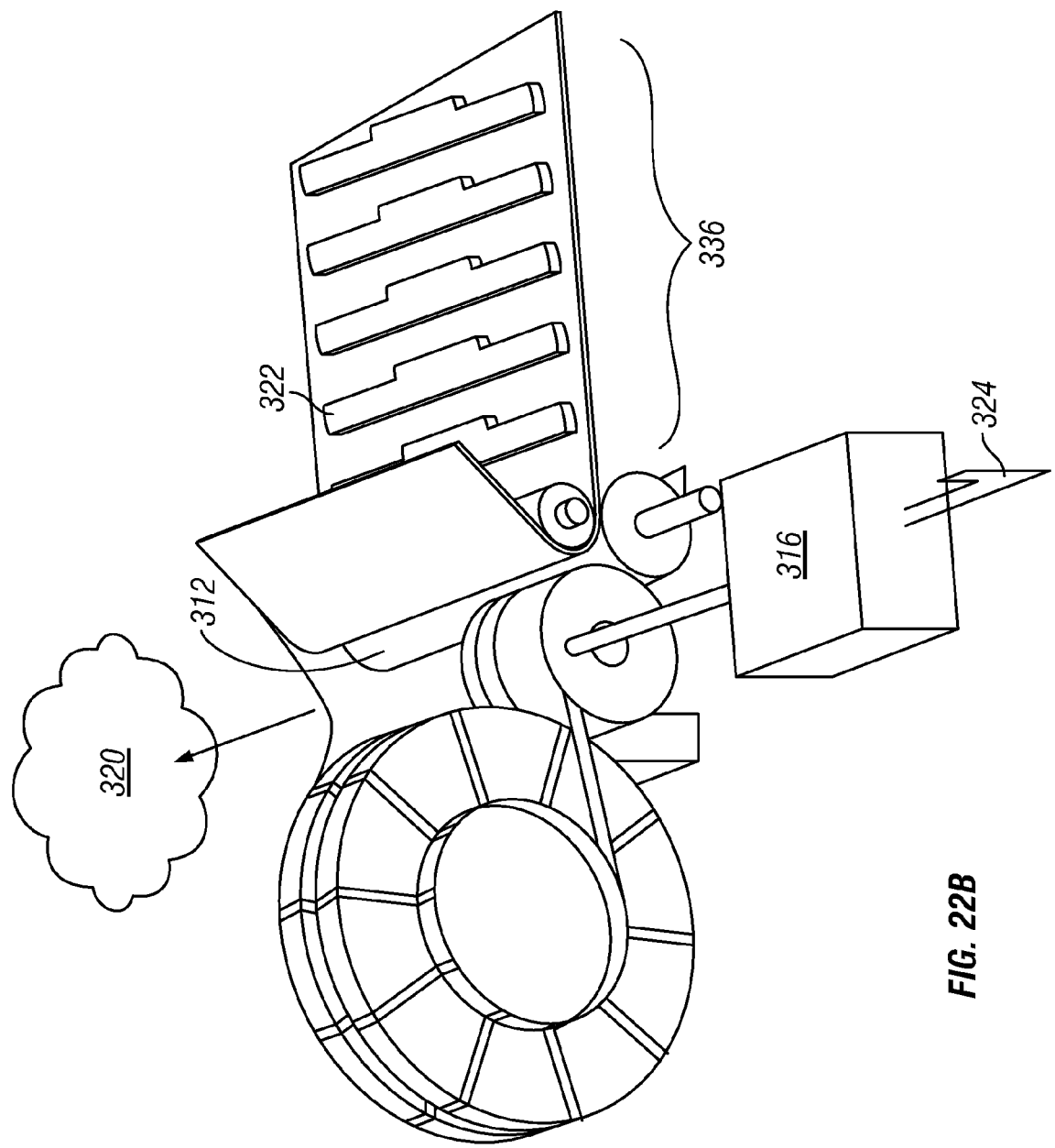
FIG. 22B shows rear view of a device for use on a tissue site having a plurality of penetrating members.

Referring now to FIG. 22B, the tips of the penetrating members 312 can be uncovered when they are launched into a selected target tissue 320. In one embodiment, sterility enclosures 322 are provided for covering at least the tip of each penetrating member 312. FIG. 22B shows that the enclosure may also cover the entire lancet. In one embodiment, each sterility enclosure 322 is removed from the penetrating member 312 prior to actuation, launch, of penetrating member 312 and positioned so that penetrating member 312 does not contact the associated sterility enclosure 322 during actuation. As seen in FIG. 22B, the enclosure 322 may be peel away to reveal the penetrating member 312 prior to coupling of the member 312 to the drive force generator 316. In another embodiment, each penetrating member 312 breaches its associated sterility enclosure 322 during launch.

Tissue penetrating system 310 can also include one or more penetrating member sensors 324 that are coupled to penetrating members 312. Examples of suitable penetrating member sensors 324 include but are not limited to, a capacitive incremental encoder, an incremental encoder, an optical encoder, an interference encoder, and the like. Each penetrating member sensor 324 is configured to provide information relative to a depth of penetration of a penetrating member 312 through a target tissue 320 surface, including but not limited to a skin surface, and the like. The penetrating member sensor 324 may be positioned as shown in FIG. 22B. The penetrating member sensor 324 may also be positioned in a variety of location such as but not limited to being closer to the distal end of the penetrating member, in a position as shown in FIG. 5, or in any other location useful for providing an indication of the position of a penetrating member 312 being driven by the force generator 316.

Figure 22C:
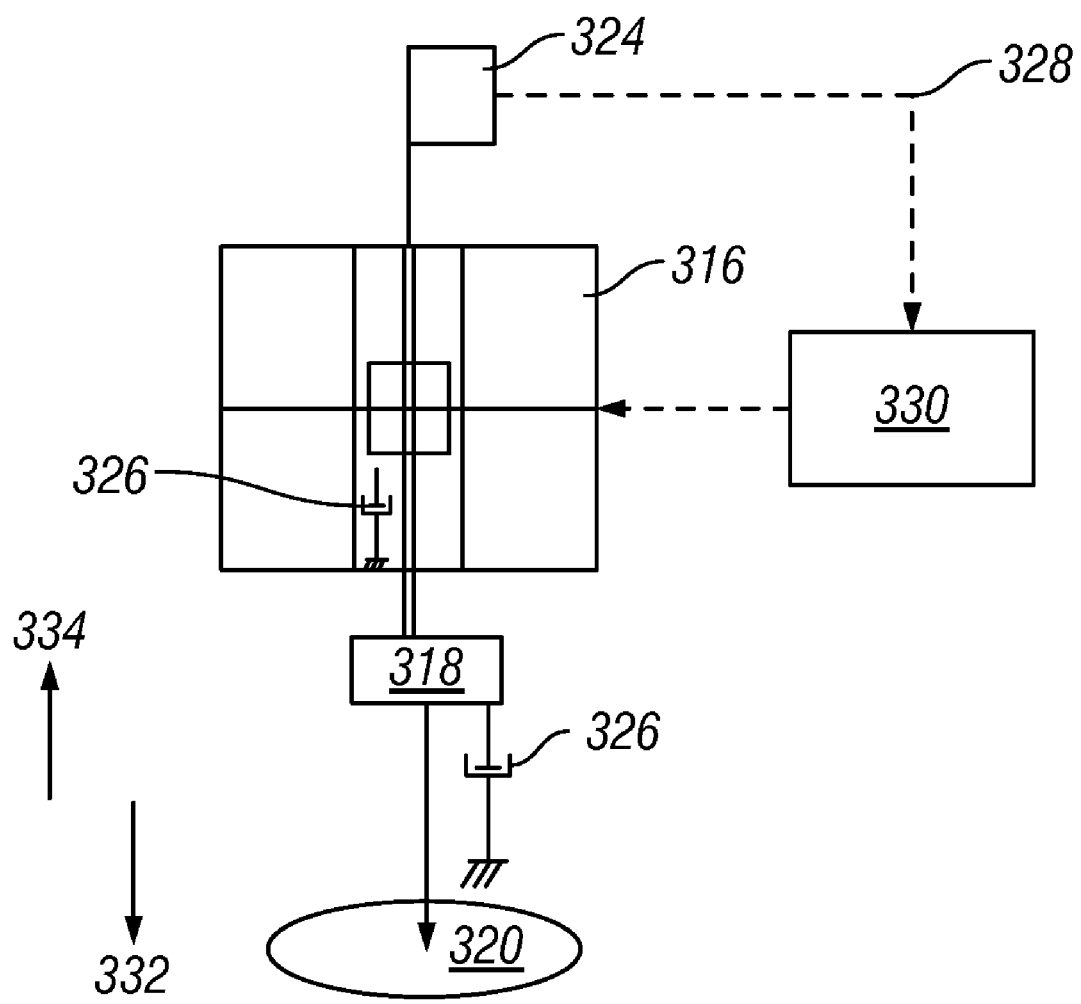
FIG. 22C shows a schematic of a device for use on a tissue site with a feedback loop and optionally a damper.

In various embodiments, the penetration depth of a penetrating member 312 through the surface of a target tissue 320 can be, 100 to 2500 microns, 500 to 750 microns, and the like. Each penetrating member sensor 324 can also provide an indication of velocity of a penetrating member 312. Referring to FIG. 22C, a damper 326 can be coupled to penetrating member driver 316. Damper 326 prevents multiple oscillations of penetrating member 312 in target tissue 320, particularly after penetrating member 312 has reached a desired depth of penetration. The damper 326 may be placed in a variety of positions such as but not limited to being coupled to the penetrating member, being coupled to the coupler 318, being coupled to a core or shaft in the drive force generator 316, or at any other position useful for slowing the motion of the penetrating member 312.

A feedback loop 328 can also be included that is coupled to penetrating member sensor 324. Each penetrating member 312 sensor can be coupled to a processor 330 that has control instructions for penetrating member driver 316. By way of illustration, and without limitation, processor 330 can include a memory for storage and retrieval of a set of penetrating member 312 profiles utilized with penetrating member driver 316. Processor 330 can also be utilized to monitor position and speed of a penetrating member 312 as it moves in first direction 332 to and through the target tissue 320.

Processor 330 can adjust an application of force to a penetrating member 312 in order to achieve a desired speed of a penetrating member 312. Additionally, processor 330 can also be used to adjust an application of force applied to a penetrating member 312 when penetrating member 312 contacts target tissue 320 so that penetrating member 312 penetrates target tissue 320 within a desired range of speed. Further, processor 330 can also monitor position and speed of a penetrating member 312 as penetrating member 312 moves in first direction 332 toward the target tissue 320. Application of a launching force to penetrating member 312 can be controlled based on position and speed of penetrating member 312. Processor 330 can control a withdraw force, from target tissue 320, to penetrating member 312 so that penetrating member 312 moves in second direction 334 away from target tissue 320.

Processor 330 can produce a signal that is indicative of a change in direction and magnitude of force exerted on penetrating member 312. Additionally, processor 330 can cause a braking force to be applied to penetrating member 312.

In one embodiment, in first direction 332 penetrating member 312 moves toward target tissue 320 at a speed that is different than a speed at which penetrating member 312 moves away from target tissue 320 in second direction 334. In one embodiment, the speed of penetrating member 312 in first direction 332 is greater than the speed of penetrating member 312 in second direction 334. The speed of penetrating member 312 in first direction 332 can be a variety of different ranges including but not limited to, 0.05 to 60 m/sec, 0.1 to 20.0 m/sec, 1.0 to 10.0 m/sec, 3.0 to 8.0 m/sec, and the like. Additionally, the dwell time of penetrating member 312 in target tissue 320, below a surface of the skin or other structure, can be in the range of, 1 microsecond to 2 seconds, 500 milliseconds to 1.5 second, 100 milliseconds to 1 second, and the like.

As seen in FIGS. 22A and 22B, tissue penetrating system 310 can include a penetrating member transport device 336 for moving each of penetrating member 312 into a position for alignment with penetrating member driver 316. Penetrating members 312 can be arranged in an array configuration by a number of different devices and structures defining support 338, including but not limited to, a belt, a flexible or non-flexible tape device, support channel, cog, a plurality of connectors, and the like. Support 338 can have a plurality of openings each receiving a penetrating member 312. Suitable supports 338 may also include but are not limited to, a bandolier, drum, disc and the like. A description of supports 338 can be found in U.S. Ser. No. 10/127,395, filed Apr. 19, 2002; U.S. Ser. No. 60/437,359, filed Dec. 31, 2002; and U.S. Ser. No. 60/437,205, filed Dec. 31, 2002. All applications listed above are fully incorporated herein by reference for all purposes.

As illustrated in FIG. 22(a), tissue penetrating system 310 can include a single penetrating member driver 316 and a plurality of penetrating members 312. Penetrating member driver 316 moves each penetrating member 312 along a path out of a housing that has a penetrating member exit and then into target tissue 320, stopping in target tissue 320, and then withdrawing out of the target tissue 320. Support 338 couples the penetrating members 312 to define a linear array. Support 338 is movable and configured to move each penetrating member 312 to a launch position associated with penetrating member driver 316. Penetrating member driver 316 can be controlled to follow a predetermined velocity trajectory into and out of target tissue 320.

Tissue penetrating system 310 can include a user interface 340 configured to relay different information, including but not limited to, skin penetrating performance, a skin penetrating setting, and the like. User interface 340 can provide a user with at a variety of different outputs, including but not limited to, penetration depth of a penetrating member 312, velocity of a penetrating member 312, a desired velocity profile, a velocity of penetrating member 312 into target tissue 320, velocity of the penetrating member 312 out of target tissue 320, dwell time of penetrating member 312 in target tissue 320, a target tissue relaxation parameter, and the like. User interface 340 can include a variety of components including but not limited to, a real time clock 342, one or more alarms 344 to provide a user with a reminder of a next target penetrating event is needed, a user interface processor 346, and the like.

User interface 340 can provide a variety of different outputs to a user including but not limited to, number of penetrating members 312 available, number of penetrating members 312 used, actual depth of penetrating member 312 penetration on target tissue 320, stratum corneum thickness in the case where the target tissue 320 is the skin and an area below the skin, force delivered on target tissue 320, energy used by penetrating member driver 316 to drive penetrating member 312 into target tissue 320, dwell time of penetrating member 312, battery status of tissue penetrating system 310, status of tissue penetrating system 310, the amount of energy consumed by tissue penetrating system 310, or any component of tissue penetrating system 310, speed profile of penetrating member 312, information relative to contact of penetrating member 312 with target tissue 320 before penetration by penetrating member 312, information relative to a change of speed of penetrating member 312 as in travels in target tissue 320, and the like.

User interface 340 can include a data interface 348 that couples tissue penetrating system 310 to support equipment 350 with an interface, the internet, and the like. The data interface 348 may also be coupled to the processor 93. Suitable support equipment 350 includes but is not limited to, a base station, home computer, central server, main processing equipment for storing analyte, such as glucose, level information, and the like.

Data interface 348 can be a variety of interfaces including but not limited to, Serial RS-232, modem interface, USB, HPNA, Ethernet, optical interface, IRDA, RF interface, Bluetooth interface, cellular telephone interface, two-way pager interface, parallel port interface standard, near field magnetic coupling, RF transceiver, telephone system, and the like.

User interface 340 be coupled to a memory 352 that stores, a target tissue parameter, target tissue 320 penetrating performance, and the like. The memory 352 may also be connected to processor 93 and store data from the user interface 340.

In one embodiment, memory 352 can store, the number of target tissue penetrating events, time and date of the last selected number of target tissue penetrating events, time interval between alarm and target tissue penetrating event, stratum corneum thickness, time of day, energy consumed by penetrating member driver 316 to drive penetrating member 312 into target tissue 320, depth of penetrating member 312 penetration, velocity of penetrating member 312, a desired velocity profile, velocity of penetrating member 312 into target tissue 320, velocity of penetrating member 312 out of target tissue 320, dwell time of penetrating member 312 in target tissue 320, a target tissue relaxation parameter, force delivered on target tissue 320 by any component of tissue penetrating device, dwell time of penetrating member 312, battery status of tissue penetrating system 310, tissue penetrating system 310 status, consumed energy by tissue penetrating system 310 or any of its components, speed profile of penetrating member 312 as it penetrates and advances through target tissue 320, a tissue target tissue relaxation parameter, information relative to contact of penetrating member 312 with target tissue 320 before penetration by penetrating member 312, information relative to a change of speed of penetrating member 312 as in travels in and through target tissue 320, information relative to consumed analyte detecting members, and information relative to consumed penetrating members 312.

In one embodiment, processor 330 is coupled to and receives any of a different type of signals from user interface 340. User interface 340 can respond to a variety of different commands, including but not limited to audio commands, and the like. User interface 340 can include a sensor for detecting audio commands. Information can be relayed to a user of tissue penetrating system 310 by way of an audio device, wireless device 329, and the like.

Figure 23B:
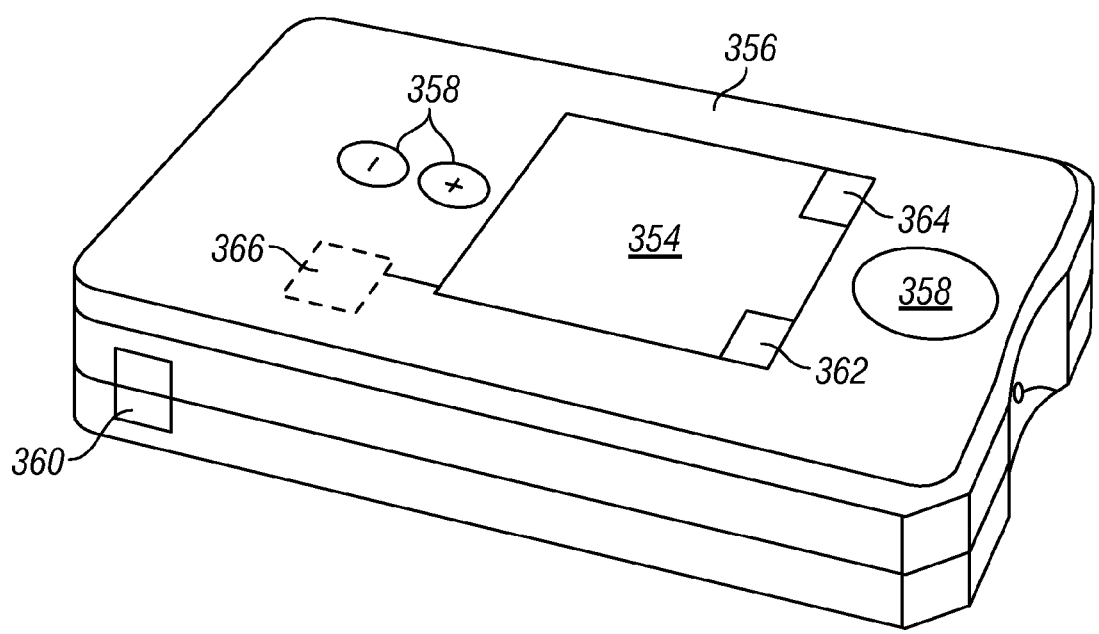
FIG. 23B shows an outer view of a device with a user interface.

In another embodiment as seen in FIG. 23B, tissue penetrating device includes a human interface 354 with at least one output. The human interface 354 is specific for use by humans while a user interface 340 may be for any type of user, with user defined generically. Human interface 354 can be coupled to processor 330 and penetrating member sensor 324. Human interface 354 can be a variety of different varieties including but not limited to, LED, LED digital display, LCD display, sound generator, buzzer, vibrating device, and the like.

The output of human interface 354 can be a variety of outputs including but not limited to, a penetration event by penetrating member 312, number of penetrating members 312 remaining, time of day, alarm, penetrating member 312 trajectory waveform profile information, force of last penetration event, last penetration event, battery status of tissue penetrating system 310, analyte status, time to change cassette status, jamming malfunction, tissue penetrating system 310 status, and the like.

Human interface 354 is coupled to a housing 356. Suitable housings 356 include but are not limited to a, telephone, watch, PDA, electronic device, medical device, point of care device, decentralized diagnostic device and the like. An input device 358 is coupled to housing. Suitable input devices 358 include but are not limited to, one or more pushbuttons, a touch pad independent of the display device, a touch sensitive screen on a visual display, and the like.

A data exchange device 360 can be utilized for coupling tissue penetrating system 310 to support equipment 350 including but not limited to, personal computer, modem, PDA, computer network, and the like. Human interface 354 can include a real time clock 362, and one or more alarms 364 that enable a user to set and use for reminders for the next target tissue penetration event. Human interface 354 can be coupled to a human interface processor 366 which is distinct from processor 330. Human interface processor 366 can include a sleep mode and can run intermittently to conserve power. Human interface processor 366 includes logic that can provide an alarm time set for a first subset of days, and a second alarm time set for a second subset of days. By way of example, and without limitation, the first subset of days can be Monday through Friday, and the second subset of days can be Saturday and Sunday.

Human interface 354 can be coupled to a memory 368 for storing a variety of information, including but not limited to, the number of target tissue penetrating events, time and date of the last selected number of target tissue penetrating events, time interval between alarm and target tissue penetrating event, stratum corneum thickness when target tissue 320 is below the skin surface and underlying tissue, time of day, energy consumed by penetrating member driver 316 to drive penetrating member 312 into target tissue 320, depth of penetrating member 312 penetration, velocity of penetrating member 312, a desired velocity profile, velocity of penetrating member 312 into target tissue 320, velocity of penetrating member 312 out of target tissue 320, dwell time of penetrating member 312 in target tissue 320, a target tissue relaxation parameter, force delivered on target tissue 320, dwell time of penetrating member 312, battery status of tissue penetrating system 310 and its components, tissue penetrating system 310 status, consumed energy, speed profile of penetrating member 312 as it advances through target tissue 320, a target tissue relaxation parameter, information relative to contact of a penetrating member 312 with target tissue 320 before penetration by penetrating member 312, information relative to a change of speed of penetrating member 312 as in travels in target tissue 320, information relative to consumed sensors, information relative to consumed penetrating members 312.

As illustrated in FIG. 24, tissue penetrating system 310 can include a penetrating member driver 316 and a plurality of cartridges 370. Each cartridge 370 contains a penetrating member 312. The cartridges 370 can be coupled together in an array, which can be a flexible array. A cartridge transport device 372 moves cartridges 370 into a launch position that operatively couples a penetrating member 312 to penetrating member driver 316. A support couples cartridges 370 to define an array. A plurality of sterility enclosures 322 can be provided to at least cover tips of penetrating members 312. Sterility enclosure 322 (shown in phantom) is removed from their associated penetrating members 312 prior to launch of the penetrating member 312. The enclosure may be peeled away (not shown) in a manner similar to that as seen in FIG. 22B, with the enclosure 322 on one tape surface being peeled away. The enclosure 322 may be a blister sack, a sack tightly formed about each cartridge 370, or other enclosure useful for maintaining a sterile environment about the cartridge 370 prior to actuation or launch. The enclosure 322 may contain the entire cartridge 370 or some portion of the cartridge 370 which may need to remain sterile prior to launch. During launch, enclosure or sterility barrier 322 can be breached by a device other than penetrating member 312, or can be breached by penetrating member 312 itself. An analyte detection member, sensor, may be positioned to receive fluid from a wound created by the penetrating member 312. The member may be on the cartridge 370 or may be on the device 80.

Figure 25:
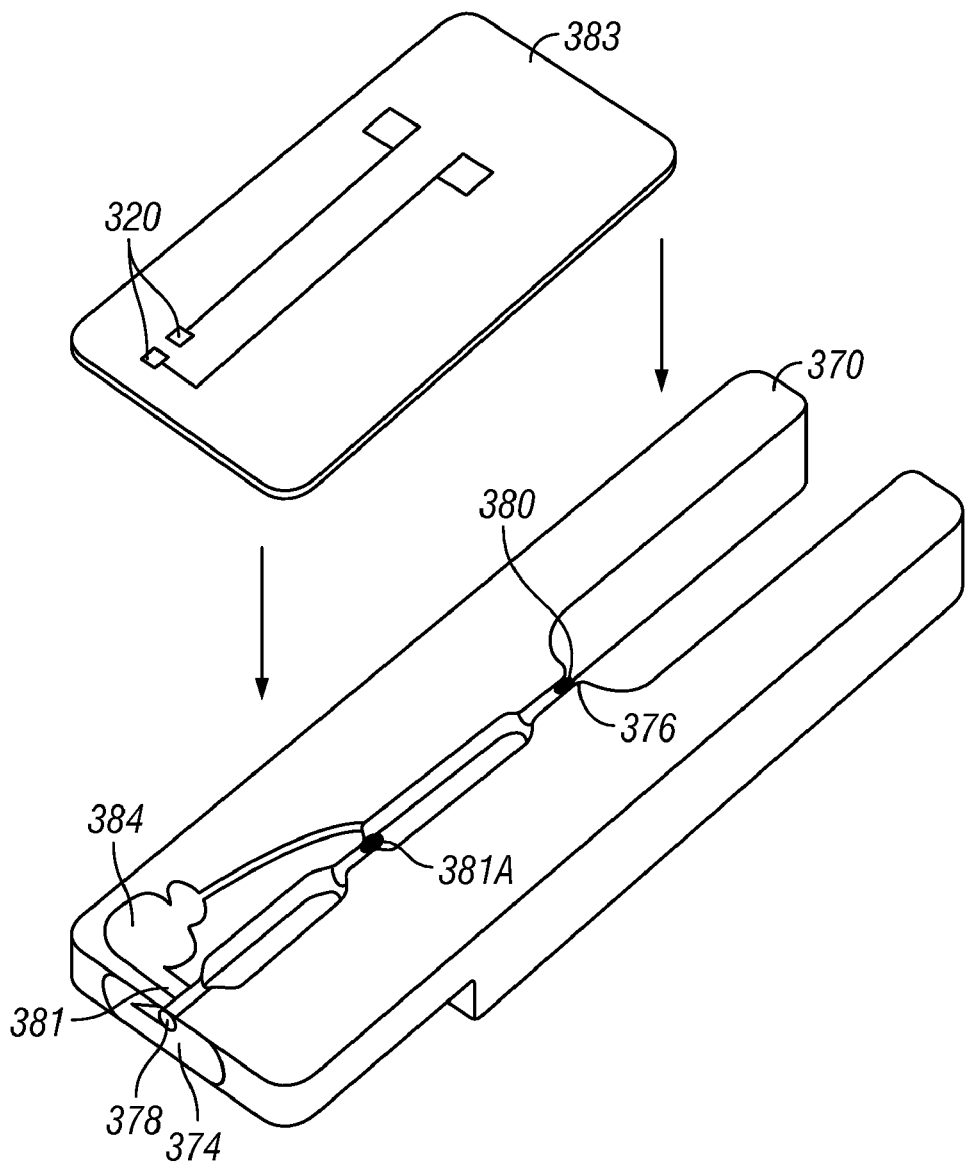
FIG. 25 is an exploded view of a cartridge for use with a system for sampling body fluid.

Referring to FIGS. 24 and 25, one embodiment of tissue penetrating system 310 includes cartridge transport device 372 and a plurality of cartridges 370. Each cartridge 370 is associated with a penetrating member 312. Cartridge transport device 372 moves each cartridge 370 to a position to align the associated penetrating member 312 with penetrating member driver 316 to drive penetrating member 312 along a path into target tissue 320. In one embodiment as seen in FIG. 25, each cartridge 370 has at least one of a distal port 374 and a proximal port 376. A first seal 378 is positioned at distal or proximal ports. As seen in FIG. 25, the seal 378 may be placed at the distal port. First seal 378 is formed of a material that is fractured by penetrating member 312 before it is launched. A second seal 380 can be positioned at the other port. It will be appreciated that only one or both of distal and proximal ports 374 and 376 can be sealed, and that each cartridge 370 can include only one port 374 and 376. For ease of illustration, the penetrating member 312 extending longitudinally through the lumen in the cartridge 370 is not shown. The seals 380 and 378 may be fracturable seals formed between the penetrating member and the cartridge 370. During actuation, the seals 378 and 380 are broken. Seal 378 may be also be positioned to cover the distal port or exit port 374 without being sealed against the penetrating member (i.e. covering the port without touching the penetrating member). A third seal 381 may be positioned to cover an entrance to sample chamber 384. The seal 381 may be configured to be broken when the penetrating member 312 is actuated. A still further seal 381A may be placed in the lumen. The tip of a penetrating member may be located at any position along the lumen, and may also be at or surrounded by one of the seals 378, 381, 381A, or 376.

Referring still to FIG. 25, a cover sheet 383 may be a flexible polymer sheet as described in commonly assigned, copending U.S. patent application Ser. No. 10/127,395 filed Apr. 19, 2002. It should be understood of course that the sheet may be made of a variety of materials useful for coupling an analyte detecting member 390. This allows the analyte detecting member 390 to be sterilized separately from the cartridge 370 and assembled together with the cartridge at a later time. This process may be used on certain analyte detecting members 390 that may be damaged if exposed to the sterilization process used on the cartridge 370. Of course, some embodiments may also have the analyte detecting member 390 coupled to the cartridge 370 during sterilization. The cover sheet 383 may also form part of the seal to maintain a sterile environment about portions of the penetrating member. In other embodiments, the lumen housing penetrating member may be enclosed and not use a sheet 383 to help form a sterile environment. In still further embodiments, the sheet 383 may be sized to focus on covering sample chamber 384.

Figure 27:
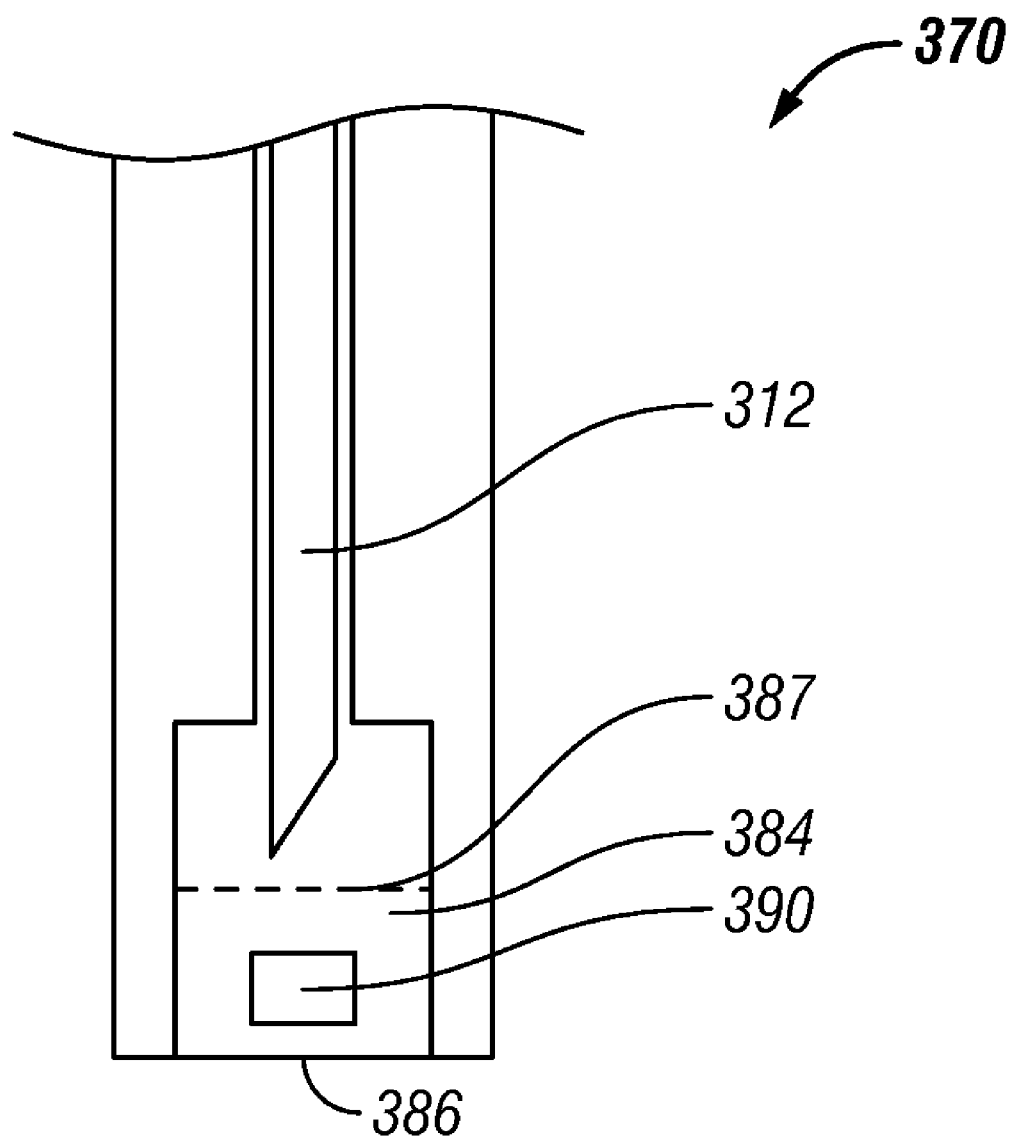
FIGS. 27-28 show cartridges for use with a system for sampling body fluid.

As illustrated in FIG. 26, cartridge 370 has at least one port 374. A plurality of penetrating members 312 are in cartridge 370. Although cartridge 370 is shown in FIG. 26 to have a linear design, the cartridge 370 may also have a curved, round, circular, triangular, or other configuration useful for positioning a penetrating member for use with a drive force generator. A seal 382 is associated with each penetrating member 312 in order to maintain each penetrating member 312 in a sterile environment in cartridge 370 prior to launch. Prior to launch, seal 382 associated with the penetrating member 312 to be launched is broken. In one embodiment, a punch (not shown) is used to push down on the seal 382 covering the port 376 of the cartridge 370. This breaks the seal 382 and also pushes it downward, allowing the penetrating member to exit the cartridge without contacting the seal 382. The timing of the breaking of the seal 382 may be varied so long as the penetrating member remains substantially sterile when being launched towards the tissue site 320. In other embodiments, the port 376 may have a seal 383 that protrudes outward and is broken off by the downward motion of the punch. One or more sample chambers 384 are included in cartridge 370. In one embodiment, each penetrating member 312 has an associated sample chamber 384. In one embodiment, illustrated in FIG. 27, penetrating member 312 is extendable through an opening 386 of its associated sample chamber 384. In some embodiments, a seal 387 may be included in the sample chamber 384. Seals 382 and 387 may be made from a variety of materials such as but not limited to metallic foil, aluminum foil, paper, polymeric material, or laminates combining any of the above. The seals may also be made of a fracturable material. The seals may be made of a material that can easily be broken when a device applies a force thereto. The seals alone or in combination with other barriers may be used to create a sterile environment about at least the tip of the penetrating member prior to lancing or actuation.

Figure 28:
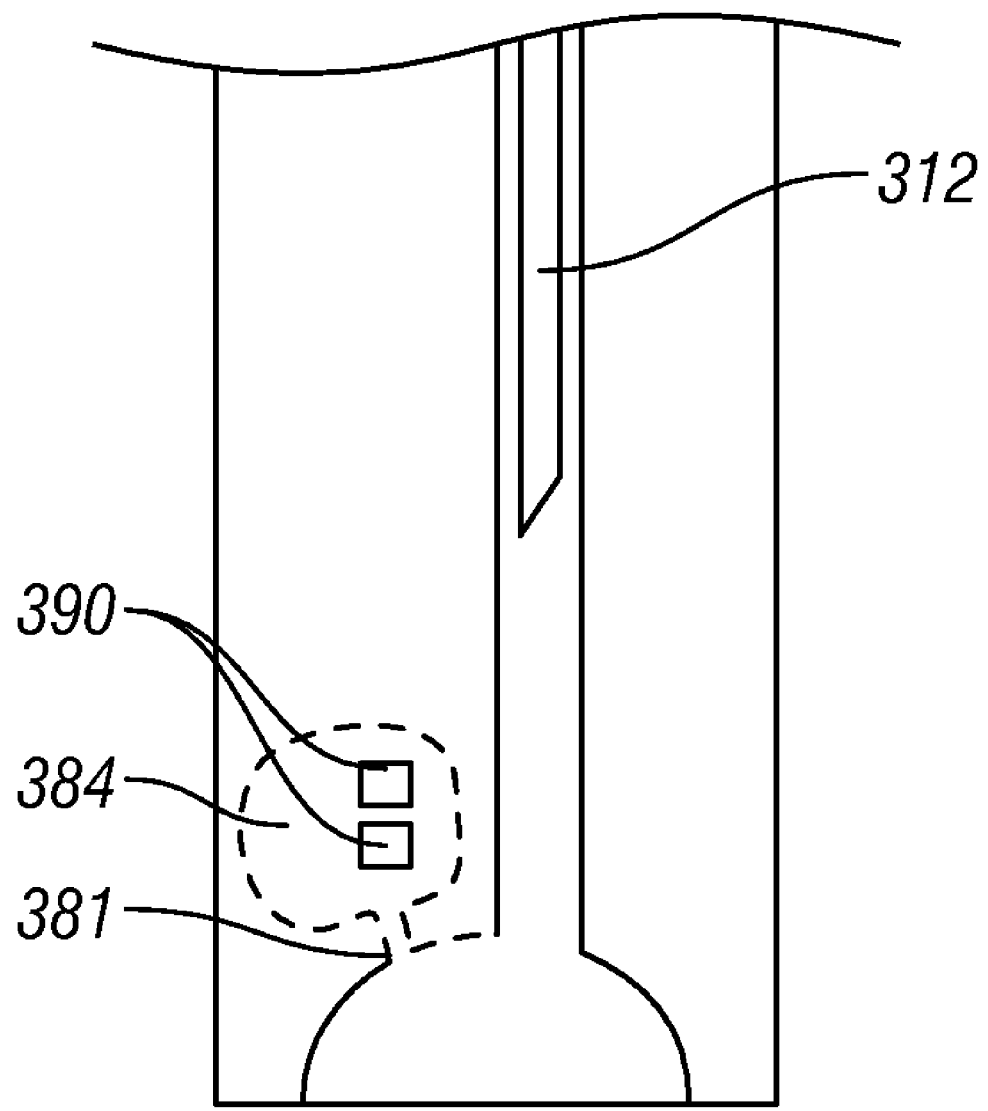

With reference now to the embodiment of FIG. 28, each sample chamber 384 may have an opening 388 for transport of a body fluid into the sample chamber 384. The size of sample chambers 384 in FIGS. 26 through 28 can vary. In various embodiments, sample chambers 384 are sized to receive, no more than 1.0 µL of the body fluid, no more than 0.75 µL of the body fluid, no more than 0.5 µL of the body fluid, no more than 0.25 µL of the body fluid, no more than 0.1 µL of the body fluid, and the like. It will be appreciated that sample chambers 384 can have larger or smaller sizes.

An analyte detecting member 390 may associated with each sample chamber 384. The analyte detecting member 390 may be designed for use with a variety of different sensing techniques as described in commonly assigned, copending U.S. patent application Ser. No. 10/127,395 filed Apr. 19, 2002. Analyte detecting member 390 can be positioned in sample chamber 384, at an exterior of sample chamber 384, or at other locations useful for obtaining an analyte. Analyte detecting member 390 can be in a well 392, or merely be placed on a support.

In one embodiment, analyte detecting member 390 includes chemistries that are utilized to measure and detect glucose, and other analytes. In another embodiment, analyte detecting member 390 is utilized to detect and measure the amount of different analytes in a body fluid or sample. In various embodiments, analyte detecting member 390 determines a concentration of an analyte in a body fluid using a sample that does not exceed a volume of, 1 µL of a body fluid disposed in sample chamber 384, 0.75 µL of a body fluid disposed in sample chamber 384, 0.5 µL of a body fluid disposed in sample chamber 384, 0.25 µL of a body fluid disposed in sample chamber 384, 0.1 µL of a body fluid disposed in sample chamber 384, and the like. For example and not by way of limitation, the sample chamber 384 may be of a size larger than the volumes above, but the analyte detecting member 390 can obtain an analyte reading using the amounts of fluid described above.

As illustrated in FIG. 29, tissue penetrating system 310 can include a housing member 394, a penetrating member 312 positioned in housing member 394, and analyte detecting member 390 coupled to a sample chamber 384. Analyte detecting member 390 is configured to determine a concentration of an analyte in a body fluid using with a variety of different body fluid, sample, volumes. In various embodiments, the volume is less than 1 µL of body fluid disposed in sample chamber 384, 0.75 of body fluid disposed in sample chamber 384, 0.5 of body fluid disposed in sample chamber 384, 0.25 of body fluid disposed in sample chamber 384, 0.1 of body fluid disposed in sample chamber 384 and the like. Each tip of a penetrating member 312 is configured to extend through an opening of sample chamber 384. A plurality of penetrating members 312 can be positioned in housing member 394. Housing member 394 can be the same as cartridge 370. Cartridge 370 can have distal and proximal ports 374 and 376, respectively. Additionally, in this embodiment, a plurality of cartridges 370 can be provided, each associated with a penetrating member 312.

Figure 30:
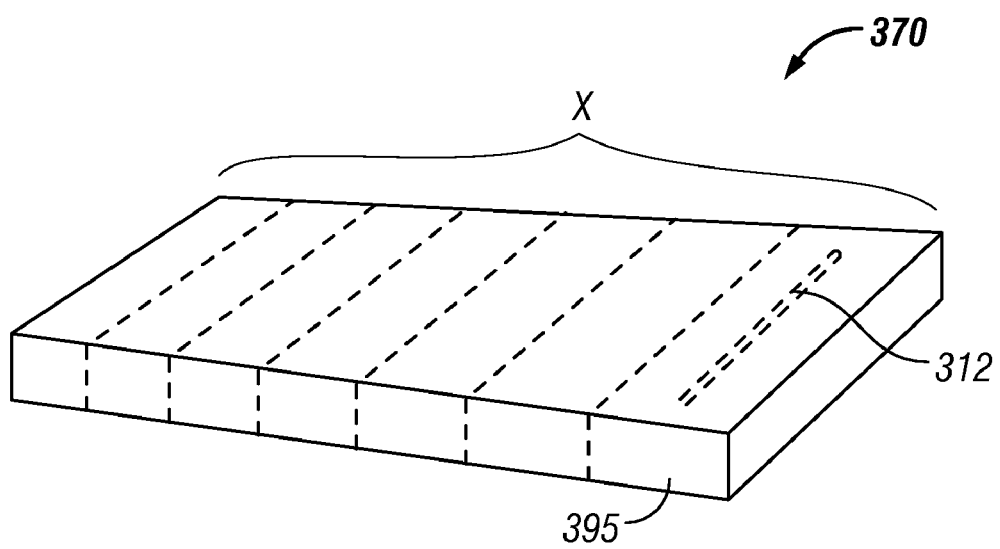
FIG. 30 shows the density associated with a cartridge according to the present invention.

Referring to FIG. 30, each penetrating member 312 has a packing density, or occupied volume, in cartridge 370. In various embodiments, the packing density of each penetrating member 312 in cartridge 370 can be no more than, 5.0 cm$^3$/penetrating member 312, 4.0 cm$^3$/penetrating member 312, 3.0 cm$^3$/penetrating member 312, 2.0 cm$^3$/penetrating member 312, 1.0 cm$^3$/penetrating member 312, 0.75 cm$^3$/penetrating member 312, 0.5 cm$^3$/penetrating member 312, 0.25 cm$^3$/penetrating member 312, 0.1 cm$^3$/penetrating member 312, and the like. In other words, the volume required for each penetrating member does not exceed 5.0 cm$^3$/penetrating member 312, 4.0 cm$^3$/penetrating member 312, 3.0 cm$^3$/penetrating member 312, 2.0 cm$^3$/penetrating member 312, 1.0 cm$^3$/penetrating member 312, 0.75 cm$^3$/penetrating member 312, 0.5 cm$^3$/penetrating member 312, 0.25 cm$^3$/penetrating member 312, 0.1 cm$^3$/penetrating member 312, and the like. So, as seen in FIG. 30, if the total package volume of the cartridge is defined as X and the cartridge includes Y number of penetrating members 312, penetrating members 312 and test area, or other unit 395, the volume for each unit does not exceed 5.0 cm$^3$/unit, 4.0 cm$^3$/unit, 3.0 cm$^3$/unit, 2.0 cm$^3$/unit, 1.0 cm$^3$/unit, 0.75 cm$^3$/unit, 0.5 cm$^3$/unit, 0.25 cm$^3$/unit, 0.1 cm$^3$/unit, and the like.

In various embodiments, each penetrating member 312 and its associated sample chamber 384 have a combined packing density of no more than about 5.0 cm$^3$, 4.0 cm$^3$, 3.0 cm$^3$, 2.0 cm$^3$, 1.0 cm$^3$, 0.75 cm$^3$, 0.5 cm$^3$, 0.25 cm$^3$, 0.1 cm$^3$, and the like.

Figure 31:
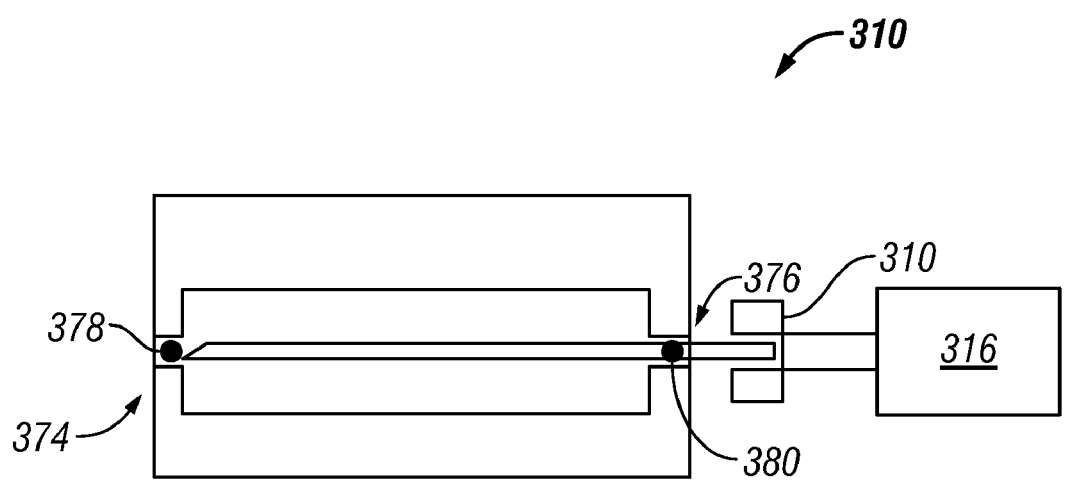
FIG. 31 shows a cutaway view of another embodiment of a system for sampling body fluid.

With reference now to FIG. 31, tissue penetrating system 310 can have a first seal 378 formed at distal port 374 and a second seal 380 formed at proximal port 376 of cartridge 370. Prior to launching of penetrating member 312, distal seal 378 and second seal 380 maintain a distal tip of penetrating member 312 and sample chamber 384 in a sterile environment. Second seal 380 is breached, and penetrating member 312 is then launched.

As illustrated in FIG. 32, a plurality of lumens 396 can be positioned between distal port 374 and proximal port 376 of cartridge 370 for slidably receiving a penetrating member 312. Sample chamber 384 is defined by cartridge 370, has an opening 398 and is associated with penetrating member 312. First seal 378 covers distal port 374, and a second seal 380 covers proximal port 376.

In another embodiment as shown in FIG. 33, tissue penetrating system 310 includes a plurality of cartridges 370, penetrating member driver 316, and a plurality of penetrating members 312 coupled to penetrating member driver 316. Each penetrating member 312 is associated with a cartridge 370. A plurality of gas-tightly sealed enclosures 400 are coupled in an array. Each enclosure 400 fully contains at least one of cartridge 370. Enclosures 400 are configured to be advanceable on cartridge transport device 372 that individually releases cartridges 370 from sacks or enclosures 400 and loads them individually onto penetrating member driver 316. The enclosures 400 may be removed by peeling back a top portion of the tape as shown in FIG. 22B.

In another embodiment, a plurality of penetrating members 312 each have a sharpened distal tip. A penetrating member driver 316 is coupled to each penetrating member 312. A plurality of cartridges 370 are coupled in an array. Each cartridge 370 houses a penetrating member 312 and is configured to permit penetrating member driver 316 to engage each of penetrating members 312 sequentially. Each cartridge 370 has a plurality of seals positioned to provide that the sharpened distal tips remain in a sterile environment before penetrating target tissue 320. Penetrating members 312 are launched without breaking a seal using the penetrating member.

Figure 34:
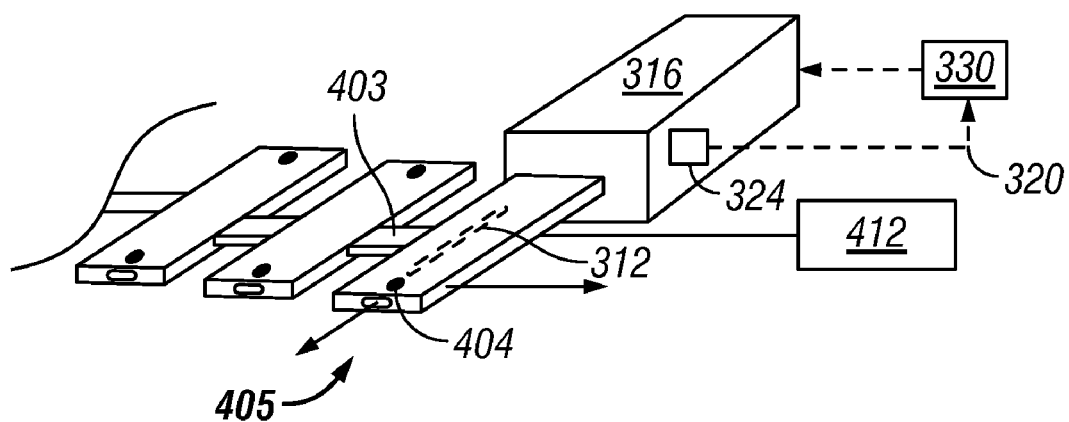

Referring now to FIG. 34, a plurality of cartridges 370 are provided, each having distal and proximal ports 374 and 376, respectively. A plurality of penetrating members 312 are each associated with a cartridge 370. Each penetrating member 312 has a sharpened distal tip and a shaft portion slidably disposed within cartridge 370. As seen in FIG. 34, the cartridges 370 may be coupled together by a connector or flexible support 403. A seal 404 is formed by a fracturable material between the penetrating member 312 and each cartridge 370. Seal 404 is positioned in at least one of distal or proximal ports 374 and 376, respectively, of cartridge 370. Cartridge transport device 372 moves each cartridge 370 to a position 405 that aligns penetrating member 312 with penetrating member driver 316 so that penetrating member 312 can be driven along a path into target tissue 320.

Figure 35:
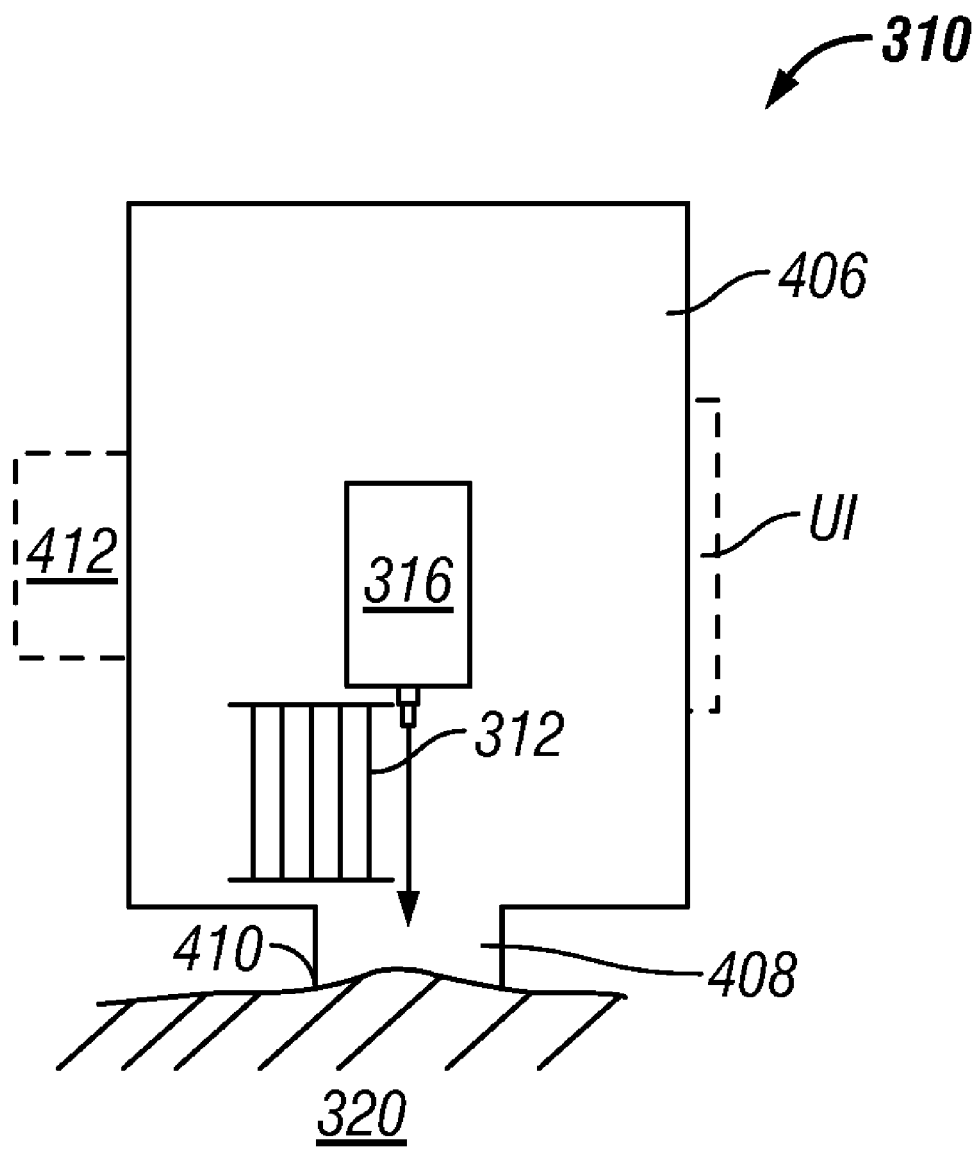
FIG. 35 shows an embodiment of the present invention with a tissue stabilizing member.

In another embodiment of the present invention as seen in FIG. 35, tissue penetrating system 310 includes a housing member 406, the plurality of penetrating members 312 positioned in housing member 406, and a tissue stabilizing member 408, which can also be a pressure applicator, stimulating member, stimulating vibratory member that imparts motion to a tissue surface, and the like. Tissue stabilizing member 408 can be positioned to at least partially surround an impact location of the penetrating member 312 on the target tissue 320 site. Tissue stabilizing member 408 can, enhance fluid flow from target tissue 320, stretch a target tissue 320 surface, apply a vacuum to target tissue 320, apply a force to target tissue 320 and cause target tissue 320 to press in an inward direction relative to housing member 406, apply a stimulation to target tissue 320, and the like. Tissue stabilizing member 408 can have a variety of different configurations. In one embodiment, tissue stabilizer member 408 includes a plurality of protrusions 410. In some further embodiments, a vacuum source 412 may be provided to assist the creation of a low pressure environment in the tissue stabilizing member 408 or along the fluid path to a sample chamber associated with the system 310. In some embodiments, the tissue stabilizing member 408 is mounted on the cartridge 370. In other embodiments, the member 408 may be mounted on the housing 406. The member 408 may also be pressed against the tissue site 320 and act as a pressure applicator. The member 408 may also be used against a variety of tissue including but not limited to skin or other body tissue.

Figure 36:
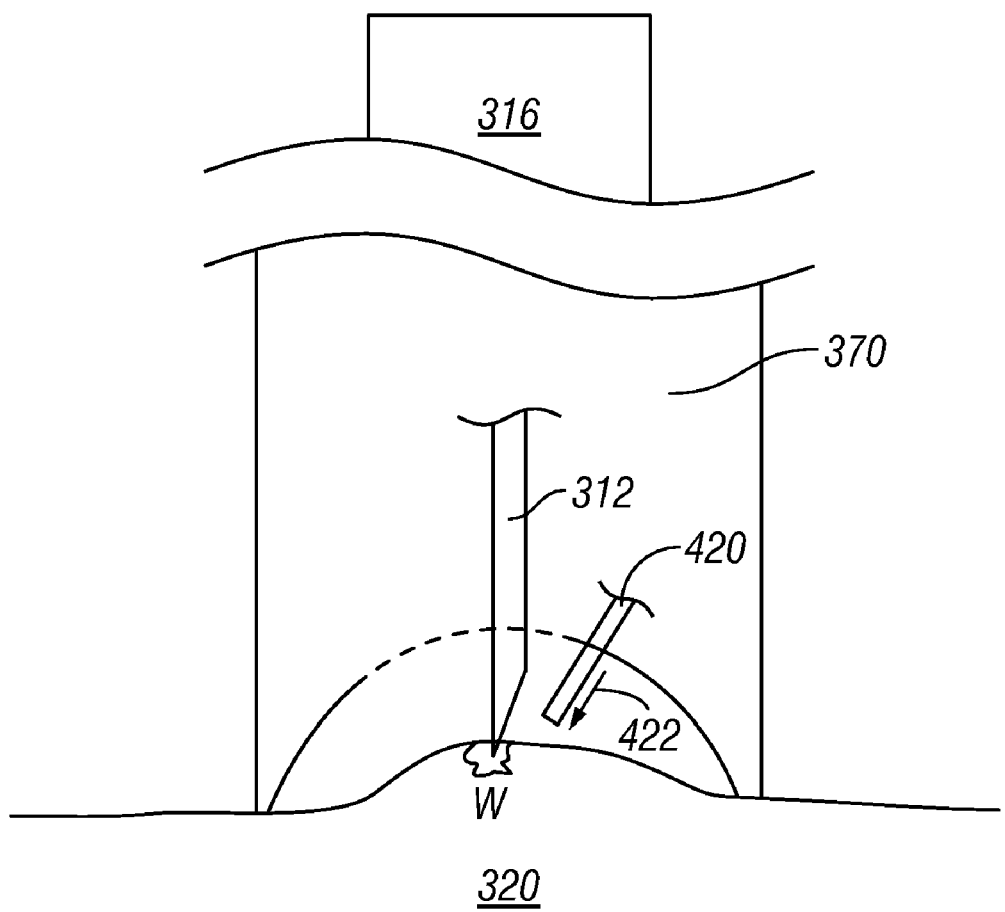
FIG. 36 shows a cartridge according to the present invention with a tissue stabilizing member.
Figure 37:
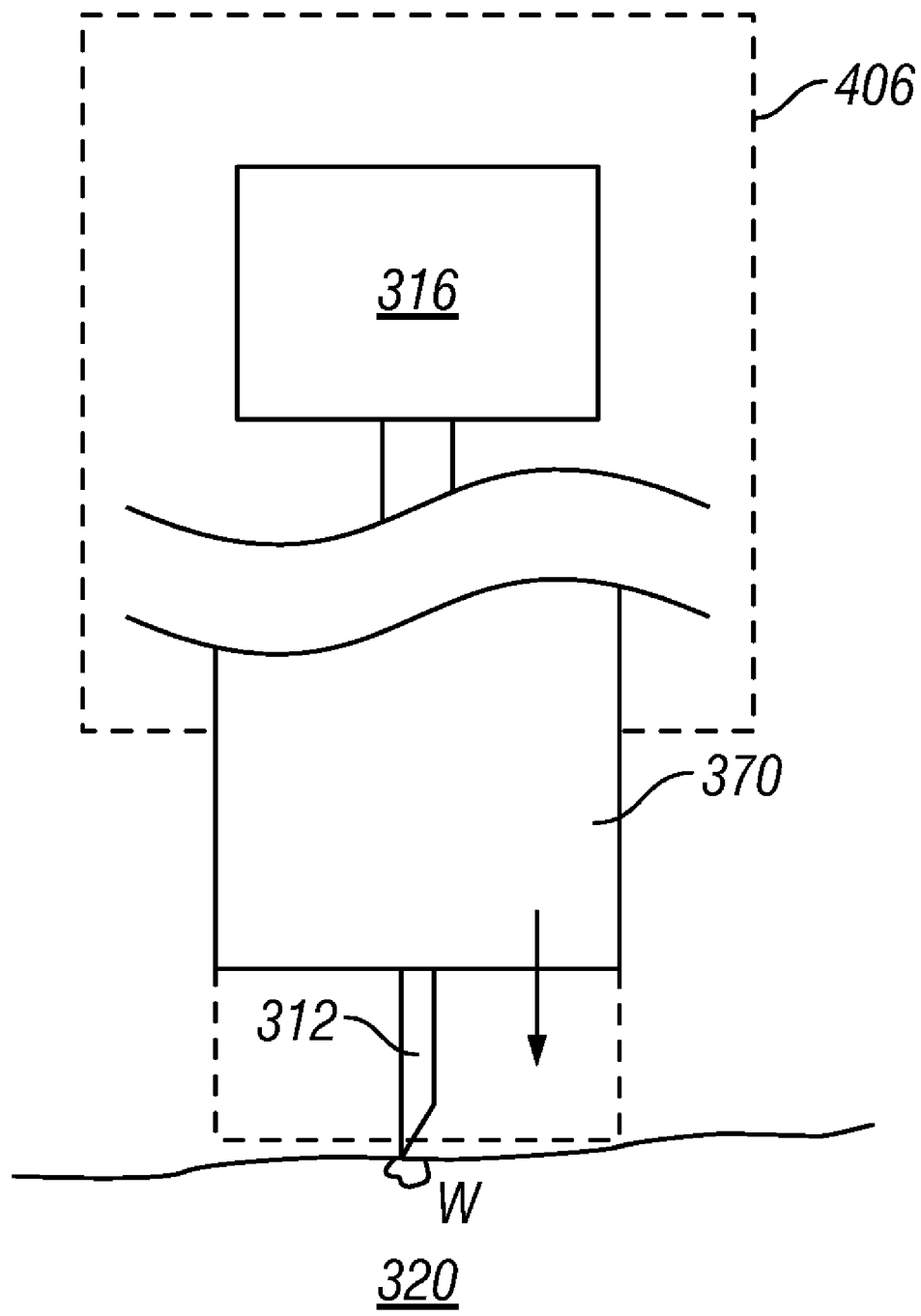
FIG. 37 shows a system according to the present invention with a moveable cartridge.

Referring now to FIGS. 36 and 37, a cartridge 370 is shown with a penetrating member 312 creating a wound W in the tissue site 320. In FIG. 36, a movable capillary member 420 is extended towards the wound W as indicated by arrow 422 to gather body fluid being expressed from the wound. The fluid may be drawn to a sample chamber 384 (not shown). In FIG. 37, the wound W is created and then the entire cartridge is moved to the tissue site 320 to gather body fluid from the wound W. In some embodiments, the cartridge 370 moves towards the wound W relative to the housing 406.

Tissue penetrating systems 310 of FIGS. 22 through 37, can be utilized in a variety of different applications to detect any number of different analytes, including but not limited to glucose. The systems 310 may be used to measure potassium, other ions, or analytes associated with the process of glucose monitoring. The analyte detecting member 390 may further be adapted to measure other analytes found in body fluid.

In a still further embodiment, penetrating member 312 may be moved and positioned to be in engagement with penetrating member driver 316. Penetrating member 312 is in a sterile environment, and prior to launch, the sterilizing covering, which can be a seal is removed. Tissue stabilizing member can apply a stimulation to a surface of the target tissue 320 prior to, and during penetration by penetration member. Penetrating member 312 is engaged with penetrating driving member and controllably pierces a target tissue 320 site. Penetrating member sensor 324 is utilized to control penetration depth and velocity of penetrating member 312. Penetrating member 312 is stopped at a desired depth below a surface of target tissue 320 in order to reduce or eliminate without multiple oscillations against the surface of target tissue 320. A wound is created, causing blood to flow into sample chamber 384. In various embodiments, no more than 1 µL of a body fluid is collected in sample chamber 384.

A number of different preferences, options, embodiment, and features have been given above, and following any one of these may results in an embodiment of this invention that is more presently preferred than a embodiment in which that particular preference is not followed. These preferences, options, embodiment, and features may be generally independent, and additive; and following more than one of these preferences may result in a more presently preferred embodiment than one in which fewer of the preferences are followed.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. Any of the embodiments of the invention may be modified to include any of the features described above or feature incorporated by reference herein. For example, the cartridge of FIG. 26 may be adapted to include a distal portion with a tissue stabilizing member. The cartridge of FIG. 26 may be adapted for use with a vacuum device. The cartridge may include indexing features such as notches on the distal portion or outer radial periphery for those cartridges with a radial configuration. The notches will facilitate positioning, among other things, and may be used for movement. Other cartridges or tapes herein may be modified with notches or tractor holes to facilitate movement. User interfaces, human interfaces, and other interfaces may be added to any of the embodiments of the present invention.

With any of the above embodiments, the location of the penetrating member drive device may be varied, relative to the penetrating members or the cartridge. With any of the above embodiments, the penetrating member tips may be uncovered during actuation (i.e. penetrating members do not pierce the penetrating member enclosure or protective foil during launch). With any of the above embodiments, the penetrating members may be a bare penetrating member during launch. With any of the above embodiments, the penetrating members may be bare penetrating members prior to launch as this may allow for significantly tighter densities of penetrating members. In some embodiments, the penetrating members may be bent, curved, textured, shaped, or otherwise treated at a proximal end or area to facilitate handling by an actuator. The penetrating member may be configured to have a notch or groove to facilitate coupling to a gripper or coupler. The notch or groove may be formed along an elongate portion of the penetrating member. The coupler may be designed to create a frictional only type grip on the penetrating member.

With any of the above embodiments, any open cavity housing the penetrating may be on the bottom or the top of the cartridge, with the gripper on the other side. In some embodiments, sensors may be printed on the top, bottom, or side of the cavities. The front end of the cartridge may be in contact with a user during lancing. The same driver may be used for advancing and retraction of the penetrating member. The penetrating member may have a diameters and length suitable for obtaining the blood volumes described herein. The penetrating member driver may also be in substantially the same plane as the cartridge. The driver may use a through hole or other opening to engage a proximal end of a penetrating member to actuate the penetrating member along a path into and out of the tissue.

Any of the features described in this application or any reference disclosed herein may be adapted for use with any embodiment of the present invention. For example, the devices of the present invention may also be combined for use with injection penetrating members or needles as described in commonly assigned, copending U.S. patent application Ser. No. 10/127,395 filed Apr. 19, 2002. A sensor to detect the presence of foil may also be included in the lancing apparatus. For example, if a cavity has been used before, the foil or sterility barrier will be punched. The sensor can detect if the cavity is fresh or not based on the status of the barrier. It should be understood that in optional embodiments, the sterility barrier may be designed to pierce a sterility barrier of thickness that does not dull a tip of the penetrating member. The lancing apparatus may also use improved drive mechanisms. For example, a solenoid force generator may be improved to try to increase the amount of force the solenoid can generate for a given current. A solenoid for use with the present invention may have five coils and in the present embodiment the slug is roughly the size of two coils. One change is to increase the thickness of the outer metal shell or windings surround the coils. By increasing the thickness, the flux will also be increased. The slug may be split; two smaller slugs may also be used and offset by ½ of a coil pitch. This allows more slugs to be approaching a coil where it could be accelerated. This creates more events where a slug is approaching a coil, creating a more efficient system.

In another optional alternative embodiment, a gripper in the inner end of the protective cavity may hold the penetrating member during shipment and after use, eliminating the feature of using the foil, protective end, or other part to retain the used penetrating member. Some other advantages of the disclosed embodiments and features of additional embodiments include: same mechanism for transferring the used penetrating members to a storage area; a high number of penetrating members such as 25, 50, 75, 100, 500, or more penetrating members may be put on a disk or cartridge; molded body about a penetrating member becomes unnecessary; manufacturing of multiple penetrating member devices is simplified through the use of cartridges; handling is possible of bare rods metal wires, without any additional structural features, to actuate them into tissue; maintaining extreme (better than 50 micron-lateral- and better than 20 micron vertical) precision in guiding; and storage system for new and used penetrating members, with individual cavities/slots is provided. The housing of the lancing device may also be sized to be ergonomically pleasing. In one embodiment, the device has a width of about 56 mm, a length of about 105 mm and a thickness of about 15 mm. Additionally, some embodiments of the present invention may be used with non-electrical force generators or drive mechanism. For example, the punch device and methods for releasing the penetrating members from sterile enclosures could be adapted for use with spring based launchers. The gripper using a frictional coupling may also be adapted for use with other drive technologies.

Still further optional features may be included with the present invention. For example, with any of the above embodiments, the location of the penetrating member drive device may be varied, relative to the penetrating members or the cartridge. With any of the above embodiments, the penetrating member tips may be uncovered during actuation (i.e. penetrating members do not pierce the penetrating member enclosure or protective foil during launch). The penetrating members may be a bare penetrating member during launch. The same driver may be used for advancing and retraction of the penetrating member. Different analyte detecting members detecting different ranges of glucose concentration, different analytes, or the like may be combined for use with each penetrating member. Non-potentiometric measurement techniques may also be used for analyte detection. For example, direct electron transfer of glucose oxidase molecules adsorbed onto carbon nanotube powder microelectrode may be used to measure glucose levels. In all methods, nanoscopic wire growth can be carried out via chemical vapor deposition (CVD). In all of the embodiments of the invention, preferred nanoscopic wires may be nanotubes. Any method useful for depositing a glucose oxidase or other analyte detection material on a nanowire or nanotube may be used with the present invention. Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A body fluid sampling system for use on a tissue site, the system comprising:
   an electrically powered drive force generator;
   a penetrating member operatively coupled to said electrically powered drive force generator, said electrically powered drive force generator moving said member along a path out of a housing having a penetrating member exit, into said tissue site, stopping in said tissue site, and withdrawing out of said tissue site;
   a disposable housing said penetrating member, said disposable having a first and a second seal formed at a distal end and a proximal end of said disposable respectively to maintain a sterile environment around a portion of the penetration member prior to penetrating member actuation;
   a user interface including a sensor for detecting and responding to audio commands from a user; and
   a processor coupled to and receiving a signal from said user interface, said processor monitoring and controlling velocity of said penetrating member via said electrically power drive force generator in response to said signal.

2. The system of claim 1, wherein the user interface relays information to a user via an audio device.

3. The system of claim 1, wherein the user interface relays information to a user via a wireless device.

4. The system of claim 1, further comprising:
   the processor coupled to the electrically powered drive force generator and configured to change a direction and magnitude of force exerted on the penetrating member as it penetrates or advances through the target tissue.

5. The system of claim 1, further comprising:
   a penetrating member sensor configured to detect a penetrating member position during target tissue penetration.

6. The system of claim 1, wherein the at least one output is selected from, a penetration event of a penetrating member, number of penetrating members remaining, time of day, alarm, penetrating member trajectory waveform profile information, force for last penetration event, the last penetration event, how or low battery status, analyte status, time to change support status, jamming malfunction, and system status.

7. The system of claim 1, wherein the user interface is selected from an LED, an LED digital display, an LCD display, a sound generator, a buzzer, and a vibrating device.

8. The system of claim 1, wherein the housing is selected from at least one of, a telephone, a watch, a PDA, electronic device, medical device, point of care device and a decentralized diagnostic device.

9. The system of claim 1, further comprising:
   an input device coupled to the housing, the input device selected from one or more pushbuttons, a touch pad independent of the display device, or a touch sensitive screen on a visual display.

10. The system of claim 1, further comprising:
    a data exchange device for coupling the tissue penetrating system to support equipment.

11. The system of claim 10, further comprising:
    a data interface configured to couple the tissue penetrating system to support equipment with a data interface.

12. The system of claim 1, further comprising:
    a data exchange device for coupling the tissue penetrating system to support equipment selected from one of the following: personal computer, modem, PDA and a computer network.

13. The system of claim 1, wherein the user interface includes a real time clock and one or more alarms a user can set for reminders of when a next target tissue penetration event is needed.

14. The system of claim 1, wherein the user interface is coupled to receive signals from a user interface processor separate from a processor coupled to the penetrating member driver.

15. The system of claim 14, wherein the user interface processor has a sleep mode and runs intermittently to conserve power.

16. The system of claim 15, wherein the user interface processor has logic that provides an alarm time set for a first subset of days and a second alarm time set for a second subset of days.

17. The system of claim 16, wherein the first subset of days is Monday thru Friday and the second subset of days is Saturday and Sunday.

18. The system of claim 1, further comprising:
    a memory for storing at least one of, a number of penetrating members used, number of target tissue penetrating events, time and date of the last selected number of target tissue penetrating events, time interval between alarm and target tissue penetrating event, stratum corneum thickness, time of day, energy consumed by a penetrating member driver to drive a penetrating member into the target tissue, depth of penetrating member penetration, velocity of the penetrating member, a desired velocity profile, velocity of the penetrating member into the target tissue, velocity of the penetrating member out of the target tissue, dwell time of the penetrating member in the target tissue, a target tissue relaxation parameter, force delivered on the target tissue, dwell time of the penetrating member, battery status, system status, consumed energy, speed profile of the penetrating member as the penetrating penetrates and advances through the target tissue, a tissue target tissue relaxation parameter, information relative to contact of a penetrating member with target tissue before penetration by the penetrating member, information relative to a change of speed of a penetrating member as in travels in the target tissue, information relative to consumed sensors and information relative to consumed penetrating members.

19. A body fluid sampling system for use on a tissue site, the system comprising:
- an electrically powered drive force generator;
- a penetrating member operatively coupled to said electrically powered drive force generator, said electrically powered drive force generator moving said member along a path out of a housing having a penetrating member exit, into said tissue site, stopping in said tissue site, and withdrawing out of said tissue site;
- a disposable housing said penetrating member, said disposable having a first and a second seal formed at a distal end and a proximal end of said disposable respectively to maintain a sterile environment around a portion of the penetration member prior to penetrating member actuation;
- a processor monitoring and controlling velocity of said penetrating member via said electrically powered drive force generator; and a user interface
- coupled to said processor providing at least one status of said penetrating member.

* * * * *